(12) United States Patent
Yasukawa et al.

(10) Patent No.: US 10,940,185 B2
(45) Date of Patent: Mar. 9, 2021

(54) LYOPHILIZED PREPARATION

(71) Applicant: JCR Pharmaceuticals Co., Ltd., Hyogo (JP)

(72) Inventors: Hidehito Yasukawa, Kobe (JP); Yuka Yamaguchi, Kobe (JP); Shinji Okabe, Kobe (JP)

(73) Assignee: JCR Pharmaceuticals Co., Ltd., Hyogo (JP)

( * ) Notice: Subject to any disclaimer, the term of this patent is extended or adjusted under 35 U.S.C. 154(b) by 0 days.

(21) Appl. No.: 16/474,307

(22) PCT Filed: Dec. 28, 2017

(86) PCT No.: PCT/JP2017/047207
§ 371 (c)(1),
(2) Date: Jun. 27, 2019

(87) PCT Pub. No.: WO2018/124277
PCT Pub. Date: Jul. 5, 2018

(65) Prior Publication Data
US 2019/0336586 A1 Nov. 7, 2019

(30) Foreign Application Priority Data
Dec. 28, 2016 (JP) .............. JP2016-257060

(51) Int. Cl.
| | |
|---|---|
| *C12N 9/16* | (2006.01) |
| *A61K 38/46* | (2006.01) |
| *A61K 9/19* | (2006.01) |
| *A61K 47/02* | (2006.01) |
| *A61K 47/10* | (2017.01) |
| *A61K 47/26* | (2006.01) |
| *A61K 47/34* | (2017.01) |
| *C07K 16/28* | (2006.01) |

(52) U.S. Cl.
CPC .............. *A61K 38/465* (2013.01); *A61K 9/19* (2013.01); *A61K 47/02* (2013.01); *A61K 47/10* (2013.01); *A61K 47/26* (2013.01); *A61K 47/34* (2013.01); *C07K 16/28* (2013.01)

(58) Field of Classification Search
CPC .... C12Y 301/06013; C12Y 301/01076; C12Y 301/01031; C12N 9/16; C12N 9/2402; C07K 2319/00; A61K 9/19
See application file for complete search history.

(56) References Cited

U.S. PATENT DOCUMENTS

| | | |
|---|---|---|
| 2005/0220786 A1 | 10/2005 | Mahler et al. |
| 2009/0117097 A1 | 5/2009 | Igawa et al. |
| 2009/0291076 A1 | 11/2009 | Morichika et al. |
| 2010/0137213 A1 | 6/2010 | Fernandez et al. |
| 2010/0158925 A1 | 6/2010 | Agarkhed et al. |
| 2011/0318323 A1 | 12/2011 | Zhu et al. |
| 2012/0009171 A1* | 1/2012 | Salamat-Miller ......... A61P 3/00 424/94.3 |
| 2012/0014936 A1 | 1/2012 | Natoli et al. |
| 2012/0264687 A1 | 10/2012 | Tani et al. |
| 2015/0259419 A1 | 9/2015 | Liu et al. |
| 2016/0369001 A1 | 12/2016 | Sonoda et al. |
| 2018/0179291 A1 | 6/2018 | Sonoda et al. |

FOREIGN PATENT DOCUMENTS

| | | |
|---|---|---|
| EP | 3088518 A1 | 11/2016 |
| JP | 2009-540015 A | 11/2009 |
| JP | 2010-534723 A | 11/2010 |
| JP | 2012-501332 A | 1/2012 |
| JP | 2012-521194 A | 9/2012 |
| JP | 2013-530988 A | 8/2013 |
| JP | 2015-509526 A | 3/2015 |
| JP | 2015-163637 A | 9/2015 |
| JP | 2016-519124 A | 6/2016 |
| JP | 2016-185971 A | 10/2016 |
| WO | 2006/132363 A1 | 12/2006 |
| WO | 2007/074880 A1 | 7/2007 |
| WO | 2007/147001 A2 | 12/2007 |
| WO | 2009/018122 A2 | 2/2009 |
| WO | 2009/073569 A2 | 6/2009 |

(Continued)

OTHER PUBLICATIONS

International Preliminary Report on Patentability and Written Opinion issued in corresponding International Patent Application No. PCT/JP2017/047207 dated Jul. 11, 2019.
International Search Report issued in corresponding International Patent Application No. PCT/JP2017/047207 dated Mar. 6, 2018.
Search Report and Written Opinion issued in counterpart Singapore Patent Application No. 11201905283W dated May 26, 2020.

(Continued)

*Primary Examiner* — Karen Cochrane Carlson

(74) *Attorney, Agent, or Firm* — Morgan, Lewis & Bockius LLP

(57) ABSTRACT

[Problem] To provide a pharmaceutical composition containing a fusion protein comprising an antibody and a lysosomal enzyme as an active ingredient, which is stable enough to permit its distribution to the market.

[Solution] A lyophilized formulation containing; a fusion protein comprising an antibody and a lysosomal enzyme as an active ingredient, and further containing a neutral salt, a disaccharide, a nonionic surfactant, and a buffer. Such a lyophilized formulation includes, for example, as an active ingredient, a fusion protein comprising an anti-transferrin receptor antibody and human iduronate-2-sulfatase, and further containing sodium chloride as the neutral salt, sucrose as the disaccharide, poloxamer as the nonionic surfactant, and phosphate buffer as the buffer.

29 Claims, No Drawings

Specification includes a Sequence Listing.

(56)     References Cited

FOREIGN PATENT DOCUMENTS

| | | |
|---|---|---|
| WO | 2010/027766 A1 | 3/2010 |
| WO | 2010/108048 A2 | 9/2010 |
| WO | 2011/163647 A2 | 12/2011 |
| WO | 2013/164837 A1 | 11/2013 |
| WO | 2014/105810 A1 | 7/2014 |
| WO | 2014/177568 A1 | 11/2014 |
| WO | 2015/009961 A1 | 1/2015 |
| WO | 2015/098989 A1 | 7/2015 |
| WO | 2015/136470 A1 | 9/2015 |
| WO | 2016/208695 A1 | 12/2016 |
| WO | 2016/208696 A1 | 12/2016 |
| WO | 2017/147414 A1 | 8/2017 |

OTHER PUBLICATIONS

Extended European Search Report issued in counterpart European Patent Application No. 17888295.7 dated Sep. 11, 2020.

\* cited by examiner

SEQUENCE LISTING

```
<160> NUMBER OF SEQ ID NOS: 61

<210> SEQ ID NO 1
<211> LENGTH: 525
<212> TYPE: PRT
<213> ORGANISM: Homo sapiens

<400> SEQUENCE: 1

Ser Glu Thr Gln Ala Asn Ser Thr Thr Asp Ala Leu Asn Val Leu Leu
1               5                   10                  15
```

```
Ile Ile Val Asp Asp Leu Arg Pro Ser Leu Gly Cys Tyr Gly Asp Lys
             20                  25                  30

Leu Val Arg Ser Pro Asn Ile Asp Gln Leu Ala Ser His Ser Leu Leu
         35                  40                  45

Phe Gln Asn Ala Phe Ala Gln Ala Val Cys Ala Pro Ser Arg Val
     50                  55                  60

Ser Phe Leu Thr Gly Arg Arg Pro Asp Thr Thr Arg Leu Tyr Asp Phe
 65                  70                  75                  80

Asn Ser Tyr Trp Arg Val His Ala Gly Asn Phe Ser Thr Ile Pro Gln
                 85                  90                  95

Tyr Phe Lys Glu Asn Gly Tyr Val Thr Met Ser Val Gly Lys Val Phe
                100                 105                 110

His Pro Gly Ile Ser Ser Asn His Thr Asp Asp Ser Pro Tyr Ser Trp
            115                 120                 125

Ser Phe Pro Pro Tyr His Pro Ser Ser Glu Lys Tyr Glu Asn Thr Lys
    130                 135                 140

Thr Cys Arg Gly Pro Asp Gly Glu Leu His Ala Asn Leu Leu Cys Pro
145                 150                 155                 160

Val Asp Val Leu Asp Val Pro Glu Gly Thr Leu Pro Asp Lys Gln Ser
                165                 170                 175

Thr Glu Gln Ala Ile Gln Leu Leu Glu Lys Met Lys Thr Ser Ala Ser
            180                 185                 190

Pro Phe Phe Leu Ala Val Gly Tyr His Lys Pro His Ile Pro Phe Arg
        195                 200                 205

Tyr Pro Lys Glu Phe Gln Lys Leu Tyr Pro Leu Glu Asn Ile Thr Leu
210                 215                 220

Ala Pro Asp Pro Glu Val Pro Asp Gly Leu Pro Pro Val Ala Tyr Asn
225                 230                 235                 240

Pro Trp Met Asp Ile Arg Gln Arg Glu Asp Val Gln Ala Leu Asn Ile
                245                 250                 255

Ser Val Pro Tyr Gly Pro Ile Pro Val Asp Phe Gln Arg Lys Ile Arg
            260                 265                 270

Gln Ser Tyr Phe Ala Ser Val Ser Tyr Leu Asp Thr Gln Val Gly Arg
        275                 280                 285

Leu Leu Ser Ala Leu Asp Asp Leu Gln Leu Ala Asn Ser Thr Ile Ile
290                 295                 300

Ala Phe Thr Ser Asp His Gly Trp Ala Leu Gly Glu His Gly Glu Trp
305                 310                 315                 320

Ala Lys Tyr Ser Asn Phe Asp Val Ala Thr His Val Pro Leu Ile Phe
                325                 330                 335

Tyr Val Pro Gly Arg Thr Ala Ser Leu Pro Glu Ala Gly Glu Lys Leu
            340                 345                 350

Phe Pro Tyr Leu Asp Pro Phe Asp Ser Ala Ser Gln Leu Met Glu Pro
        355                 360                 365

Gly Arg Gln Ser Met Asp Leu Val Glu Leu Val Ser Leu Phe Pro Thr
370                 375                 380

Leu Ala Gly Leu Ala Gly Leu Gln Val Pro Pro Arg Cys Pro Val Pro
385                 390                 395                 400

Ser Phe His Val Glu Leu Cys Arg Glu Gly Lys Asn Leu Leu Lys His
                405                 410                 415

Phe Arg Phe Arg Asp Leu Glu Glu Asp Pro Tyr Leu Pro Gly Asn Pro
            420                 425                 430

Arg Glu Leu Ile Ala Tyr Ser Gln Tyr Pro Arg Pro Ser Asp Ile Pro
```

```
                   435                 440                 445

Gln Trp Asn Ser Asp Lys Pro Ser Leu Lys Asp Ile Lys Ile Met Gly
    450                 455                 460

Tyr Ser Ile Arg Thr Ile Asp Tyr Arg Tyr Thr Val Trp Val Gly Phe
465                 470                 475                 480

Asn Pro Asp Glu Phe Leu Ala Asn Phe Ser Asp Ile His Ala Gly Glu
                485                 490                 495

Leu Tyr Phe Val Asp Ser Asp Pro Leu Gln Asp His Asn Met Tyr Asn
            500                 505                 510

Asp Ser Gln Gly Gly Asp Leu Phe Gln Leu Leu Met Pro
            515                 520                 525

<210> SEQ ID NO 2
<211> LENGTH: 214
<212> TYPE: PRT
<213> ORGANISM: Artificial Sequence
<220> FEATURE:
<223> OTHER INFORMATION: Amino acid sequence of the light-chain of
      humanized anti-hTfR antibody No. 1

<400> SEQUENCE: 2

Asp Ile Gln Val Thr Gln Ser Pro Ser Phe Leu Ser Ala Ser Val Gly
1               5                   10                  15

Asp Arg Val Thr Ile Thr Cys Lys Ala Ser Gln Asp Val Asn Ser Ala
            20                  25                  30

Val Ala Trp Phe Gln Gln Lys Pro Gly Lys Ala Pro Lys Leu Leu Ile
        35                  40                  45

Tyr Trp Thr Ser Thr Arg His Thr Gly Val Pro Asp Arg Phe Ser Gly
    50                  55                  60

Ser Gly Ser Gly Thr Val Tyr Thr Leu Thr Ile Ser Ser Leu Gln Pro
65                  70                  75                  80

Glu Asp Phe Ala Thr Tyr Tyr Cys Gln Gln His Tyr Ser Thr Pro Arg
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 725
<212> TYPE: DNA
<213> ORGANISM: Artificial Sequence
<220> FEATURE:
<223> OTHER INFORMATION: Nucleotide sequence encoding amino acid
      sequence of the light chain of humanized anti-hTfR antibody No. 1,
      synthetic sequence
```

```
<400> SEQUENCE: 3
acgcgtgccg ccaccatggg ctggagctgg attctgctgt tcctcctgag cgtgacagca      60
ggagtgcaca gcgacatcca ggtcacacag tcaccaagtt ttctgagcgc aagcgtgggc     120
gacagggtca ctatcacatg caaggcaagc caggacgtga actccgcagt ggcctggttc     180
cagcagaagc cagggaaagc acccaagctg ctgatctatt ggacctctac aaggcacacc     240
ggtgtcccag atcggttctc aggttccggc agcggaacag tgtatactct gaccatttcc     300
agcctgcagc ctgaagactt cgctacttac tattgccagc agcattactc accccaaga     360 acatttggcg gagggactaa agtggagatc aagaggaccg tggccgctcc ctccgtcttc     420
atttttcccc ctagcgacga acagctgaag agtggcacag cctcagtggt ctgtctgctg     480
aacaatttct accctaggga ggctaaagtg cagtggaagg tcgataacgc actgcagtct     540
ggaaatagtc aggagtcagt gacagaacag gactccaaag atagcactta ttctctgtct     600
agtacactga ctctgagcaa ggccgattac gaaaagcaca agtgtatgc ttgcgaagtc      660 acccatcagg ggctgtcatc accagtcacc aagtcattca atagaggcga gtgctaagcg     720
gccgc                                                                  725

<210> SEQ ID NO 4
<211> LENGTH: 214
<212> TYPE: PRT
<213> ORGANISM: Artificial Sequence
<220> FEATURE:
<223> OTHER INFORMATION: Amino acid sequence of the light chain of
      humanized anti-hTfR antibody No. 2

<400> SEQUENCE: 4

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asn Asn
            20                  25                  30

Leu Gln Trp Tyr Gln Gln Lys Pro Asp Gln Ser Pro Lys Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Leu Cys Gln Gln Ser Asn Ser Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

Phe Asn Arg Gly Glu Cys
210

<210> SEQ ID NO 5
<211> LENGTH: 725
<212> TYPE: DNA
<213> ORGANISM: Artificial Sequence
<220> FEATURE:
<223> OTHER INFORMATION: Nucleotide sequence encoding amino acid
      sequence of the light chain of humanized anti-hTfR antibody No. 2,
      synthetic sequence

<400> SEQUENCE: 5

```
acgcgtgccg ccaccatggg ctggagctgg attctgctgt tcctcctgag cgtgacagca      60
ggagtgcaca gcgaaattgt gctgacccag tctcccgatt ccagtccgt gaccccaag       120
gagaaagtca ccatcacatg cagagcatca cagtccatta gcaacaatct gcagtggtac     180
cagcagaagc cagaccagag ccccaagctg ctgatcaaat atgcctctca gagtatttca     240
ggcataccct tctaggttctc cggtagcggc tctggaaccg acttactct gaccatcaac     300
agtctggagg ctgaagatgc cgctacatac ttgtgccagc agagtaattc atggcctagg    360
acctttggcc aggggacaaa ggtggagatc aaaaggactg tggcagcccc aagtgtcttc    420
attttcccc cttcagacga acagctgaag agcggcacag catctgtggt ctgtctgctg     480
aacaatttct acccacggga ggctaaggtg cagtggaaag tcgataacgc actgcagtcc    540
ggaaatagcc aggagtctgt gactgaacag gacagtaagg attcaaccta tccctgtcc    600
agcacactga ctctgagcaa agccgattac gagaagcaca agtgtatgc ttgcgaagtc    660
acacatcagg ggctgtctag tcccgtgact aagtcttta taggggtga atgttaagcg     720
gccgc                                                                725
```

<210> SEQ ID NO 6
<211> LENGTH: 219
<212> TYPE: PRT
<213> ORGANISM: Artificial Sequence
<220> FEATURE:
<223> OTHER INFORMATION: amino acid sequence of the light chain of
      humanized anti-hTfR antibody No. 3

<400> SEQUENCE: 6

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

```
Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 7
<211> LENGTH: 740
<212> TYPE: DNA
<213> ORGANISM: Artificial Sequence
<220> FEATURE:
<223> OTHER INFORMATION: Nucleotide sequence encoding amino acid
      sequence of the light chain of humanized anti-hTfR antibody No. 3,
      synthetic sequence

<400> SEQUENCE: 7

```
acgcgtgccg ccaccatggg ctggagctgg attctgctgt tcctcctgag cgtgacagca    60
ggagtgcaca gcgacatcgt gatgacccag actcccctga gcctgagcgt gacacctggc   120
cagcctgcca gcatcagctg cagaagctct cagagcctgg tgcacagcaa cggcaacacc   180
tacctgcact ggtatctgca gaagcccggc cagagccctc agctgctgat ctacaaggtg   240
tccaacagat tcagcggcgt gcccgacaga ttctccggca gcggctctgg caccgacttc   300
accctgaaga tttccagagt ggaagccgag gacgtgggcg tgtactactg cagccagagc   360
acccacgtgc cctggacatt cggccagggc accaaggtgg aaatcaagag aaccgtggcc   420
gctcccagcg tgttcatctt cccacctagc gacgagcagc tgaagtccgg cacagcctct   480
gtcgtgtgcc tgctgaacaa cttctacccc cgcgaggcca aggtgcagtg gaaggtggac   540
aacgccctgc agagcggcaa cagccaggaa agcgtgaccg agcaggactc caaggacagc   600
acctacagcc tgagcagcac cctgaccctg agcaaggccg actacgagaa gcacaaggtg   660
tacgcctgcg aagtgaccca ccagggcctg tctagccccg tgaccaagag cttcaacaga   720
ggcgagtgct aagcggccgc                                              740
```

<210> SEQ ID NO 8
<211> LENGTH: 446
<212> TYPE: PRT
<213> ORGANISM: Artificial Sequence
<220> FEATURE:
<223> OTHER INFORMATION: Amino acid sequence of the heavy chain of
      humanized anti-hTfR antibody No. 1

<400> SEQUENCE: 8

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Thr Phe Ser Asn Tyr
            20                  25                  30

Gly Met Ser Trp Val Arg Gln Ala Pro Gly Lys Gly Leu Glu Leu Val
        35                  40                  45

Ala Asn Ile Asn Thr Asn Gly Gly Ser Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80
```

```
Leu Gln Met Asn Ser Leu Arg Ala Glu Asp Thr Ala Val Tyr Tyr Cys
             85                  90                  95

Thr Asn Asn Arg Tyr Asp Glu Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
            130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                    165                 170                 175

Gly Leu Tyr Ser Leu Ser Ser Val Val Thr Val Pro Ser Ser Ser Leu
                    180                 185                 190

Gly Thr Gln Thr Tyr Ile Cys Asn Val Asn His Lys Pro Ser Asn Thr
                195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
            435                 440                 445

<210> SEQ ID NO 9
<211> LENGTH: 453
<212> TYPE: PRT
<213> ORGANISM: Artificial Sequence
<220> FEATURE:
<223> OTHER INFORMATION: Amino acid sequence of the heavy chain of
      humanized anti-hTfR antibody No. 2

<400> SEQUENCE: 9
```

-continued

```
Gln Val Gln Leu Val Gln Ser Gly Ala Glu Lys Lys Pro Gly Ala
 1               5                  10                  15

Ser Val Lys Val Ser Cys Lys Ala Ser Gly Tyr Thr Phe Thr Asp Tyr
             20                  25                  30

Val Met His Trp Val Arg Gln Ala Pro Gly Gln Gly Leu Glu Trp Ile
         35                  40                  45

Gly Val Ile Ser Thr Tyr Tyr Gly His Gly Ser Tyr Asn Gln Arg Phe
     50                  55                  60

Lys Gly Arg Ala Thr Met Thr Val Asp Lys Ser Ile Ser Thr Ala Tyr
 65                  70                  75                  80

Met Glu Leu Val Arg Leu Arg Ser Asp Asp Thr Ala Val Tyr Tyr Cys
                 85                  90                  95

Val Arg Gly Gly Tyr Gly Ser Ser Leu Ala Gly Asn Phe Asp Val
             100                 105                 110

Trp Gly Gln Gly Thr Thr Val Thr Val Ser Ser Ala Ser Thr Lys Gly
         115                 120                 125

Pro Ser Val Phe Pro Leu Ala Pro Ser Ser Lys Ser Thr Ser Gly Gly
     130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                 165                 170                 175

Pro Ala Val Leu Gln Ser Ser Gly Leu Tyr Ser Leu Ser Ser Val Val
             180                 185                 190

Thr Val Pro Ser Ser Ser Leu Gly Thr Gln Thr Tyr Ile Cys Asn Val
         195                 200                 205

Asn His Lys Pro Ser Asn Thr Lys Val Asp Lys Lys Val Glu Pro Lys
     210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                 245                 250                 255

Leu Met Ile Ser Arg Thr Pro Glu Val Thr Cys Val Val Val Asp Val
             260                 265                 270

Ser His Glu Asp Pro Glu Val Lys Phe Asn Trp Tyr Val Asp Gly Val
         275                 280                 285

Glu Val His Asn Ala Lys Thr Lys Pro Arg Glu Glu Gln Tyr Asn Ser
     290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                 325                 330                 335

Pro Ile Glu Lys Thr Ile Ser Lys Ala Lys Gly Gln Pro Arg Glu Pro
             340                 345                 350

Gln Val Tyr Thr Leu Pro Pro Ser Arg Asp Glu Leu Thr Lys Asn Gln
         355                 360                 365

Val Ser Leu Thr Cys Leu Val Lys Gly Phe Tyr Pro Ser Asp Ile Ala
     370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                 405                 410                 415
```

```
Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys
    450

<210> SEQ ID NO 10
<211> LENGTH: 448
<212> TYPE: PRT
<213> ORGANISM: Artificial Sequence
<220> FEATURE:
<223> OTHER INFORMATION: Amino acid sequence of the heavy chain of
      humanized anti-hTfR antibody No. 3

<400> SEQUENCE: 10

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Leu Gly Trp Val Arg Gln Met Pro Gly Lys Gly Leu Glu Trp Met
        35                  40                  45

Gly Asp Ile Tyr Pro Gly Gly Asp Tyr Pro Thr Tyr Ser Glu Lys Phe
    50                  55                  60

Lys Val Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Gly Asn Tyr Asp Glu Val Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320
```

```
Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 11
<211> LENGTH: 20
<212> TYPE: DNA
<213> ORGANISM: Artificial Sequence
<220> FEATURE:
<223> OTHER INFORMATION: Primer Hyg-Sfi5', synthetic sequence

<400> SEQUENCE: 11
gaggccgcct cggcctctga                                              20

<210> SEQ ID NO 12
<211> LENGTH: 29
<212> TYPE: DNA
<213> ORGANISM: Artificial Sequence
<220> FEATURE:
<223> OTHER INFORMATION: Primer Hyg-BstX3', synthetic sequence

<400> SEQUENCE: 12
aaccatcgtg atgggtgcta ttcctttgc                                    29

<210> SEQ ID NO 13
<211> LENGTH: 973
<212> TYPE: PRT
<213> ORGANISM: Artificial Sequence
<220> FEATURE:
<223> OTHER INFORMATION: Amino acid sequence of fused protein of the
      heavy chain of humanized anti-hTfR antibody No.1 and hI2S

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Thr Phe Ser Asn Tyr
            20                  25                  30

Gly Met Ser Trp Val Arg Gln Ala Pro Gly Lys Gly Leu Glu Leu Val
        35                  40                  45

Ala Asn Ile Asn Thr Asn Gly Gly Ser Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Thr Asn Asn Arg Tyr Asp Glu Asp Tyr Trp Gly Gln Gly Thr Leu Val
```

```
                100                 105                 110
Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys Gly Ser
            435                 440                 445

Ser Glu Thr Gln Ala Asn Ser Thr Thr Asp Ala Leu Asn Val Leu Leu
450                 455                 460

Ile Ile Val Asp Asp Leu Arg Pro Ser Leu Gly Cys Tyr Gly Asp Lys
465                 470                 475                 480

Leu Val Arg Ser Pro Asn Ile Asp Gln Leu Ala Ser His Ser Leu Leu
                485                 490                 495

Phe Gln Asn Ala Phe Ala Gln Ala Val Cys Ala Pro Ser Arg Val
                500                 505                 510

Ser Phe Leu Thr Gly Arg Arg Pro Asp Thr Thr Arg Leu Tyr Asp Phe
            515                 520                 525
```

-continued

```
Asn Ser Tyr Trp Arg Val His Ala Gly Asn Phe Ser Thr Ile Pro Gln
        530                 535                 540

Tyr Phe Lys Glu Asn Gly Tyr Val Thr Met Ser Val Gly Lys Val Phe
545                 550                 555                 560

His Pro Gly Ile Ser Ser Asn His Thr Asp Asp Ser Pro Tyr Ser Trp
                565                 570                 575

Ser Phe Pro Pro Tyr His Pro Ser Ser Glu Lys Tyr Glu Asn Thr Lys
            580                 585                 590

Thr Cys Arg Gly Pro Asp Gly Glu Leu His Ala Asn Leu Leu Cys Pro
        595                 600                 605

Val Asp Val Leu Asp Val Pro Glu Gly Thr Leu Pro Asp Lys Gln Ser
610                 615                 620

Thr Glu Gln Ala Ile Gln Leu Leu Glu Lys Met Lys Thr Ser Ala Ser
625                 630                 635                 640

Pro Phe Phe Leu Ala Val Gly Tyr His Lys Pro His Ile Pro Phe Arg
                645                 650                 655

Tyr Pro Lys Glu Phe Gln Lys Leu Tyr Pro Leu Glu Asn Ile Thr Leu
            660                 665                 670

Ala Pro Asp Pro Glu Val Pro Asp Gly Leu Pro Pro Val Ala Tyr Asn
        675                 680                 685

Pro Trp Met Asp Ile Arg Gln Arg Glu Asp Val Gln Ala Leu Asn Ile
690                 695                 700

Ser Val Pro Tyr Gly Pro Ile Pro Val Asp Phe Gln Arg Lys Ile Arg
705                 710                 715                 720

Gln Ser Tyr Phe Ala Ser Val Ser Tyr Leu Asp Thr Gln Val Gly Arg
                725                 730                 735

Leu Leu Ser Ala Leu Asp Asp Leu Gln Leu Ala Asn Ser Thr Ile Ile
            740                 745                 750

Ala Phe Thr Ser Asp His Gly Trp Ala Leu Gly Glu His Gly Glu Trp
        755                 760                 765

Ala Lys Tyr Ser Asn Phe Asp Val Ala Thr His Val Pro Leu Ile Phe
770                 775                 780

Tyr Val Pro Gly Arg Thr Ala Ser Leu Pro Glu Ala Gly Glu Lys Leu
785                 790                 795                 800

Phe Pro Tyr Leu Asp Pro Phe Asp Ser Ala Ser Gln Leu Met Glu Pro
                805                 810                 815

Gly Arg Gln Ser Met Asp Leu Val Glu Leu Val Ser Leu Phe Pro Thr
            820                 825                 830

Leu Ala Gly Leu Ala Gly Leu Gln Val Pro Pro Arg Cys Pro Val Pro
        835                 840                 845

Ser Phe His Val Glu Leu Cys Arg Glu Gly Lys Asn Leu Leu Lys His
850                 855                 860

Phe Arg Phe Arg Asp Leu Glu Glu Asp Pro Tyr Leu Pro Gly Asn Pro
865                 870                 875                 880

Arg Glu Leu Ile Ala Tyr Ser Gln Tyr Pro Arg Pro Ser Asp Ile Pro
                885                 890                 895

Gln Trp Asn Ser Asp Lys Pro Ser Leu Lys Asp Ile Lys Ile Met Gly
            900                 905                 910

Tyr Ser Ile Arg Thr Ile Asp Tyr Arg Tyr Thr Val Trp Val Gly Phe
        915                 920                 925

Asn Pro Asp Glu Phe Leu Ala Asn Phe Ser Asp Ile His Ala Gly Glu
930                 935                 940
```

```
Leu Tyr Phe Val Asp Ser Asp Pro Leu Gln Asp His Asn Met Tyr Asn
945                 950                 955                 960

Asp Ser Gln Gly Gly Asp Leu Phe Gln Leu Leu Met Pro
                965                 970
```

<210> SEQ ID NO 14
<211> LENGTH: 3002
<212> TYPE: DNA
<213> ORGANISM: Artificial Sequence
<220> FEATURE:
<223> OTHER INFORMATION: Nucleotide sequence encoding amino acid sequence of fused protein of the heavy chain of humanized anti-hTfR antibody No.1 and hI2S, synthetic sequence

<400> SEQUENCE: 14

```
acgcgtgccg ccaccatggg ctggagctgg attctgctgt tcctcctgag cgtgacagca    60
ggagtgcaca gcgaagtgca gctggtcgaa tcaggggggg gctggtgca gcctggaggc    120
agcctgagac tgtcctgcgc cgcttctggc ttgacctta gcaactacgg gatgtcctgg    180
gtgcggcagg ctcctggcaa gggactggag ttggtggcca acatcaatac caacggcgga    240
agtacatact atcccgattc agtgaagggc cggttcacca tcagcaggga caacgccaag    300
aacagcctgt atctgcagat gaactctctg agggccgagg atacagccgt gtactattgc    360
actaacaacc ggtacgacga ggactattgg ggccagggca ccctggtgac agtgtctagc    420
gcctctacca agggcccaag cgtgtttcct ctggctccat cctctaaatc cacctctggc    480
ggcacagccg ctctgggctg tctggtgaag gattacttcc cagagcccgt gacagtgtct    540
tggaacagcg gcgccctgac ctccggcgtg cacacatttc ctgctgtgct gcagagctcc    600
ggcctgtaca gcctgtctag cgtggtgacc gtgccatcct ctagcctggg cacccagaca    660
tatatctgca acgtgaatca caagcccagc aatacaaagg tggataagaa ggtggagcca    720
aagtcctgtg acaagaccca cacatgcccc ccttgtcctg ctccagagct gctggggga    780
ccaagcgtgt tcctgtttcc acccaagccc aaggatacc tgatgatctc tcggacccca    840
gaggtgacat gcgtggtggt ggatgtgagc cacgaggacc ccgaggtgaa gttcaactgg    900
tatgtggacg gcgtggaggt gcacaatgct aagaccaagc caggagga gcagtacaac    960
tccacctata gagtggtgtc tgtgctgaca gtgctgcacc aggattggct gaacggcaag   1020
gagtataagt gcaaggtgtc caataaggcc ctgcccgctc tatcgagaa gaccatctct   1080
aaggccaagg gccagcccag agagcctcag gtgtacacac tgcctccatc ccgggatgag   1140
ctgaccaaga accaggtgtc tctgacatgt ctggtcaagg gcttctatcc ctctgacatc   1200
gccgtggagt gggagagcaa tggccagcct gagaacaatt acaagaccac ccccctgtg   1260
ctggattccg acggctcttt cttttctgtat agcaagctga ccgtggacaa gtcccggtgg   1320
cagcagggca acgtgttcag ctgttccgtg atgcacgaag ctctgcataa tcactatact   1380
cagaaatccc tgtcactgtc acctggtaaa ggatcttccg aaacgcaggc caactcgacc   1440
acagatgctc tgaacgttct tctcatcatc gtggatgacc tgcgcccctc cctgggctgt   1500
tatgggata agctggtgag gtccccaaat attgaccaac tggcatccca gcctcctc   1560
ttccagaatg cctttgcgca gcaagcagtg tgcgccccga ccgcgtttc tttcctcact   1620
ggcaggagac ctgacaccac ccgcctgtac gacttcaact cctactggag ggtgcacgct   1680
ggaaacttct ccaccatccc ccagtacttc aaggagaatg ctatgtgac catgtcggtg   1740
ggaaaagtct tcaccctgg gatatcttct aaccataccg atgattctcc gtatagctgg   1800
tcttttccac cttatcatcc ttcctctgag aagtatgaaa acactaagac atgtcgaggg   1860
```

```
ccagatggag aactccatgc caacctgctt tgccctgtgg atgtgctgga tgttcccgag    1920
ggcaccttgc ctgacaaaca gagcactgag caagccatac agttgttgga aaagatgaaa    1980
acgtcagcca gtcctttctt cctggccgtt gggtatcata agccacacat ccccttcaga    2040
taccccaagg aatttcagaa gttgtatccc ttggagaaca tcaccctggc cccgatccc     2100 gaggtccctg atggcctacc ccctgtggcc tacaaccct ggatggacat caggcaacgg     2160
gaagacgtcc aagccttaaa catcagtgtg ccgtatggtc caattcctgt ggactttcag    2220
cggaaaatcc gccagagcta ctttgcctct gtgtcatatt tggatacaca ggtcggccgc    2280
ctcttgagtg ctttggacga tcttcagctg ccaacagca ccatcattgc atttacctcg     2340
gatcatgggt gggctctagg tgaacatgga gaatgggcca atacagcaa ttttgatgtt     2400 gctacccatg ttcccctgat attctatgtt cctggaagga cggcttcact tccggaggca    2460
ggcgagaagc ttttcccctta cctcgaccct tttgattccg cctcacagtt gatggagcca    2520
ggcaggcaat ccatggacct tgtggaactt gtgtctcttt ttcccacgct ggctggactt    2580
gcaggactgc aggttccacc tcgctgcccc gttccttcat ttcacgttga ctgtgcaga     2640 gaaggcaaga accttctgaa gcattttcga ttccgtgact ggaagaaga tccgtacctc     2700 cctggtaatc cccgtgaact gattgcctat agccagtatc cccggccttc agacatccct    2760
cagtggaatt ctgacaagcc gagtttaaaa gatataaaga tcatgggcta ttccatacgc    2820
accatagact ataggtatac tgtgtgggtt ggcttcaatc ctgatgaatt tctagctaac    2880
ttttctgaca tccatgcagg ggaactgtat tttgtggatt ctgacccatt gcaggatcac    2940
aatatgtata atgattccca aggtggagac cttttccagt tgttgatgcc ttaagcggcc    3000
gc                                                                   3002
```

<210> SEQ ID NO 15
<211> LENGTH: 980
<212> TYPE: PRT
<213> ORGANISM: Artificial Sequence
<220> FEATURE:
<223> OTHER INFORMATION: Amino acid sequence of fused protein of the
      heavy chain of humanized anti-hTfR antibody No.2 and hI2S

<400> SEQUENCE: 15

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Val Met His Trp Val Arg Gln Ala Pro Gly Gln Gly Leu Glu Trp Ile
        35                  40                  45

Gly Val Ile Ser Thr Tyr Tyr Gly His Gly Ser Tyr Asn Gln Arg Phe
    50                  55                  60

Lys Gly Arg Ala Thr Met Thr Val Asp Lys Ser Ile Ser Thr Ala Tyr
65                  70                  75                  80

Met Glu Leu Val Arg Leu Arg Ser Asp Asp Thr Ala Val Tyr Tyr Cys
                85                  90                  95

Val Arg Gly Gly Tyr Gly Ser Ser Ser Leu Ala Gly Asn Phe Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140
```

-continued

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
            210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
            290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
            325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
            355                 360                 365

Val Ser Leu Thr Cys Leu Val Lys Gly Phe Tyr Pro Ser Asp Ile Ala
            370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys Gly Ser Ser Glu Thr Gln Ala Asn Ser Thr Thr
            450                 455                 460

Asp Ala Leu Asn Val Leu Leu Ile Ile Val Asp Asp Leu Arg Pro Ser
465                 470                 475                 480

Leu Gly Cys Tyr Gly Asp Lys Leu Val Arg Ser Pro Asn Ile Asp Gln
            485                 490                 495

Leu Ala Ser His Ser Leu Leu Phe Gln Asn Ala Phe Ala Gln Gln Ala
            500                 505                 510

Val Cys Ala Pro Ser Arg Val Ser Phe Leu Thr Gly Arg Arg Pro Asp
            515                 520                 525

Thr Thr Arg Leu Tyr Asp Phe Asn Ser Tyr Trp Arg Val His Ala Gly
            530                 535                 540

Asn Phe Ser Thr Ile Pro Gln Tyr Phe Lys Glu Asn Gly Tyr Val Thr
545                 550                 555                 560

Met Ser Val Gly Lys Val Phe His Pro Gly Ile Ser Ser Asn His Thr

-continued

```
            565                 570                 575
Asp Asp Ser Pro Tyr Ser Trp Ser Phe Pro Tyr His Pro Ser Ser
            580                 585                 590

Glu Lys Tyr Glu Asn Thr Lys Thr Cys Arg Gly Pro Asp Gly Leu
            595                 600                 605

His Ala Asn Leu Leu Cys Pro Val Asp Val Leu Asp Val Pro Glu Gly
            610                 615                 620

Thr Leu Pro Asp Lys Gln Ser Thr Glu Gln Ala Ile Gln Leu Leu Glu
625                 630                 635                 640

Lys Met Lys Thr Ser Ala Ser Pro Phe Phe Leu Ala Val Gly Tyr His
                    645                 650                 655

Lys Pro His Ile Pro Phe Arg Tyr Pro Lys Glu Phe Gln Lys Leu Tyr
                    660                 665                 670

Pro Leu Glu Asn Ile Thr Leu Ala Pro Asp Pro Glu Val Pro Asp Gly
                    675                 680                 685

Leu Pro Pro Val Ala Tyr Asn Pro Trp Met Asp Ile Arg Gln Arg Glu
            690                 695                 700

Asp Val Gln Ala Leu Asn Ile Ser Val Pro Tyr Gly Pro Ile Pro Val
705                 710                 715                 720

Asp Phe Gln Arg Lys Ile Arg Gln Ser Tyr Phe Ala Ser Val Ser Tyr
                    725                 730                 735

Leu Asp Thr Gln Val Gly Arg Leu Leu Ser Ala Leu Asp Asp Leu Gln
                    740                 745                 750

Leu Ala Asn Ser Thr Ile Ile Ala Phe Thr Ser Asp His Gly Trp Ala
            755                 760                 765

Leu Gly Glu His Gly Glu Trp Ala Lys Tyr Ser Asn Phe Asp Val Ala
770                 775                 780

Thr His Val Pro Leu Ile Phe Tyr Val Pro Gly Arg Thr Ala Ser Leu
785                 790                 795                 800

Pro Glu Ala Gly Glu Lys Leu Phe Pro Tyr Leu Asp Pro Phe Asp Ser
                    805                 810                 815

Ala Ser Gln Leu Met Glu Pro Gly Arg Gln Ser Met Asp Leu Val Glu
                    820                 825                 830

Leu Val Ser Leu Phe Pro Thr Leu Ala Gly Leu Ala Gly Leu Gln Val
            835                 840                 845

Pro Pro Arg Cys Pro Val Pro Ser Phe His Val Glu Leu Cys Arg Glu
850                 855                 860

Gly Lys Asn Leu Leu Lys His Phe Arg Phe Arg Asp Leu Glu Glu Asp
865                 870                 875                 880

Pro Tyr Leu Pro Gly Asn Pro Arg Glu Leu Ile Ala Tyr Ser Gln Tyr
                    885                 890                 895

Pro Arg Pro Ser Asp Ile Pro Gln Trp Asn Ser Asp Lys Pro Ser Leu
                    900                 905                 910

Lys Asp Ile Lys Ile Met Gly Tyr Ser Ile Arg Thr Ile Asp Tyr Arg
                    915                 920                 925

Tyr Thr Val Trp Val Gly Phe Asn Pro Asp Glu Phe Leu Ala Asn Phe
            930                 935                 940

Ser Asp Ile His Ala Gly Glu Leu Tyr Phe Val Asp Ser Asp Pro Leu
945                 950                 955                 960

Gln Asp His Asn Met Tyr Asn Asp Ser Gln Gly Gly Asp Leu Phe Gln
                    965                 970                 975

Leu Leu Met Pro
            980
```

<210> SEQ ID NO 16
<211> LENGTH: 3023
<212> TYPE: DNA
<213> ORGANISM: Artificial Sequence
<220> FEATURE:
<223> OTHER INFORMATION: Nucleotide sequence encoding amino acid
      sequence of fused protein of the heavy chain of humanized
      anti-hTfR antibody No.2 and hI2S, synthetic sequence

<400> SEQUENCE: 16

```
acgcgtgccg ccaccatggg ctggagctgg attctgctgt tcctcctgag cgtgacagca      60
ggagtgcaca gccaggtgca gctggtccag tcaggagccg aagtgaaaaa gcccggagcc     120
tcagtcaaag tgtcttgtaa agcatcaggt tatacattta cagactacgt catgcactgg     180
gtgaggcagg cacctggaca gggtctggaa tggatcggcg tgatctccac ttactatggc     240
catggaagct acaaccagag attcaagggc agggcgacaa tgactgtaga caaatcaatt     300
tccactgctt atatggagct ggtaaggctg cggtccgacg ataccgctgt gtactattgc     360
gtacgaggag atacggctc agctctctg ctggtaatt tcgatgtgtg ggggcagggt        420
accacagtca ccgtgagttc agcaagcaca aagggcccat ctgtgtttcc actggccccc     480
tccagcaaaa gcacctctgg ggtacagcc gctctgggat gtctggtgaa ggattatttc      540
ccagagccag tcaccgtgtc ctggaacagc ggagccctga catctggagt ccacactttt     600
ccagctgtgc tgcagtctag tgggctgtac tccctgtcat ccgtggtcac tgtccccagc     660
tctagtctgg gtacccagac atatatctgc aacgtgaatc acaagccatc taataccaaa     720
gtcgacaaga aagtggaacc caagtcctgt gataaaactc atacctgccc cccttgtcct     780
gcaccagagc tgctgggagg accatccgtg ttcctgtttc cacccaagcc taaagacacc     840
ctgatgatta gccgaactcc cgaagtcacc tgcgtggtcg tggacgtgtc tcacgaggac     900
cctgaagtca agtttaactg gtacgtggat ggcgtcgagg tgcataatgc taagacaaaa     960
ccccgagagg aacagtacaa cagtacatat cgtgtcgtgt cagtgctgac cgtcctgcat    1020
caggactggc tgaacgggaa ggaatataag tgcaaagtgt ccaataaggc actgccccgcc    1080
cctatcgaga aaaccattag caaggccaaa ggacagccta gggaaccaca ggtgtacaca    1140
ctgcctccat cccgggacga gctgactaag aaccaggtca gcctgacctg tctggtgaaa    1200
ggcttctatc cttcagatat cgctgtggag tgggaaagta tggacagcc agagaacaat    1260
tacaagacta ccccccctgt gctggactct gatgggagtt tctttctgta ttctaagctg    1320
accgtggata aaagtcggtg cagcagggt aatgtcttta ttgttcagt gatgcacgaa    1380
gcactgcaca accactacac ccagaaatca ctgtcactgt caccagggaa aggatcttcc    1440
gaaacgcagg ccaactcgac cacagatgct ctgaacgttc ttctcatcat cgtggatgac    1500
ctgcgcccct ccctgggctg ttatgggat aagctggtga ggtccccaaa tattgaccaa    1560
ctggcatccc acagcctcct cttccagaat gcctttgcgc agcaagcagt gtgcgccccg    1620
agccgcgttt cttcctcac tggcaggaga cctgacacca cccgcctgta cgacttcaac    1680
tcctactgga ggtgcacgc tggaaacttc tccaccatcc cccagtactt caaggagaat    1740
ggctatgtga ccatgtcggt gggaaaagtc tttcaccctg gatatcttc taaccatacc    1800
gatgattctc cgtatagctg gtcttttcca ccttatcatc cttcctctga agtatgaa    1860
aacactaaga catgtcgagg ccagatgga gaactccatg ccaacctgct ttgccctgtg    1920
gatgtgctgg atgttcccga gggcacctg cctgacaaac agagcactga gcaagccata    1980
```

```
cagttgttgg aaaagatgaa aacgtcagcc agtcctttct tcctggccgt tgggtatcat    2040
aagccacaca tccccttcag ataccccaag gaatttcaga agttgtatcc cttggagaac    2100
atcaccctgg cccccgatcc cgaggtccct gatggcctac ccctgtggc ctacaacccc     2160 tggatggaca tcaggcaacg ggaagacgtc aagccttaa acatcagtgt gccgtatggt      2220
ccaattcctg tggactttca gcggaaaatc cgccagagct actttgcctc tgtgtcatat    2280
ttggatacac aggtcggccg cctcttgagt gctttggacg atcttcagct ggccaacagc    2340
accatcattg catttacctc ggatcatggg tgggctctag gtgaacatgg agaatgggcc    2400
aaatacagca attttgatgt tgctacccat gttcccctga tattctatgt tcctggaagg    2460
acggcttcac ttccggaggc aggcgagaag cttttcccct acctcgaccc ttttgattcc    2520
gcctcacagt tgatggagcc aggcaggcaa tccatggacc ttgtggaact tgtgtctctt    2580
tttcccacgc tggctggact tgcaggactg caggttccac ctcgctgccc cgttccttca    2640
tttcacgttg agctgtgcag agaaggcaag aaccttctga agcattttcg attccgtgac    2700
ttggaagaag atccgtacct ccctggtaat ccccgtgaac tgattgccta tagccagtat    2760
ccccggcctt cagacatccc tcagtggaat tctgacaagc cgagtttaaa agatataaag    2820
atcatgggct attccatacg caccatagac tataggtata ctgtgtgggt tggcttcaat    2880
cctgatgaat tctagctaa ctttctgac atccatgcag gggaactgta ttttgtggat      2940
tctgacccat tgcaggatca caatatgtat aatgattccc aaggtggaga ccttttccag    3000
ttgttgatgc cttaagcggc cgc                                            3023
```

<210> SEQ ID NO 17
<211> LENGTH: 975
<212> TYPE: PRT
<213> ORGANISM: Artificial Sequence
<220> FEATURE:
<223> OTHER INFORMATION: Amino acid sequence of fused protein of the
      heavy chain of humanized anti-hTfR antibody No. 3 and hI2S

<400> SEQUENCE: 17

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Met Asn Tyr
            20                  25                  30

Trp Leu Gly Trp Val Arg Gln Met Pro Gly Lys Gly Leu Glu Trp Ile
        35                  40                  45

Gly Asp Ile Tyr Pro Gly Gly Asp Tyr Pro Thr Tyr Ser Glu Lys Phe
    50                  55                  60

Lys Val Lys Ala Ile Ile Ser Ala Asp Thr Ser Ile Ser Thr Val Tyr
65                  70                  75                  80

Leu Gln Leu Ser Ser Leu Lys Ala Ser Asp Thr Ala Met Tyr Phe Cys
                85                  90                  95

Ala Arg Ser Gly Asn Tyr Asp Glu Val Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175
```

```
Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200             205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
                275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
                355                 360                 365

Leu Val Lys Gly Phe Tyr Pro Ser Asp Ile Ala Val Glu Trp Glu Ser
                370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445

Gly Ser Ser Glu Thr Gln Ala Asn Ser Thr Thr Asp Ala Leu Asn Val
450                 455                 460

Leu Leu Ile Ile Val Asp Asp Leu Arg Pro Ser Leu Gly Cys Tyr Gly
465                 470                 475                 480

Asp Lys Leu Val Arg Ser Pro Asn Ile Asp Gln Leu Ala Ser His Ser
                485                 490                 495

Leu Leu Phe Gln Asn Ala Phe Ala Gln Gln Ala Val Cys Ala Pro Ser
                500                 505                 510

Arg Val Ser Phe Leu Thr Gly Arg Arg Pro Asp Thr Thr Arg Leu Tyr
                515                 520                 525

Asp Phe Asn Ser Tyr Trp Arg Val His Ala Gly Asn Phe Ser Thr Ile
                530                 535                 540

Pro Gln Tyr Phe Lys Glu Asn Gly Tyr Val Thr Met Ser Val Gly Lys
545                 550                 555                 560

Val Phe His Pro Gly Ile Ser Ser Asn His Thr Asp Asp Ser Pro Tyr
                565                 570                 575

Ser Trp Ser Phe Pro Pro Tyr His Pro Ser Ser Glu Lys Tyr Glu Asn
                580                 585                 590
```

```
Thr Lys Thr Cys Arg Gly Pro Asp Gly Glu Leu His Ala Asn Leu Leu
        595                 600                 605

Cys Pro Val Asp Val Leu Asp Val Pro Glu Gly Thr Leu Pro Asp Lys
610                 615                 620

Gln Ser Thr Glu Gln Ala Ile Gln Leu Leu Glu Lys Met Lys Thr Ser
625                 630                 635                 640

Ala Ser Pro Phe Phe Leu Ala Val Gly Tyr His Lys Pro His Ile Pro
            645                 650                 655

Phe Arg Tyr Pro Lys Glu Phe Gln Lys Leu Tyr Pro Leu Glu Asn Ile
        660                 665                 670

Thr Leu Ala Pro Asp Pro Glu Val Pro Asp Gly Leu Pro Pro Val Ala
    675                 680                 685

Tyr Asn Pro Trp Met Asp Ile Arg Gln Arg Glu Asp Val Gln Ala Leu
690                 695                 700

Asn Ile Ser Val Pro Tyr Gly Pro Ile Pro Val Asp Phe Gln Arg Lys
705                 710                 715                 720

Ile Arg Gln Ser Tyr Phe Ala Ser Val Ser Tyr Leu Asp Thr Gln Val
            725                 730                 735

Gly Arg Leu Leu Ser Ala Leu Asp Asp Leu Gln Leu Ala Asn Ser Thr
        740                 745                 750

Ile Ile Ala Phe Thr Ser Asp His Gly Trp Ala Leu Gly Glu His Gly
    755                 760                 765

Glu Trp Ala Lys Tyr Ser Asn Phe Asp Val Ala Thr His Val Pro Leu
770                 775                 780

Ile Phe Tyr Val Pro Gly Arg Thr Ala Ser Leu Pro Glu Ala Gly Glu
785                 790                 795                 800

Lys Leu Phe Pro Tyr Leu Asp Pro Phe Asp Ser Ala Ser Gln Leu Met
            805                 810                 815

Glu Pro Gly Arg Gln Ser Met Asp Leu Val Glu Leu Val Ser Leu Phe
        820                 825                 830

Pro Thr Leu Ala Gly Leu Ala Gly Leu Gln Val Pro Pro Arg Cys Pro
    835                 840                 845

Val Pro Ser Phe His Val Glu Leu Cys Arg Glu Gly Lys Asn Leu Leu
850                 855                 860

Lys His Phe Arg Phe Arg Asp Leu Glu Glu Asp Pro Tyr Leu Pro Gly
865                 870                 875                 880

Asn Pro Arg Glu Leu Ile Ala Tyr Ser Gln Tyr Pro Arg Pro Ser Asp
            885                 890                 895

Ile Pro Gln Trp Asn Ser Asp Lys Pro Ser Leu Lys Asp Ile Lys Ile
        900                 905                 910

Met Gly Tyr Ser Ile Arg Thr Ile Asp Tyr Arg Tyr Thr Val Trp Val
    915                 920                 925

Gly Phe Asn Pro Asp Glu Phe Leu Ala Asn Phe Ser Asp Ile His Ala
930                 935                 940

Gly Glu Leu Tyr Phe Val Asp Ser Asp Pro Leu Gln Asp His Asn Met
945                 950                 955                 960

Tyr Asn Asp Ser Gln Gly Gly Asp Leu Phe Gln Leu Leu Met Pro
            965                 970                 975

<210> SEQ ID NO 18
<211> LENGTH: 3008
<212> TYPE: DNA
<213> ORGANISM: Artificial Sequence
<220> FEATURE:
<223> OTHER INFORMATION: Nucleotide sequence encoding amino acid
``` sequence of fused protein of the heavy chain of humanized
anti-hTfR antibody No.3 and hI2S, synthetic sequence

<400> SEQUENCE: 18

| | |
|---|---|
| acgcgtgccg ccaccatggg ctggagctgg attctgctgt tcctcctgag cgtgacagca | 60 |
| ggagtgcaca gcgaggtgca actagtgcag tctggagcag aggtgaaaaa gcccggggag | 120 |
| tctctgaaga tcagctgtaa gggttctgga tacagcttta tgaactactg gctgggatgg | 180 |
| gtgcgccaga tgcccgggaa aggcctggag tggattgggg acatctaccc cggcggagac | 240 |
| taccctacat acagcgagaa gttcaaggtc aaggccatca tctcagccga cacgtccatc | 300 |
| agcaccgtct acctgcagtt gagcagcctg aaggcctcgg acaccgccat gtatttctgt | 360 |
| gcgagatcag gcaattacga cgaagtggcc tactggggcc aaggaaccct ggtcaccgtc | 420 |
| tcctcagcta gcaccaaggg cccatcggtc ttccccctgg cacccctctc caagagcacc | 480 |
| tctgggggca gcgcggccct gggctgcctg gtcaaggact acttccccga accggtgacg | 540 |
| gtgtcgtgga actcaggcgc cctgaccagc ggcgtgcaca ccttcccggc tgtcctacag | 600 |
| tcctcaggac tctactccct cagcagcgtg gtgaccgtgc cctccagcag cttgggcacc | 660 |
| cagacctaca tctgcaacgt gaatcacaag cccagcaaca ccaaggtgga caagaaagtt | 720 |
| gagcccaaat cttgtgacaa aactcacacg tgcccaccgt gcccagcacc tgaactcctg | 780 |
| gggggtccgt cagtcttcct cttcccccca aaacccaagg acaccctcat gatctcccgg | 840 |
| acccctgagg tcacatgcgt ggtggtggac gtgagccacg aagaccctga ggtcaagttc | 900 |
| aactggtacg tggacggcgt ggaggtgcat aatgccaaga caaagccgcg ggaggagcag | 960 |
| tacaacagca cgtaccgggt ggtcagcgtc ctcaccgtcc tgcaccagga ctggctgaat | 1020 |
| ggcaaggagt acaagtgcaa ggtctccaac aaagccctcc cagcccccat cgagaaaacc | 1080 |
| atctccaaag ccaaagggca gccccgagaa ccacaggtgt acaccctgcc cccatcccgg | 1140 |
| gatgagctga ccaagaacca ggtcagcctg acctgcctgg tcaaaggctt ctatcccagc | 1200 |
| gacatcgccg tggagtggga gagcaatggg cagccggaga caactacaa gaccacgcct | 1260 |
| cccgtgctgg actccgacgg ctccttcttc ctctacagca agctcaccgt ggacaagagc | 1320 |
| aggtggcagc aggggaacgt cttctcatgc tccgtgatgc atgaggctct gcacaaccac | 1380 |
| tacacgcaga agagcctctc cctgtctccg ggtaaaggat cttccgaaac gcaggccaac | 1440 |
| tcgaccacag atgctctgaa cgttcttctc atcatcgtgg atgacctgcg cccctccctg | 1500 |
| ggctgttatg gggataagct ggtgaggtcc ccaaatattg accaactggc atcccacagc | 1560 |
| ctcctcttcc agaatgcctt tgcgcagcaa gcagtgtgcg ccccgagccg cgtttctttc | 1620 |
| ctcactggca ggagacctga caccacccgc ctgtacgact tcaactccta ctggagggtg | 1680 |
| cacgctggaa acttctccac catccccag tacttcaagg agaatggcta tgtgaccatg | 1740 |
| tcggtgggaa aagtctttca ccctgggata tcttctaacc ataccgatga ttctccgtat | 1800 |
| agctggtctt ttccaccttta tcatccttcc tctgagaagt atgaaaacac taagacatgt | 1860 |
| cgagggccag atggagaact ccatgccaac ctgctttgcc ctgtggatgt gctggatgtt | 1920 |
| cccgagggca ccttgcctga caaacagagc actgagcaag ccatacagtt gttggaaaag | 1980 |
| atgaaaacgt cagccagtcc tttcttcctg gccgttgggt atcataagcc acacatcccc | 2040 |
| ttcagatacc caaggaatt tcagaagttg tatcccttgg agaacatcac cctggcccc | 2100 |
| gatcccgagg tcctgatgg cctacccct gtggcctaca acccctggat ggacatcagg | 2160 |
| caacgggaag acgtccaagc cttaaacatc agtgtgccgt atggtccaat tcctgtggac | 2220 |

```
tttcagcgga aaatccgcca gagctacttt gcctctgtgt catatttgga tacacaggtc    2280
ggccgcctct tgagtgcttt ggacgatctt cagctggcca acagcaccat cattgcattt    2340
acctcggatc atgggtgggc tctaggtgaa catggagaat gggccaaata cagcaatttt    2400
gatgttgcta cccatgttcc cctgatattc tatgttcctg aaggacggc ttcacttccg     2460 gaggcaggcg agaagctttt cccttacctc gacccttttg attccgcctc acagttgatg    2520
gagccaggca ggcaatccat ggaccttgtg aacttgtgt ctcttttttcc cacgctggct    2580 ggacttgcag gactgcaggt tccacctcgc tgccccgttc cttcatttca cgttgagctg    2640
tgcagagaag gcaagaacct tctgaagcat tttcgattcc gtgacttgga agaagatccg    2700
tacctccctg gtaatccccg tgaactgatt gcctatagcc agtatccccg gccttcagac    2760
atccctcagt ggaattctga caagccgagt ttaaaagata taagatcat gggctattcc     2820 atacgcacca tagactatag gtatactgtg tgggttggct tcaatcctga tgaatttcta    2880 gctaacttt ctgacatcca tgcaggggaa ctgtattttg tggattctga cccattgcag     2940
gatcacaata tgtataatga ttcccaaggt ggagaccttt tccagttgtt gatgccttaa    3000
gcggccgc                                                             3008
```

```
<210> SEQ ID NO 19
<211> LENGTH: 5
<212> TYPE: PRT
<213> ORGANISM: Artificial Sequence
<220> FEATURE:
<223> OTHER INFORMATION: Amino acid sequence of an exemplified linker 1

<400> SEQUENCE: 19

Gly Gly Gly Gly Ser
1               5

<210> SEQ ID NO 20
<211> LENGTH: 6
<212> TYPE: PRT
<213> ORGANISM: Artificial Sequence
<220> FEATURE:
<223> OTHER INFORMATION: Amino acid sequence of an exemplified linker 2

<400> SEQUENCE: 20

Gly Gly Gly Gly Gly Ser
1               5

<210> SEQ ID NO 21
<211> LENGTH: 6
<212> TYPE: PRT
<213> ORGANISM: Artificial Sequence
<220> FEATURE:
<223> OTHER INFORMATION: Amino acid sequence of an exemplified linker 3

<400> SEQUENCE: 21

Ser Gly Gly Gly Gly Gly
1               5

<210> SEQ ID NO 22
<211> LENGTH: 760
<212> TYPE: PRT
<213> ORGANISM: Homo sapiens

<400> SEQUENCE: 22

Met Met Asp Gln Ala Arg Ser Ala Phe Ser Asn Leu Phe Gly Gly Glu
1               5                   10                  15

Pro Leu Ser Tyr Thr Arg Phe Ser Leu Ala Arg Gln Val Asp Gly Asp
```

```
               20                  25                  30
Asn Ser His Val Glu Met Lys Leu Ala Val Asp Glu Glu Asn Ala
        35                  40                  45
Asp Asn Asn Thr Lys Ala Asn Val Thr Lys Pro Lys Arg Cys Ser Gly
50                  55                  60
Ser Ile Cys Tyr Gly Thr Ile Ala Val Ile Val Phe Phe Leu Ile Gly
65                  70                  75                  80
Phe Met Ile Gly Tyr Leu Gly Tyr Cys Lys Gly Val Glu Pro Lys Thr
                    85                  90                  95
Glu Cys Glu Arg Leu Ala Gly Thr Glu Ser Pro Val Arg Glu Glu Pro
                100                 105                 110
Gly Glu Asp Phe Pro Ala Ala Arg Arg Leu Tyr Trp Asp Asp Leu Lys
                115                 120                 125
Arg Lys Leu Ser Glu Lys Leu Asp Ser Thr Asp Phe Thr Gly Thr Ile
            130                 135                 140
Lys Leu Leu Asn Glu Asn Ser Tyr Val Pro Arg Glu Ala Gly Ser Gln
145                 150                 155                 160
Lys Asp Glu Asn Leu Ala Leu Tyr Val Glu Asn Gln Phe Arg Glu Phe
                165                 170                 175
Lys Leu Ser Lys Val Trp Arg Asp Gln His Phe Val Lys Ile Gln Val
                180                 185                 190
Lys Asp Ser Ala Gln Asn Ser Val Ile Ile Val Asp Lys Asn Gly Arg
                195                 200                 205
Leu Val Tyr Leu Val Glu Asn Pro Gly Gly Tyr Val Ala Tyr Ser Lys
            210                 215                 220
Ala Ala Thr Val Thr Gly Lys Leu Val His Ala Asn Phe Gly Thr Lys
225                 230                 235                 240
Lys Asp Phe Glu Asp Leu Tyr Thr Pro Val Asn Gly Ser Ile Val Ile
                245                 250                 255
Val Arg Ala Gly Lys Ile Thr Phe Ala Glu Lys Val Ala Asn Ala Glu
                260                 265                 270
Ser Leu Asn Ala Ile Gly Val Leu Ile Tyr Met Asp Gln Thr Lys Phe
            275                 280                 285
Pro Ile Val Asn Ala Glu Leu Ser Phe Phe Gly His Ala His Leu Gly
            290                 295                 300
Thr Gly Asp Pro Tyr Thr Pro Gly Phe Pro Ser Phe Asn His Thr Gln
305                 310                 315                 320
Phe Pro Pro Ser Arg Ser Ser Gly Leu Pro Asn Ile Pro Val Gln Thr
                325                 330                 335
Ile Ser Arg Ala Ala Ala Glu Lys Leu Phe Gly Asn Met Glu Gly Asp
                340                 345                 350
Cys Pro Ser Asp Trp Lys Thr Asp Ser Thr Cys Arg Met Val Thr Ser
                355                 360                 365
Glu Ser Lys Asn Val Lys Leu Thr Val Ser Asn Val Leu Lys Glu Ile
            370                 375                 380
Lys Ile Leu Asn Ile Phe Gly Val Ile Lys Gly Phe Val Glu Pro Asp
385                 390                 395                 400
His Tyr Val Val Val Gly Ala Gln Arg Asp Ala Trp Gly Pro Gly Ala
                405                 410                 415
Ala Lys Ser Gly Val Gly Thr Ala Leu Leu Leu Lys Leu Ala Gln Met
                420                 425                 430
Phe Ser Asp Met Val Leu Lys Asp Gly Phe Gln Pro Ser Arg Ser Ile
            435                 440                 445
```

```
Ile Phe Ala Ser Trp Ser Ala Gly Asp Phe Gly Ser Val Gly Ala Thr
    450                 455                 460

Glu Trp Leu Glu Gly Tyr Leu Ser Ser Leu His Leu Lys Ala Phe Thr
465                 470                 475                 480

Tyr Ile Asn Leu Asp Lys Ala Val Leu Gly Thr Ser Asn Phe Lys Val
                485                 490                 495

Ser Ala Ser Pro Leu Leu Tyr Thr Leu Ile Glu Lys Thr Met Gln Asn
            500                 505                 510

Val Lys His Pro Val Thr Gly Gln Phe Leu Tyr Gln Asp Ser Asn Trp
        515                 520                 525

Ala Ser Lys Val Glu Lys Leu Thr Leu Asp Asn Ala Ala Phe Pro Phe
    530                 535                 540

Leu Ala Tyr Ser Gly Ile Pro Ala Val Ser Phe Cys Phe Cys Glu Asp
545                 550                 555                 560

Thr Asp Tyr Pro Tyr Leu Gly Thr Thr Met Asp Thr Tyr Lys Glu Leu
                565                 570                 575

Ile Glu Arg Ile Pro Glu Leu Asn Lys Val Ala Arg Ala Ala Ala Glu
            580                 585                 590

Val Ala Gly Gln Phe Val Ile Lys Leu Thr His Asp Val Glu Leu Asn
        595                 600                 605

Leu Asp Tyr Glu Arg Tyr Asn Ser Gln Leu Leu Ser Phe Val Arg Asp
    610                 615                 620

Leu Asn Gln Tyr Arg Ala Asp Ile Lys Glu Met Gly Leu Ser Leu Gln
625                 630                 635                 640

Trp Leu Tyr Ser Ala Arg Gly Asp Phe Phe Arg Ala Thr Ser Arg Leu
                645                 650                 655

Thr Thr Asp Phe Gly Asn Ala Glu Lys Thr Asp Arg Phe Val Met Lys
            660                 665                 670

Lys Leu Asn Asp Arg Val Met Arg Val Glu Tyr His Phe Leu Ser Pro
        675                 680                 685

Tyr Val Ser Pro Lys Glu Ser Pro Phe Arg His Val Phe Trp Gly Ser
    690                 695                 700

Gly Ser His Thr Leu Pro Ala Leu Leu Glu Asn Leu Lys Leu Arg Lys
705                 710                 715                 720

Gln Asn Asn Gly Ala Phe Asn Glu Thr Leu Phe Arg Asn Gln Leu Ala
                725                 730                 735

Leu Ala Thr Trp Thr Ile Gln Gly Ala Ala Asn Ala Leu Ser Gly Asp
            740                 745                 750

Val Trp Asp Ile Asp Asn Glu Phe
    755                 760

<210> SEQ ID NO 23
<211> LENGTH: 107
<212> TYPE: PRT
<213> ORGANISM: Artificial Sequence
<220> FEATURE:
<223> OTHER INFORMATION: Amino acid sequence of the light chain variable
      region of humanized anti-hTfR antibody No.1

<400> SEQUENCE: 23

Asp Ile Gln Val Thr Gln Ser Pro Ser Phe Leu Ser Ala Ser Val Gly
1               5                   10                  15

Asp Arg Val Thr Ile Thr Cys Lys Ala Ser Gln Asp Val Asn Ser Ala
            20                  25                  30

Val Ala Trp Phe Gln Gln Lys Pro Gly Lys Ala Pro Lys Leu Leu Ile
```

```
                35                  40                  45
Tyr Trp Thr Ser Thr Arg His Thr Gly Val Pro Asp Arg Phe Ser Gly
    50                  55                  60

Ser Gly Ser Gly Thr Val Tyr Thr Leu Thr Ile Ser Ser Leu Gln Pro
65                  70                  75                  80

Glu Asp Phe Ala Thr Tyr Tyr Cys Gln Gln His Tyr Ser Thr Pro Arg
                85                  90                  95

Thr Phe Gly Gly Gly Thr Lys Val Glu Ile Lys
            100                 105
```

<210> SEQ ID NO 24
<211> LENGTH: 116
<212> TYPE: PRT
<213> ORGANISM: Artificial Sequence
<220> FEATURE:
<223> OTHER INFORMATION: Amino acid sequence of the heavy chain variable
      region of humanized anti-hTfR antibody No.1

<400> SEQUENCE: 24

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Thr Phe Ser Asn Tyr
            20                  25                  30

Gly Met Ser Trp Val Arg Gln Ala Pro Gly Lys Gly Leu Glu Leu Val
        35                  40                  45

Ala Asn Ile Asn Thr Asn Gly Gly Ser Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Thr Asn Asn Arg Tyr Asp Glu Asp Tyr Trp Gly Gln Gly Thr Leu Val
            100                 105                 110

Thr Val Ser Ser
        115
```

<210> SEQ ID NO 25
<211> LENGTH: 107
<212> TYPE: PRT
<213> ORGANISM: Artificial Sequence
<220> FEATURE:
<223> OTHER INFORMATION: Amino acid sequence of the light chain variable
      region of humanized anti-hTfR antibody No.2

<400> SEQUENCE: 25

```
Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asn Asn
            20                  25                  30

Leu Gln Trp Tyr Gln Gln Lys Pro Asp Gln Ser Pro Lys Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Leu Cys Gln Gln Ser Asn Ser Trp Pro Arg
                85                  90                  95

Thr Phe Gly Gln Gly Thr Lys Val Glu Ile Lys
            100                 105
```

<210> SEQ ID NO 26
<211> LENGTH: 120
<212> TYPE: PRT
<213> ORGANISM: Artificial Sequence
<220> FEATURE:
<223> OTHER INFORMATION: Amino acid sequence of the heavy chain variable
      region of humanized anti-hTfR antibody No.2

<400> SEQUENCE: 26

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Val Met His Trp Val Arg Gln Ala Pro Gly Gln Gly Leu Glu Trp Ile
            35                  40                  45

Gly Val Ile Ser Thr Tyr Tyr Gly His Gly Ser Tyr Asn Gln Arg Phe
    50                  55                  60

Lys Gly Arg Ala Thr Met Thr Val Asp Lys Ser Ile Ser Thr Ala Tyr
65                  70                  75                  80

Met Glu Leu Val Arg Leu Arg Ser Asp Asp Thr Ala Val Tyr Tyr Cys
                85                  90                  95

Val Arg Gly Gly Tyr Gly Ser Ser Ser Leu Ala Gly Asn Phe Asp Val
                100                 105                 110

Trp Gly Gln Gly Thr Thr Val Thr
            115                 120

<210> SEQ ID NO 27
<211> LENGTH: 112
<212> TYPE: PRT
<213> ORGANISM: Artificial Sequence
<220> FEATURE:
<223> OTHER INFORMATION: Amino acid sequence of the light chain variable
      region of humanized anti-hTfR antibody No.3

<400> SEQUENCE: 27

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
                20                  25                  30

Asn Gly Asn Thr Tyr Leu His Trp Tyr Leu Gln Lys Pro Gly Gln Ser
            35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gln Gly Thr Lys Val Glu Ile Lys
                100                 105                 110

<210> SEQ ID NO 28
<211> LENGTH: 118
<212> TYPE: PRT
<213> ORGANISM: Artificial Sequence
<220> FEATURE:
<223> OTHER INFORMATION: Amino acid sequence of the heavy chain variable
      region of humanized anti-hTfR antibody No.3

<400> SEQUENCE: 28

Glu Val Gln Leu Val Gln Ser Gly Ala Glu Val Lys Pro Gly Glu
1               5                   10                  15

Ser Leu Lys Ile Ser Cys Lys Gly Ser Gly Tyr Ser Phe Thr Asn Tyr
            20                  25                  30

Trp Leu Gly Trp Val Arg Gln Met Pro Gly Lys Gly Leu Glu Trp Met
            35                  40                  45

Gly Asp Ile Tyr Pro Gly Gly Asp Tyr Pro Thr Tyr Ser Glu Lys Phe
        50                  55                  60

Lys Val Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Gly Asn Tyr Asp Glu Val Ala Tyr Trp Gly Gln Gly Thr
            100                 105                 110

Leu Val Thr Val Ser Ser
        115

<210> SEQ ID NO 29
<211> LENGTH: 6
<212> TYPE: PRT
<213> ORGANISM: Artificial Sequence
<220> FEATURE:
<223> OTHER INFORMATION: Amino acid sequence 1 of CDR1 in the light
      chain of anti-hTfR antibody No. 1

<400> SEQUENCE: 29

Gln Asp Val Asn Ser Ala
1               5

<210> SEQ ID NO 30
<211> LENGTH: 11
<212> TYPE: PRT
<213> ORGANISM: Artificial Sequence
<220> FEATURE:
<223> OTHER INFORMATION: Amino acid sequence 2 of CDR1 in the light
      chain of anti-hTfR antibody No. 1

<400> SEQUENCE: 30

Lys Ala Ser Gln Asp Val Asn Ser Ala Val Ala
1               5                   10

<210> SEQ ID NO 31
<211> LENGTH: 6
<212> TYPE: PRT
<213> ORGANISM: Artificial Sequence
<220> FEATURE:
<223> OTHER INFORMATION: Amino acid sequence 1 of CDR2 in the light
      chain of anti-hTfR antibody No. 1

<400> SEQUENCE: 31

Trp Thr Ser Thr Arg His
1               5

<210> SEQ ID NO 32
<211> LENGTH: 7
<212> TYPE: PRT
<213> ORGANISM: Artificial Sequence
<220> FEATURE:
<223> OTHER INFORMATION: Amino acid sequence 2 of CDR2 in the light
      chain of anti-hTfR antibody No. 1

<400> SEQUENCE: 32

Trp Thr Ser Thr Arg His Thr

-continued

```
<210> SEQ ID NO 33
<211> LENGTH: 9
<212> TYPE: PRT
<213> ORGANISM: Artificial Sequence
<220> FEATURE:
<223> OTHER INFORMATION: Amino acid sequence of CDR3 in the light chain
      of anti-hTfR antibody No. 1

<400> SEQUENCE: 33

Gln Gln His Tyr Ser Thr Pro Arg Thr
1               5

<210> SEQ ID NO 34
<211> LENGTH: 5
<212> TYPE: PRT
<213> ORGANISM: Artificial Sequence
<220> FEATURE:
<223> OTHER INFORMATION: Amino acid sequence 1 of CDR1 in the heavy
      chain of anti-hTfR antibody No. 1

<400> SEQUENCE: 34

Asn Tyr Gly Met Ser
1               5

<210> SEQ ID NO 35
<211> LENGTH: 8
<212> TYPE: PRT
<213> ORGANISM: Artificial Sequence
<220> FEATURE:
<223> OTHER INFORMATION: Amino acid sequence 2 of CDR1 in the heavy
      chain of anti-hTfR antibody No. 1

<400> SEQUENCE: 35

Gly Leu Thr Phe Ser Asn Tyr Gly
1               5

<210> SEQ ID NO 36
<211> LENGTH: 8
<212> TYPE: PRT
<213> ORGANISM: Artificial Sequence
<220> FEATURE:
<223> OTHER INFORMATION: Amino acid sequence 1 of CDR2 in the heavy
      chain of anti-hTfR antibody No. 1

<400> SEQUENCE: 36

Ile Asn Thr Asn Gly Gly Ser Thr
1               5

<210> SEQ ID NO 37
<211> LENGTH: 17
<212> TYPE: PRT
<213> ORGANISM: Artificial Sequence
<220> FEATURE:
<223> OTHER INFORMATION: Amino acid sequence 2 of CDR2 in the heavy
      chain of anti-hTfR antibody No. 1

<400> SEQUENCE: 37

Asn Ile Asn Thr Asn Gly Gly Ser Thr Tyr Tyr Pro Asp Ser Val Lys
1               5                   10                  15

Gly

<210> SEQ ID NO 38
<211> LENGTH: 7
<212> TYPE: PRT
<213> ORGANISM: Artificial Sequence
```

```
<220> FEATURE:
<223> OTHER INFORMATION: Amino acid sequence 1 of CDR3 in the heavy
      chain of anti-hTfR antibody No. 1

<400> SEQUENCE: 38

Asn Arg Tyr Asp Glu Asp Tyr
1               5

<210> SEQ ID NO 39
<211> LENGTH: 9
<212> TYPE: PRT
<213> ORGANISM: Artificial Sequence
<220> FEATURE:
<223> OTHER INFORMATION: Amino acid sequence 2 of CDR3 in the heavy
      chain of anti-hTfR antibody No. 1

<400> SEQUENCE: 39

Thr Asn Asn Arg Tyr Asp Glu Asp Tyr
1               5

<210> SEQ ID NO 40
<211> LENGTH: 6
<212> TYPE: PRT
<213> ORGANISM: Artificial Sequence
<220> FEATURE:
<223> OTHER INFORMATION: Amino acid sequence 1 of CDR1 in the light
      chain of anti-hTfR antibody No. 2

<400> SEQUENCE: 40

Gln Ser Ile Ser Asn Asn
1               5

<210> SEQ ID NO 41
<211> LENGTH: 11
<212> TYPE: PRT
<213> ORGANISM: Artificial Sequence
<220> FEATURE:
<223> OTHER INFORMATION: Amino acid sequence 2 of CDR1 in the light
      chain of anti-hTfR antibody No. 2

<400> SEQUENCE: 41

Arg Ala Ser Gln Ser Ile Ser Asn Asn Leu Gln
1               5                   10

<210> SEQ ID NO 42
<211> LENGTH: 6
<212> TYPE: PRT
<213> ORGANISM: Artificial Sequence
<220> FEATURE:
<223> OTHER INFORMATION: Amino acid sequence 1 of CDR2 in the light
      chain of anti-hTfR antibody No. 2

<400> SEQUENCE: 42

Tyr Ala Ser Gln Ser Ile
1               5

<210> SEQ ID NO 43
<211> LENGTH: 7
<212> TYPE: PRT
<213> ORGANISM: Artificial Sequence
<220> FEATURE:
<223> OTHER INFORMATION: Amino acid sequence 2 of CDR2 in the light
      chain of anti-hTfR antibody No. 2

<400> SEQUENCE: 43

Tyr Ala Ser Gln Ser Ile Ser
1               5
```

<210> SEQ ID NO 44
<211> LENGTH: 9
<212> TYPE: PRT
<213> ORGANISM: Artificial Sequence
<220> FEATURE:
<223> OTHER INFORMATION: Amino acid sequence of CDR3 in the light chain
      of anti-hTfR antibody No. 2

<400> SEQUENCE: 44

Gln Gln Ser Asn Ser Trp Pro Arg Thr
1               5

<210> SEQ ID NO 45
<211> LENGTH: 5
<212> TYPE: PRT
<213> ORGANISM: Artificial Sequence
<220> FEATURE:
<223> OTHER INFORMATION: Amino acid sequence 1 of CDR1 in the heavy
      chain of anti-hTfR antibody No. 2

<400> SEQUENCE: 45

Asp Tyr Val Met His
1               5

<210> SEQ ID NO 46
<211> LENGTH: 8
<212> TYPE: PRT
<213> ORGANISM: Artificial Sequence
<220> FEATURE:
<223> OTHER INFORMATION: Amino acid sequence 2 of CDR1 in the heavy
      chain of anti-hTfR antibody No. 2

<400> SEQUENCE: 46

Gly Tyr Thr Phe Thr Asp Tyr Val
1               5

<210> SEQ ID NO 47
<211> LENGTH: 8
<212> TYPE: PRT
<213> ORGANISM: Artificial Sequence
<220> FEATURE:
<223> OTHER INFORMATION: Amino acid sequence 1 of CDR2 in the heavy
      chain of anti-hTfR antibody No. 2

<400> SEQUENCE: 47

Ile Ser Thr Tyr Tyr Gly His Gly
1               5

<210> SEQ ID NO 48
<211> LENGTH: 17
<212> TYPE: PRT
<213> ORGANISM: Artificial Sequence
<220> FEATURE:
<223> OTHER INFORMATION: Amino acid sequence 2 of CDR2 in the heavy
      chain of anti-hTfR antibody No. 2

<400> SEQUENCE: 48

Val Ile Ser Thr Tyr Tyr Gly His Gly Ser Tyr Asn Gln Arg Phe Lys
1               5                   10                  15

Gly

<210> SEQ ID NO 49
<211> LENGTH: 14
<212> TYPE: PRT
<213> ORGANISM: Artificial Sequence
<220> FEATURE:
<223> OTHER INFORMATION: Amino acid sequence 1 of CDR3 in the heavy chain of anti-hTfR antibody No. 2

<400> SEQUENCE: 49

Gly Gly Tyr Gly Ser Ser Ser Leu Ala Gly Asn Phe Asp Val
1               5                   10

<210> SEQ ID NO 50
<211> LENGTH: 16
<212> TYPE: PRT
<213> ORGANISM: Artificial Sequence
<220> FEATURE:
<223> OTHER INFORMATION: Amino acid sequence 2 of CDR3 in the heavy
      chain of anti-hTfR antibody No. 2

<400> SEQUENCE: 50

Val Arg Gly Gly Tyr Gly Ser Ser Ser Leu Ala Gly Asn Phe Asp Val
1               5                   10                  15

<210> SEQ ID NO 51
<211> LENGTH: 11
<212> TYPE: PRT
<213> ORGANISM: Artificial Sequence
<220> FEATURE:
<223> OTHER INFORMATION: Amino acid sequence 1 of CDR1 in the light
      chain of anti-hTfR antibody No. 3

<400> SEQUENCE: 51

Gln Ser Leu Val His Ser Asn Gly Asn Thr Tyr
1               5                   10

<210> SEQ ID NO 52
<211> LENGTH: 16
<212> TYPE: PRT
<213> ORGANISM: Artificial Sequence
<220> FEATURE:
<223> OTHER INFORMATION: Amino acid sequence 2 of CDR1 in the light
      chain of anti-hTfR antibody No. 3

<400> SEQUENCE: 52

Arg Ser Ser Gln Ser Leu Val His Ser Asn Gly Asn Thr Tyr Leu His
1               5                   10                  15

<210> SEQ ID NO 53
<211> LENGTH: 6
<212> TYPE: PRT
<213> ORGANISM: Artificial Sequence
<220> FEATURE:
<223> OTHER INFORMATION: Amino acid sequence 1 of CDR2 in the light
      chain of anti-hTfR antibody No. 3

<400> SEQUENCE: 53

Lys Val Ser Asn Arg Phe
1               5

<210> SEQ ID NO 54
<211> LENGTH: 7
<212> TYPE: PRT
<213> ORGANISM: Artificial Sequence
<220> FEATURE:
<223> OTHER INFORMATION: Amino acid sequence 2 of CDR2 in the light
      chain of anti-hTfR antibody No. 3

<400> SEQUENCE: 54

Lys Val Ser Asn Arg Phe Ser
1               5

<210> SEQ ID NO 55

```
<211> LENGTH: 9
<212> TYPE: PRT
<213> ORGANISM: Artificial Sequence
<220> FEATURE:
<223> OTHER INFORMATION: Amino acid sequence of CDR3 in the light chain
      of anti-hTfR antibody No. 3

<400> SEQUENCE: 55

Ser Gln Ser Thr His Val Pro Trp Thr
1               5

<210> SEQ ID NO 56
<211> LENGTH: 5
<212> TYPE: PRT
<213> ORGANISM: Artificial Sequence
<220> FEATURE:
<223> OTHER INFORMATION: Amino acid sequence 1 of CDR1 in the heavy
      chain of anti-hTfR antibody No. 3

<400> SEQUENCE: 56

Asn Tyr Trp Leu Gly
1               5

<210> SEQ ID NO 57
<211> LENGTH: 8
<212> TYPE: PRT
<213> ORGANISM: Artificial Sequence
<220> FEATURE:
<223> OTHER INFORMATION: Amino acid sequence 2 of CDR1 in the heavy
      chain of anti-hTfR antibody No. 3

<400> SEQUENCE: 57

Gly Tyr Ser Phe Thr Asn Tyr Trp
1               5

<210> SEQ ID NO 58
<211> LENGTH: 8
<212> TYPE: PRT
<213> ORGANISM: Artificial Sequence
<220> FEATURE:
<223> OTHER INFORMATION: Amino acid sequence 1 of CDR2 in the heavy
      chain of anti-hTfR antibody No. 3

<400> SEQUENCE: 58

Ile Tyr Pro Gly Gly Asp Tyr Pro
1               5

<210> SEQ ID NO 59
<211> LENGTH: 17
<212> TYPE: PRT
<213> ORGANISM: Artificial Sequence
<220> FEATURE:
<223> OTHER INFORMATION: Amino acid sequence 2 of CDR2 in the heavy
      chain of anti-hTfR antibody No. 3

<400> SEQUENCE: 59

Asp Ile Tyr Pro Gly Gly Asp Tyr Pro Thr Tyr Ser Glu Lys Phe Lys
1               5                   10                  15

Val

<210> SEQ ID NO 60
<211> LENGTH: 9
<212> TYPE: PRT
<213> ORGANISM: Artificial Sequence
<220> FEATURE:
<223> OTHER INFORMATION: Amino acid sequence 1 of CDR3 in the heavy
      chain of anti-hTfR antibody No. 3
```

```
<400> SEQUENCE: 60

Ser Gly Asn Tyr Asp Glu Val Ala Tyr
1               5

<210> SEQ ID NO 61
<211> LENGTH: 11
<212> TYPE: PRT
<213> ORGANISM: Artificial Sequence
<220> FEATURE:
<223> OTHER INFORMATION: Amino acid sequence 2 of CDR3 in the heavy
      chain of anti-hTfR antibody No. 3

<400> SEQUENCE: 61

Ala Arg Ser Gly Asn Tyr Asp Glu Val Ala Tyr
1               5                   10
```

LYOPHILIZED PREPARATION

SEQUENCE LISTING SUBMISSION VIA EFS-WEB

A computer readable text file, entitled "SequenceListing.txt," created on or about Jun. 27, 2019 with a file size of about 86 kb contains the sequence listing for this application and is hereby incorporated by reference in its entirety.

TECHNICAL FIELD

The present invention relates to a storage stable lyophilized formulation containing a protein, in which an antibody and a lysosomal enzyme are combined, as an active ingredient, and more particularly, to the lyophilized formulation containing sucrose and a nonionic surfactant as a stabilizing agent.

BACKGROUND ART

Proteins in which an antibody is combined with a lysosomal enzyme have been reported to be produced, such as a fusion protein between an anti-insulin receptor antibody and α-L-iduronidase (Patent Document 1), and a fusion protein between an anti-insulin receptor antibody and iduronate-2-sulfatase (Patent Document 2). In the formulation of such artificially constructed novel proteins, it is unknown what forms are preferable for their formulation.

Regarding the formulation of antibodies, many reports have been reported, including a lyophilized formulation containing anti-IL-13 antibody as an active ingredient (Patent Document 3), a lyophilized formulation of an antibody containing amino acids such as arginine, histidine, and lysine or their salts (Patent Document 4), a lyophilized formulation of an antibody containing meglumine (Patent Document 5), a lyophilized formulation of an anti-EGF receptor antibody containing lactobionic acid (Patent Document 6), and a lyophilized formulation of an anti-human IL-23p19 antibody containing citric acid, polysorbate 80, and sucrose (Patent Document 7). That is to say, even if thinking about only antibodies, current situation is that trial and error is required when formulating their formulations.

CITATION LIST

Patent Literature

[Patent Document 1] JP 2010-534723
[Patent Document 2] JP 2012-521194
[Patent Document 3] JP 2016-519124
[Patent Document 4] WO 2007/074880
[Patent Document 5] WO 2006/132363
[Patent Document 6] JP 2009-540015
[Patent Document 7] JP 2012-501332

SUMMARY OF INVENTION

Problems to be Solved by the Invention

An object of the present invention is to provide a lyophilized formulation comprising, as an active ingredient, a protein in which an antibody and a lysosomal enzyme are bound to each other, and as stabilizing agents, sucrose and a nonionic surfactant, that formulation is stable enough to permit its distribution to the market.

Means for Solving the Problems

In a study for the above-mentioned object, the inventors found that a protein in which an antibody and a human iduronate-2 sulfatase, one of human lysosomal enzymes, are combined can be stably stored in the form of a lyophilized formulation containing sucrose and a nonionic surfactant as excipients. Thus the present invention includes the following.

(1) A lyophilized formulation comprising;
a fusion protein including an antibody and a lysosomal enzyme, as an active ingredient, and further
a neutral salt, a disaccharide, a nonionic surfactant, and a buffer.

(2) The lyophilized formulation according to 1 above, wherein the neutral salt is sodium chloride.

(3) The lyophilized formulation according to 1 or 2 above, wherein the disaccharide is selected from the group consisting of trehalose, sucrose, maltose, and lactose.

(4) The lyophilized formulation according to any one of 1 to 3 above, wherein the nonionic surfactant is polysorbate or poloxamer.

(5) The lyophilized formulation according to any one of 1 to 3 above, wherein the nonionic surfactant is selected from the group consisting of polysorbate 20, polysorbate 80, and polyoxyethylene(160)polyoxypropylene(30)glycol.

(6) The lyophilized formulation according to any one of 1 to 5 above, wherein the buffer is a phosphate buffer.

(7) The lyophilized formulation according to 1 or 2 above, wherein the disaccharide is sucrose, the nonionic surfactant is polyoxyethylene(160)polyoxypropylene(30)glycol, and the buffer is a phosphate buffer.

(8) The lyophilized formulation according to any one of 1 to 7 above, wherein the amounts of the neutral salt, the disaccharide, and the ionic surfactant are 0.015 to 2.5 (w/w), 2.5 to 200 (w/w), and 0.005 to 6 (w/w), respectively, relative to the amount of the fusion protein.

(9) The lyophilized formulation according to any one of 1 to 7 above, wherein the amounts of the neutral salt, the disaccharide, and the ionic surfactant are 0.05 to 0.5 (w/w), 5 to 50 (w/w), and 0.02 to 0.2 (w/w), respectively, relative to the amount of the fusion protein.

(10) The lyophilized formulation according to any one of 1 to 7 above, wherein the amounts of the neutral salt, the disaccharide, and the ionic surfactant is 0.1 to 0.25 (w/w), 10 to 25 (w/w), and 0.04 to 0.1 (w/w), respectively, relative to the amount of the fusion protein.

(11) The lyophilized formulation according to any one of 1 to 10 above, wherein the pH is 5.5 to 7.5 when dissolved in pure water.

(12) The lyophilized formulation according to any one of 1 to 11 above, wherein the fusion protein is a fusion protein in which human lysosomal enzyme is linked to the light chain or the heavy chain of the antibody on the C-terminal side or the N-terminal side thereof by a peptide bond.

(13) The lyophilized formulation according to any one of 1 to 11 above, wherein the fusion protein is a fusion protein in which human lysosomal enzyme is linked to the heavy chain of the antibody on the C-terminal side thereof by a peptide bond.

(14) The lyophilized formulation according to any one of 1 to 11 above, wherein the fusion protein is a fusion protein in which human lysosomal enzyme is linked to the light chain or the heavy chain of the antibody on the C-terminal side or the N-terminal side thereof via a linker including one or more amino acids.

(15) The lyophilized formulation according to any one of 1 to 11 above, wherein the fusion protein is a fusion protein in which human lysosomal enzyme is linked to the heavy chain of the antibody on the C-terminal side thereof via a linker including one or more of amino acids.

(16) The lyophilized formulation according to 14 or 15 above, wherein the linker includes the amino acid sequence of Gly-Ser.

(17) The lyophilized formulation according to any one of 1 to 16 above, wherein the lysosomal enzyme is a human lysosomal enzyme.

(18) The lyophilized formulation according to any one of 1 to 17 above, wherein the lysosomal enzyme is selected from the group consisting of α-L-iduronidase, iduronate-2-sulfatase, glucocerebrosidase, β-galactosidase, GM2 activator protein, β-hexosaminidase A, β-hexosaminidase B, N-acetylglucosamine-1-phosphotransferase, α-mannosidase, β-mannosidase, galactosylceramidase, saposin C, arylsulfatase A, α-L-fucosidase, aspartyl glucosaminidase, α-N-acetylgalactosaminidase, acid sphingomyelinase, α-galactosidase, β-glucuronidase, heparan N-sulfatase, α-N-acetylglucosaminidase, acetyl-CoA:α-glucosaminide N-acetyltransferase, N-acetylglucosamine-6-sulfatase, acid ceramidase, amylo-1,6-glucosidase, sialidase, aspartylglucosaminidase, palmitoyl-protein thioesterase 1, tripeptidyl-peptidase 1, hyaluronidase 1, CLN1, and CLN2.

(19) The lyophilized formulation according to 17 above, wherein the human lysosomal enzyme is human iduronate-2-sulfatase.

(20) The lyophilized formulation according to any one of 1 to 19 above, wherein the antibody is a human antibody or a humanized antibody.

(21) The lyophilized formulation according to any one of 1 to 20 above, wherein the antibody recognizes a molecule present on the surface of a vascular endothelial cell as an antigen.

(22) The lyophilized formulation according to 21 above, wherein the vascular endothelial cells are human vascular endothelial cells.

(23) The lyophilized formulation according to 21 or 22 above, wherein the vascular endothelial cells are cerebral vascular endothelial cells.

(24) The lyophilized formulation according to 23 above, wherein the molecule present on the surface of the cerebral vascular endothelial cell is selected from the group consisting of transferrin receptor (TfR), insulin receptor, leptin receptor, lipoprotein receptor, IGF receptor, OATP-F, organic anion transporter, MCT-8 and monocarboxylate transporter.

(25) The lyophilized formulation according to 20 above, wherein the antibody is a humanized anti-human transferrin receptor (hTfR) antibody.

(26) The lyophilized formulation according to 20 above, wherein the antibody is a humanized anti-hTfR antibody, wherein the human lysosomal enzyme is human iduronate-2-sulfatase, wherein the fusion protein comprises the humanized anti-hTfR antibody and the human iduronate-2-sulfatase, and wherein the fusion protein is selected from the group consisting of (a) to (c) below;

(a) the fusion protein, wherein the light chain of the humanized anti-hTfR antibody has the amino acid sequence set forth as SEQ ID NO:2, and wherein the heavy chain of the humanized anti-hTfR antibody having the amino acid sequence set forth as SEQ ID NO:8 is linked, on the C-terminal side thereof, to the human iduronate-2-sulfatase via a linker sequence, (b) the fusion protein, wherein the light chain of the humanized anti-hTfR antibody has the amino acid sequence set forth as SEQ ID NO:4, and wherein the heavy chain of the humanized anti-hTfR antibody having the amino acid sequence set forth as SEQ ID NO:9 is linked, on the C-terminal side thereof, to the human iduronate-2-sulfatase via a linker sequence, and (c) the fusion protein, wherein the light chain of the humanized anti-hTfR antibody has the amino acid sequence set forth as SEQ ID NO:6, and wherein the heavy chain of the humanized anti-hTfR antibody having the amino acid sequence set forth as SEQ ID NO:10 is linked, on the C-terminal side thereof, to the human iduronate-2-sulfatase via a linker sequence.

(27) The lyophilized formulation according to 20 above, wherein the antibody is a humanized anti-hTfR antibody, wherein the human lysosomal enzyme is human iduronate-2-sulfatase, wherein the fusion protein comprises the humanized anti-hTfR antibody and the human iduronate-2-sulfatase, and wherein the fusion protein is selected from the group consisting of (a) to (c) below;

(a) the fusion protein, wherein the light chain of the humanized anti-hTfR antibody has the amino acid sequence set forth as SEQ ID NO:2, and wherein the heavy chain of the humanized anti-hTfR antibody is linked, on the C-terminal side thereof and via a linker sequence of Gly-Ser, to the human iduronate-2-sulfatase, and the whole linked heavy chain has the amino acid sequence set forth as SEQ ID NO:13, (b) the fusion protein, wherein the light chain of the humanized anti-hTfR antibody has the amino acid sequence set forth as SEQ ID NO:4, and wherein the heavy chain of the humanized anti-hTfR antibody is linked, on the C-terminal side thereof and via a linker sequence of Gly-Ser, to the human iduronate-2-sulfatase, and the whole linked heavy chain has the amino acid sequence set forth as SEQ ID NO:15, and (c) the fusion protein, wherein the light chain of the humanized anti-hTfR antibody has the amino acid sequence set forth as SEQ ID NO:6, and wherein the heavy chain of the humanized anti-hTfR antibody is linked, on the C-terminal side thereof and via a linker sequence of Gly-Ser, to the human iduronate-2-sulfatase, and the whole linked heavy chain has the amino acid sequence set forth as SEQ ID NO:17.

(28) The lyophilized formulation according to any one of 1 to 27 above, sealed in a container formed of a borosilicate glass or a hydrophobic resin.

(29) The lyophilized formulation according to 28 above, wherein the container is formed by a cycloolefin copolymer, a ring-opened polymer of cycloolefin, or a hydrogenated ring-opened polymer of cycloolefin.

Effects of the Invention

According to the present invention, a fusion protein in which an antibody and a lysosomal enzyme are combined can be stabilized as a lyophilized formulation to such an extent that it can be distributed on the market.

EMBODIMENTS FOR CARRYING OUT THE INVENTION

The present invention relates to a pharmaceutical composition which is stable in storage in a lyophilized state and contains, as an active ingredient, a protein in which an antibody and a lysosomal enzyme are combined. Here, the antibody to be combined with the lysosomal enzyme is preferably a human antibody or a humanized antibody, but insofar as the antibody has the property of specifically binding to the antigen, there is no particular restriction on the animal species of the antibody. For example, the antibody may be a non-human mammalian antibody or chimeric antibody between a human antibody and non-human mammalian antibody.

The term "human antibody" refers to an antibody whose entirety is encoded by a gene originating from human. The term "human antibody", however, also includes an antibody encoded by a gene obtained by introducing a mutation into an original human gene for a purpose of enhancing expression efficiency of the gene. The term "human antibody" also includes an antibody which is produced by combining two or more genes encoding human antibodies and replacing a certain part of a human antibody with a part of another human antibody. The same can apply to humanized antibodies described below.

Human antibodies, in principle, have three complementarity determining regions (CDR) in the variable region of immunoglobulin light chain and three complementarity determining regions (CDR) in the variable region of immunoglobulin heavy chain. The three CDRs of the immunoglobulin light chain are designated CDR1, CDR2, and CDR3 in order from the N-terminal side. The three CDRs of the immunoglobulin heavy chain are called CDR1, CDR2 and CDR3 in order from the N-terminal side. An antibody is also a human antibody in which one of CDR of the human antibody is replaced with a CDR of another human antibody to change its antigen specificity, affinity, and so on. The same applies to humanized antibodies described below.

Both the heavy chain and light chain variable regions of an antibody, in principle, comprise four framework regions 1 to 4 (FR1 to FR4). FR1 is a region adjacent to CDR1 on the N-terminal side thereof, and consists of an amino acid sequence from the N-terminus in each peptide constituting the heavy chain and the light chain to an amino acid adjacent to the N-terminus of CDR1 thereof. FR2 consists of an amino acid sequence between CDR1 and CDR2 in each peptide constituting the heavy chain and the light chain. FR3 consists of an amino acid sequence between CDR2 and CDR3 in each peptide constituting the heavy chain and the light chain. FR4 consists of an amino acid sequence from an amino acid adjacent to the C-terminus of CDR3 to the C-terminus of the variable region. However, in the present invention, which is not limited thereby, a region excluding 1 to 5 N-terminal side amino acids and/or 1 to 5 C-terminal side amino acids in each FR region described above may be defined as the framework region. The same applies to humanized antibodies described below.

In the present invention, the term "human antibody" also includes an antibody which is produced through modification of the gene of the original human antibody by introducing a mutation, such as substitution, deletion, addition, to the amino acid sequence of the original antibody. When replacing one or more amino acids of the amino acid sequence of the original antibody with other amino acids, the number of amino acid replaced may preferably be 1 to 20, more preferably 1 to 5, and still more preferably 1 to 3. When deleting one or more amino acids of the amino acid sequence of the original antibody, the number of amino acids deleted may preferably be 1 to 20, more preferably 1 to 5, and still more preferably 1 to 3. An antibody produced by a combined mutation of these substitution and deletion of amino acids is also a "human antibody". When adding one or more amino acids, preferably 1 to 20, more preferably 1 to 5, and still more preferably 1 to 3 amino acids may be added inside the amino acid sequence of the original antibody or on its N- or C-terminus. An antibody produced by a combined mutation of addition, substitution, and deletion of amino acids is also a "human antibody". The amino acid sequence of such a mutated antibody has a homology of preferably not lower than 80%, more preferably not lower than 90%, still more preferably not lower than 95%, and even more preferably not lower than 98%, to the amino acid sequence of the original antibody. Thus, in the present invention, the term "gene originating from human" includes not only the unmutated gene originating from human but also a gene produced by modifying it. The same applies to humanized antibodies described below.

For example, when a mutation is added to the light chain of humanized anti-hTfR antibody No. 1 set forth as SEQ ID NO:2, the light chain of humanized anti-hTfR antibody No. 2 set forth as SEQ ID NO:4, and the light chain of humanized anti-hTfR antibody No. 3 set forth as SEQ ID NO:6, the rules shown above apply. The above rules also apply when a mutation is added to the heavy chain of humanized anti-hTfR antibody No. 1 set forth as SEQ ID NO:8, the heavy chain of humanized anti-hTfR antibody No. 2 set forth as SEQ ID NO:9, and the heavy chain of humanized anti-hTfR antibody No. 3 set forth as SEQ ID NO:10.

When introducing mutation into the gene encoding the whole or part of the light chain variable region of the original human antibody, the gene thus mutated has a homology that is preferably not lower than 80%, more preferably not lower than 90%, to the original gene, though there is no particular limitation as to the level of homology. When replacing one or more amino acids of the amino acid sequence of the light chain variable region with other amino acids, the number of amino acids to be replaced is preferably 1 to 10, more preferably 1 to 5, still more preferably 1 to 3, and even more preferably 1 or 2. When deleting one or more amino acids of the amino acid sequence of the light chain variable region, the number of amino acids to be deleted is preferably 1 to 10, more preferably 1 to 5, still more preferably 1 to 3, even more preferably 1 or 2. A combined mutation of these substitution and deletion of amino acids can also be carried out. When adding one or more amino acid to the light chain variable region, they may be added inside, or on the N-terminal side or C-terminal side of, the amino acid sequence of the light chain variable region, and the number of amino acids added is preferably 1 to 10, more preferably 1 to 5, still more preferably 1 to 3, and even more preferably 1 or 2. A combined mutation of these addition, substitution, and deletion of amino acids can also be carried out. The amino acid sequence of the light chain variable region thus mutated has a homology that is preferably not lower than 80%, more preferably not lower than 90%, still more preferably not lower than 95% to the amino acid sequence of the original light chain variable region. In particular, when replacing one or more amino acids of the amino acid sequence of CDR with other amino acids, the number of amino acid replaced is preferably 1 to 5, more preferable 1 to 3, still more preferably 1 or 2. When deleting one or more amino acid of the amino acid sequence of CDR, the number of amino acids to be deleted is preferably 1 to 5, more preferably 1 to 3, still more preferably 1 or 2. A combined mutation of these substitution and deletion of the amino acid can also be carried out. When adding one or more amino acids, they may be added inside, or on the N-terminal side or C-terminal side of, the amino acid sequence, and the number of amino acids added is preferably 1 to 5, more preferably 1 to 3, still more preferably 1 or 2.

A combined mutation of these addition, substitution, and deletion of amino acids can also be carried out. The amino acid sequence of respective mutated CDR has a homology that is preferably not lower than 80%, more preferably not lower than 90%, and still more preferably not lower than 95% to the amino acid sequence of the original CDR. The same applied to humanized antibodies described below.

For example, the above rules apply when a mutation is added to the variable region of the light chain of humanized anti-hTfR antibody No. 1 set forth as SEQ ID NO:23, to the variable region of the light chain of humanized anti-hTfR antibody No. 2 set forth as SEQ ID NO:25, or to the variable region of the light chain of humanized anti-hTfR antibody No. 3 set forth as SEQ ID NO:27.

The variable region of the light chain set forth as SEQ ID NO:23 contains the amino acid sequence of SEQ ID NO:29 or 30 in CDR1, contains the amino acid sequence of SEQ ID NO:31 or 32 in CDR2, and contains the amino acid sequence of SEQ ID NO:33 in CDR3. The variable region of the light chain set forth as SEQ ID NO:25 contains the amino acid sequence of SEQ ID NO:40 or 41 in CDR1, contains the amino acid sequence of SEQ ID NO:42 or 43 in CDR2, and contains the amino acid sequence of SEQ ID NO:44 in CDR3. The variable region of the light chain set forth as SEQ ID NO:27 contains the amino acid sequence of SEQ ID NO:51 or 52 in CDR1, contains the amino acid sequence of SEQ ID NO:53 or 54 in CDR2, and contains the amino acid sequence of SEQ ID NO: 55 in CDR3. When a mutation is added to these CDRs, the above rules apply.

When introducing mutation into the gene encoding the whole or part of the heavy chain variable region of the original human antibody, the gene thus mutated has a homology that is preferably not lower than 80%, more preferably not lower than 90%, to the original gene, though there is no particular limitation as to the level of homology. When replacing one or more amino acids of the amino acid sequence of the heavy chain variable region with other amino acids, the number of amino acids to be replaced is preferably 1 to 10, more preferably 1 to 5, still more preferably 1 to 3, and even more preferably 1 or 2. When deleting one or more amino acids of the amino acid sequence of the heavy chain variable region, the number of amino acids to be deleted is preferably 1 to 10, more preferably 1 to 5, still more preferably 1 to 3, even more preferably 1 or 2. A combined mutation of these substitution and deletion of amino acids can also be carried out. When adding one or more amino acid to the heavy chain variable region, they may be added inside, or on the N-terminal side or C-terminal side of, the amino acid sequence of the heavy chain variable region, and the number of amino acids added is preferably 1 to 10, more preferably 1 to 5, still more preferably 1 to 3, and even more preferably 1 or 2. A combined mutation of these addition, substitution, and deletion of amino acids can also be carried out. The amino acid sequence of the heavy chain variable region thus mutated has a homology that is preferably not lower than 80%, more preferably not lower than 90%, still more preferably not lower than 95% to the amino acid sequence of the original heavy chain variable region. In particular, when replacing one or more amino acids of the amino acid sequence of CDR with other amino acids, the number of amino acid replaced is preferably 1 to 5, more preferable 1 to 3, still more preferably 1 or 2. When deleting one or more amino acid of the amino acid sequence of CDR, the number of amino acids to be deleted is preferably 1 to 5, more preferably 1 to 3, still more preferably 1 or 2. A combined mutation of these substitution and deletion of the amino acid can also be carried out. When adding one or more amino acids, they may be added inside, or on the N-terminal side or C-terminal side of, the amino acid sequence, and the number of amino acids added is preferably 1 to 5, more preferably 1 to 3, still more preferably 1 or 2. A combined mutation of these addition, substitution, and deletion of amino acids can also be carried out. The amino acid sequence of respective mutated CDR has a homology that is preferably not lower than 80%, more preferably not lower than 90%, and still more preferably not lower than 95% to the amino acid sequence of the original CDR. The same applied to humanized antibodies described below.

For example, the above rules apply when a mutation is added to the variable region of the heavy chain of humanized anti-hTfR antibody No. 1 set forth as SEQ ID NO:24, the variable region of the heavy chain of humanized anti-hTfR antibody No. 2 set forth as SEQ ID NO:26, and the variable region of the heavy chain of humanized anti-hTfR antibody No. 3 set forth as SEQ ID NO:28.

The variable region of the heavy chain represented by SEQ ID NO:24 contains the amino acid sequence of SEQ ID NO:34 or 35 in CDR1, contains the amino acid sequence of SEQ ID NO:36 or 37 in CDR2, and contains the amino acid sequence of SEQ ID NO:38 or 39 in CDR3. The variable region of the heavy chain represented by SEQ ID NO:26 contains the amino acid sequence of SEQ ID NO:45 or 46 in CDR1, contains the amino acid sequence of SEQ ID NO:47 or 48 in CDR2, and contains the amino acid sequence of SEQ ID NO:49 or 50 in CDR3. The variable region of the heavy chain represented by SEQ ID NO:28 contains the amino acid sequence of SEQ ID NO:56 or 57 in CDR1, contains the amino acid sequence of SEQ ID NO:58 or 59 in CDR2, and contains the amino acid sequence of SEQ ID NO:60 or 61 in CDR3. When a mutation is added to these CDRs, the above rules apply.

In the present invention, "homology" means the ratio (%) of homologous amino acid residues to total amino acid residues in the optimal alignment when two amino acid sequences are compared using a homology calculation algorithm. It has been well known in the art of the invention to compare the two amino acid sequences by a homology shown by such a ratio and may be readily understood by those skilled in the art.

The substitution of an amino acid in the amino acid sequence of the light chain and the heavy chain of the anti-hTfR antibody by another amino acid, for example, include the substitution by an amino acid classified in the same group, such as aromatic amino acids (Phe, Trp, Tyr), aliphatic amino acids (Ala, Leu, Ile, Val), polar amino acids (Gln, Asn), basic amino acids (Lys, Arg, His), acidic amino acids (Glu, Asp), amino acid with hydroxyl groups (Ser, Thr), and amino acids with small side chains (Gly, Ala, Ser, Thr, Met). Substitution by such similar amino acids is predicted to cause no change in the protein phenotype (i.e., conservative amino acid substitutions). Examples of such conservative amino acid substitutions are well known in the art and are described in various literatures (e.g., Bowie et al, Science, 247: 1306-1310 (1990)).

In the present invention, as a homology calculation algorithm for calculating homology between the amino acid sequence of the original protein (including an antibody) and the amino acid sequence of the mutated protein, BLAST (Altschul SF. J Mol. Biol. 215. 403-10 (1990)), Pearson and Lipman's similar searching method (Proc. Natl. Acad. Sci. USA. 85. 2444 (1988)), Smith and Waterman's local homology algorithm (Adv. Appl. Math. 2. 482-9 (1981)), and so on have been well known. Further, blastp, one of the BLAST programs provided on the Internet by the National Institutes of Health, has been well known as a means to calculate the homology of two amino acid sequences.

In the present invention, the term "humanized antibody" refers to an antibody in which part of the amino acid sequence of its variable region (e.g., especially the whole or part of its CDRs) originates from a non-human mammal while the rest originates from human. An example of humanized antibody is an antibody produced by replacing the three complementarity determining regions (CDRs) of the light chain of the immunoglobulin and the three complementarity determining regions (CDRs) of the heavy chain of the immunoglobulin constituting a human antibody, with CDRs from a non-human mammal. There is no particular limitation as to the biological species from which those CDRs grafted into a proper position of the human antibody originate, insofar as it originates from a non-human mammal. Though the species are preferably mouse, rat, rabbit, horse or non-human primate, and more preferably mouse or rat, for example mouse.

In the present invention, the term "chimeric antibody" refers to an antibody produced by connecting fragments of two or more different antibodies originating from two or more different species.

A chimeric antibody comprising a human antibody and a non-human mammalian antibody is an antibody provided by replacing part of a human antibody with part of a non-human mammalian antibody. As explained below, an antibody is made of an Fc region, a Fab region and a hinge region. A specific example of such chimeric antibodies is a chimeric antibody whose Fc region originates from a human antibody while its Fab region originates from a non-human mammalian antibody. The hinge region either originates from a human antibody or from a non-human mammalian antibody. On the contrary, the term chimeric antibody also includes one whose Fc region originates from a non-human mammalian antibody while its Fab region originates from a human antibody. In such a case also, the hinge region either originates from a human antibody or from a non-human mammalian antibody.

An antibody can be viewed as composed of a variable region and a constant region. Additional examples of chimeric antibodies include an antibody in which the heavy chain constant region ($C_H$) and the light chain constant region ($C_1$) both originate from a human antibody while the heavy chain variable region ($V_H$) and the light chain variable region ($V_L$) both originate from an antibody of a non-human mammal, and conversely, an antibody in which the heavy chain constant region ($C_H$) and the light chain constant region ($C_1$) both originate from an antibody of a non-human mammal, while the heavy chain variable region ($V_H$) and the light chain variable region ($V_L$) both originate from a human antibody. In these, there is no particular limitation as to the biological species of the non-human mammal, insofar as it is a non-human mammal, though the species are preferably mouse, rat, rabbit, horse or non-human primate, more preferably mouse.

A chimeric antibody comprising a human antibody and a mouse antibody is designated in particular "human/mouse chimeric antibody". Examples of human/mouse chimeric antibodies include a chimeric antibody in which the Fc region originates from a human antibody while the Fab region originates from a mouse antibody, and conversely, a chimeric antibody whose Fc region originates from mouse antibody, while its Fab region originates from a human antibody. A hinge region either originates from a human antibody or a mouse antibody. Additional specific examples of human/mouse chimeric antibodies include those whose heavy chain constant region ($C_H$) and light chain constant region ($C_1$) originate from a human antibody while its heavy chain variable region ($V_H$) and light chain variable region ($V_L$) originate from a mouse antibody, and conversely, those whose heavy chain constant region ($C_H$) and light chain constant region ($C_1$) originate from a mouse antibody while its heavy chain variable region ($V_H$) and light chain variable region ($V_L$) originate from a human antibody.

Originally, an antibody is of the basic structure having four polypeptide chains in total, consisting of two immunoglobulin light chains and two immunoglobulin heavy chains. However, in the present invention the term "antibody" refers, besides to an antibody having this basic structure, also to;

(1) one consisting of two polypeptide chains comprising a single immunoglobulin light chain and a single immunoglobulin heavy chain, and, as explained later, (2) a single-chain antibody consisting of an immunoglobulin light chain which is linked, on the C-terminal side thereof, to a linker sequence which in turn is linked, on the C-terminal side thereof, to an immunoglobulin heavy chain, (3) single-chain antibodies consisting of an immunoglobulin heavy chain which is linked, on the C-terminal side thereof, to a linker sequence which in turn is linked, on the C-terminal side thereof, to an immunoglobulin light chain, and (4) one consisting of a Fab region, i.e., a structure left behind by removal of the Fc region from an antibody having the basic structure as the original meaning, and one consisting of the Fab region and the whole or part of the hinge region (including Fab, F(ab'), and F(ab')$_2$). Furthermore, scFv in which the variable region of the light chain and the variable region of the heavy chain are linked via a linker sequence to form a single chain antibody is also included in the antibody of the present invention.

Here, the term "Fab" refers to a molecule consisting of a single light chain comprising the variable region and the $C_L$ region (light chain constant region) and a single heavy chain comprising the variable region and the $C_H1$ region (portion 1 of heavy chain constant region) which are combined by a disulfide bond between their respective cysteine residues. While the heavy chain in a Fab can include part of the hinge region in addition to the variable region and the $C_H1$ region (portion 1 of heavy chain constant region), the hinge region in such a case lacks the cysteine residue that otherwise is present in the hinge region and would serve to link two heavy chains of an antibody together. In Fab, the light chain and the heavy chain are connected by a disulfide bond formed between the cysteine residue present in the light chain constant region ($C_L$ region) and the cysteine residue located in the heavy chain constant region ($C_H1$ region) or the hinge region. The heavy chain composing Fab is referred to as "Fab heavy chain". As it lacks the cysteine residue in the hinge region which serves to bind two heavy chains of an antibody, Fab consists of a single light chain and a single heavy chain. The light chain constituting Fab includes a variable region and a $C_L$ region. The heavy chain as a component of Fab may either consist of a variable region and a $C_H1$ region or also of part of the hinge region in addition to the variable region and the $C_H1$ region. However, in this case, the hinge region is so selected as not to include the cysteine residue that could bind two heavy chains, in order to avoid the formation of a disulfide bond between two heavy chains at their hinge regions. In F(ab'), the heavy chain includes, in addition to a variable region and a $C_H1$ region, the whole or part of a hinge region containing a cysteine residue that could bind two heavy chains. F(ab')$_2$ is a molecule consisting of two F(ab')s bound together through a disulfide bond formed between the cysteine residues present in their respective hinge regions. The heavy chain composing F(ab') or F(ab')$_2$ is referred to as "Fab' heavy chain". Further, a polymer such as a dimer and a trimer, which consists of two or more antibodies connected with each other, directly or via a linker, is also included in the term "antibody". Moreover, in addition to the aforementioned, any molecule that includes part of an immunoglobulin molecule and has a property to specifically bind to the antigen is also included in the term "antibody" in the present invention. Thus, in the present invention, the term "immunoglobulin light chain" includes a molecule that is derived from an original immunoglobulin light chain and having the amino acid sequence of the whole or part of its variable region. Likewise, the term "immunoglobulin heavy chain" includes a molecule that is derived from an original immunoglobulin heavy chain and having the amino acid sequence of the whole or part of its variable region. Therefore, insofar as having the whole or part of the amino acid sequence of the variable region, a molecule is included in the term "immunoglobulin heavy chain", even if it lacks its Fc region, for example.

Also, in the above, the term "Fc" or "Fc region" refers to a region comprising a fragment consisting of $C_H2$ region (portion 2 of the heavy chain constant region), and $C_H3$ region (portion 3 of the heavy chain constant region) in the antibody molecule.

Furthermore, in the present invention, the term "antibody" also includes:

(5) scFab, scF(ab'), and scF(ab')$_2$, which are single-chain antibodies produced by binding the light chain to the heavy chain that form, respectively, the Fab, F(ab') and F(ab')$_2$ mentioned in (4) above, via a linker sequence. Such scFab, scF(ab') and scF(ab')$_2$ may be a molecule in which either the light chain is linked, on the C-terminal side thereof, to a linker sequence, which in turn is linked, on the C-terminal side thereof, to the heavy chain, or the heavy chain is linked, on the C-terminal side thereof, to a linker sequence, which in turn is linked, on the C-terminal side thereof, to the light chain. Furthermore, a scFv, which is a single-chain antibody provided by binding the light chain variable region to the heavy chain variable region, via a linker sequence between them, is also included in the term "antibody" in the present invention. Such scFv may be a molecule in which either the light chain variable region is linked, on the C-terminal side thereof, to a linker sequence, which in turn is linked, on the C-terminal side thereof, to the heavy chain variable region, or the heavy chain variable region is linked, on the C-terminal side thereof, to a linker sequence, which in turn is linked, on the C-terminal side thereof, to the light chain variable region.

In the present invention, the term "single-chain antibody" refers to a protein in which an amino acid sequence comprising the whole or part of an immunoglobulin light chain variable region linked, on the C-terminal side thereof, to a linker sequence, which in turn is linked, on the C-terminal side thereof, to the amino acid sequence of the whole or part of an immunoglobulin heavy chain variable region, and having an ability to specifically bind a certain antigen. For example, those shown in (2), (3), and (5) above are included in the single-chain antibody. Further, a protein in which an amino acid sequence comprising the whole or part of an immunoglobulin heavy chain variable region is linked, on the C-terminal side thereof, to a linker sequence, which in turn is further linked, on the C-terminal side thereof, to the amino acid sequence of the whole or part of an immunoglobulin light chain variable region, and which has an ability to specifically bind to a certain antigen, is also included in the term "single-chain antibody" in the present invention. In a single-chain antibody in which an immunoglobulin heavy chain is linked, on the C-terminal side thereof and via a linker sequence, to an immunoglobulin light chain, the immunoglobulin heavy chain generally lacks the Fc region. An immunoglobulin light chain variable region has three complementarity determining regions (CDRs) which participate in determining the antigen specificity of an antibody. Likewise, an immunoglobulin heavy chain variable region also has three CDRs. Those CDRs are the primary regions that determine the antigen specificity of an antibody. Therefore, a single-chain antibody preferably contains all the three CDRs of the immunoglobulin heavy chain and all the three CDRs of the immunoglobulin light chain. However, it is also possible to provide a single-chain antibody in which one or more of those CDRs are deleted, insofar as the antigen-specific affinity of the antibody is retained.

In a single-chain antibody, the linker sequence placed between the light chain and the heavy chain of the immunoglobulin is a peptide chain consisting of preferably 2 to 50, more preferably 8 to 50, still more preferably 10 to 30, even more preferably 12 to 18, or 15 to 25, for example 15 or 25 amino acid residues. While there is no particular limitation as to the specific amino acid sequence of such a linker sequence insofar as the anti-hTfR antibody comprising the both chains linked thereby retains the affinity to hTfR, it is preferably made of glycine only, or of glycine and serine. For example, there are the amino acid sequence Gly-Ser, the amino acid sequence Gly-Gly-Ser, the amino acid sequence Gly-Gly-Gly, the amino acid sequence Gly-Gly-Gly-Gly-Ser (SEQ ID NO:19), the amino acid sequence Gly-Gly-Gly-Gly-Gly-Ser (SEQ ID NO:20), the amino acid sequence Ser-Gly-Gly-Gly-Gly (SEQ ID NO:21), or a sequence which includes a sequence corresponding to 2 to 10 or 2 to 5 of any of those amino acid sequences consecutively linked. For example, in linking the amino acid sequence of the entire immunoglobulin heavy chain variable region on the C-terminal side thereof and via a linker sequence, to immunoglobulin light chain variable region to produce ScFV, a preferable linker sequence comprises a linker sequence consisting of a total of 15 amino acids corresponding to three of the amino acid sequence Gly-Gly-Gly-Gly-Ser (SEQ ID NO: 19) consecutively linked.

In the present invention, the antigen specifically recognized by the antibody is, for example, a molecule present on the surface of vascular endothelial cells (surface antigen). Examples of such surface antigens include transferrin receptor (TfR), insulin receptor, leptin receptor, lipoprotein receptor, IGF receptor, organic anion transporters such as OATP-F, monocarboxylic acid transporters such as MCT-8, Fc receptors, and the like, but are not limited to these. Antigens are preferably these molecules (surface antigens) present on the surface of human vascular endothelial cells.

Among the surface antigens described above, transferrin receptor (TfR), insulin receptor, leptin receptor, lipoprotein receptor, IGF receptor, organic anion transporters such as OATP-F, and monocarboxylic acid transporter such as MCT-8 are present on the surface of brain capillary endothelial cells forming the blood brain barrier (Blood Brain Barrier). Antibodies capable of recognizing these antigens can bind to brain capillary endothelial cells (cerebral vascular endothelial cells) via antigens. And antibodies bound to brain capillary endothelial cells can cross the blood brain barrier and reach the central nervous system. Therefore, by binding the protein of interest to such an antibody, it is possible to reach the central nervous system. Protein of interest may be a protein having a function to exert a drug effect in the central nervous system. For example, lysosomal enzymes that are deficient or dysfunctional in lysosomal disease patients with central nervous system disorders are included in the proteins of interest. Such a lysosomal enzyme cannot reach the central nervous system as it is and does not show a drug effect against a central nervous system disorder of a patient, but by allowing it to bind with these antibodies, it can pass through the blood brain barrier, as a result, the central nervous system disorder found in lysosomal disease patients can be improved.

In the present invention, the term "human transferrin receptor" or "hTfR" refers to a membrane protein having the amino acid sequence set forth as SEQ ID NO:22. The anti-hTfR antibody of the present invention is, in one of its embodiments, that which binds to the region from the cysteine residue at the position 89th from the N-terminus to the phenylalanine at the C-terminus in the amino acid sequence set forth as SEQ ID NO:22 (the extracellular region of hTfR), though it is not limited to this embodiment.

A method for preparing an antibody is described below, an antibody against hTfR taken as an example. For preparation of an antibody to hTfR, there is known a general method according to which a recombinant human transferrin receptor (rhTfR) is produced using cells which have an introduced expression vector having an incorporated hTfR gene, and then animals such as mice are immunized with this rhTfR. By collecting those cells which produce antibodies to hTfR from the immunized animals and fusing them with myeloma cells, hybridoma cells can be obtained having an ability to produce the anti-hTfR antibody.

Further, cells producing an antibody to hTfR can also be obtained by collecting immunocompetent cells from an animal such as mouse, and immunizing them with rhTfR by in vitro immunization. In conducting immunization by in vitro immunization, there is no particular limitation as to the animal species from which the immunocompetent cells are derived, though preferred are mouse, rat, rabbit, guinea pig, dog, cat, horse, and primates including human, and more preferred are mouse, rat and human, and still more preferably mouse and human. As mouse immunocompetent cells, spleen cells prepared from mouse spleen may be used, for example. As human immunocompetent cells, such cells can be used as prepared from human peripheral blood, bone marrow, spleen, and the like. By immunizing human immunocompetent cells according to in vitro immunization, a human antibody to hTfR can be obtained.

In the present invention, while there is no particular limitation as to the human lysosomal enzyme to be linked to the antibody, such lysosomal enzymes include α-L-iduronidase (IDUA), iduronate-2-sulfatase (IDS or I2S), glucocerebrosidase (GBA), β-galactosidase, GM2 activator protein, β-hexosaminidase A, β-hexosaminidase B, N-acetylglucosamine-1-phosphotransferase, α-mannosidase (LAMAN), β-mannosidase, galactosylceramidase (GALC), saposin C, arylsulfatase A (ARSA), α-L-fucosidase (FUCA1), aspartyl glucosaminidase, α-N-acetylgalactosaminidase, acid sphingomyelinase (ASM), α-galactosidase, β-Glucuronidase (GUSB), heparan N-sulfatase (SGSH), α-N-acetylglucosaminidase (NAGLU), acetyl-CoA:α-glucosaminide N-acetyltransferase, N-acetylglucosamine-6-sulfatase, acid ceramidase (AC), amylo-1,6-glucosidase, sialidase, aspartylglucosaminidase, palmitoyl-protein thioesterase 1 (PPT-1), tripeptidyl-peptidase 1 (TPP-1), hyaluronidase 1, acid α-glucosidase (GAA), CLN1, CLN2, and a like.

When the antibody specifically recognizes a molecule present on the surface of the vascular endothelial cell (surface antigen), the human lysosomal enzyme linked to the antibody can be used as a therapeutic agent for central nervous system disorders, i.e. α-L-iduronidase (IDUA) as a therapeutic agent for central nervous system disorders in Hurler syndrome or Hurler-Scheie syndrome; iduronate-2-sulfatase (IDS) as a therapeutic agent for central nervous system disorders in Hunter syndrome; glucocerebrosidase (GBA) as a therapeutic agent for central nervous system disorders in Gaucher's disease; β-galactosidase as a therapeutic agent for central nervous system disorders in GM1 gangliosidosis Types 1 to 3; GM2 activator protein as a therapeutic agent for central nervous system disorders in GM2-gangliosidosis AB variant; β-hexosaminidase A as a therapeutic agent for central nervous system disorders in Sandhoff's disease and Tay-Sachs disease; β-hexosaminidase B as a therapeutic agent for central nervous system disorders in Sandhoff's disease; N-acetylglucosamine-1-phosphotransferase as a therapeutic agent for central nervous system disorders in I-cell disease; α-mannosidase (LAMAN) as a therapeutic agent for central nervous system disorders in α-mannosidosis; β-mannosidase as a therapeutic agent for central nervous system disorders in β-mannosidosis; galactosylceramidase (GALC) as a therapeutic agent for central nervous system disorders in Krabbe disease; saposin C as a therapeutic agent for central nervous system disorders in Gaucher's disease-like storage disease; arylsulfatase A (ARSA) as a therapeutic agent for central nervous system disorders in metachromatic white matter degeneration (metachromatic leukodystrophy); α-L-fucosidase (FUCA1) as a therapeutic agent for central nervous system disorders in fucosidosis; aspartylglucosaminidase as a therapeutic agent for central nervous system disorders in aspartylglucosaminuria; α-N-acetylgalactosaminidase as a therapeutic agent for central nervous system disorders in Schindler disease and Kawasaki disease; acidic sphingomyelinase (ASM) as a therapeutic agent for central nervous system disorders in Niemann-Pick disease; α-galactosidase as a therapeutic agent for central nervous system disorders in Fabry disease; β-glucuronidase (GUSB) as a therapeutic agent for central nervous system disorders in Sly syndrome; heparan N-sulfatase (SGSH), α-N-acetylglucosaminidase (NAGLU), acetyl CoA:α-glucosaminide N-acetyltransferase and N-acetylglucosamine-6-sulfatase as therapeutic agents for central nervous system disorders in Sanfilippo syndrome; acid ceramidase (AC) as a therapeutic agent for central nervous system disorders in Farber disease; amylo-1,6-glucosidase as a therapeutic agent for central nervous system disorders in Cori's disease (Forbes-Cori's disease); sialidase as a therapeutic agent for central nervous system disorders in sialidase deficiency; aspartylglucosaminidase as a therapeutic agent for central nervous system disorders in aspartylglucosaminuria; palmitoyl-protein thioesterase 1 (PPT-1) as a therapeutic agent for central nervous system disorders in neuronal ceroid lipofuscinosis or Santavuori-Haltia disease; tripeptidyl-peptidase 1 (TPP-1) as a therapeutic agent for central nervous system disorders in neuronal ceroid lipofuscinosis or Jansky-Bielschowsky disease; hyaluronidase 1 as a therapeutic agent for central nervous system disorders in hyaluronidase deficiency; acid α-glucosidase (GAA) as a therapeutic agent for Pompe disease; CLN1 and CLN2 as therapeutic agents for central nervous system disorders in Batten disease.

In the case where the antibody specifically recognizes a molecule present on the surface of vascular endothelial cells (surface antigen), lysosomal enzymes to be preferably linked to the antibody include human iduronate-2-sulfatase (hI2S). I2S is one of lysosome enzyme having an activity for hydrolyzing sulfate bonds present in glycosaminoglycan (GAG) molecules such as heparan sulfate and dermatan sulfate. Hunter syndrome is a genetic disorder in which this enzyme is congenitally deleted. In the patients of Hunter syndrome, heparan sulfate and dermatan sulfate accumulate in the tissues, resulting in various symptoms such as corneal opacity, mental development delay, and so on. However, in the mild cases, mental developmental delay may not be observed. Therefore, since the fusion protein comprising the antibody and hI2S can degrade GAG accumulated in brain tissues by passing through BBB, it can be used as a therapeutic agent for central nervous system disorders by administered to a patient with Hunter syndrome showing mental developmental delay. Further it may be prophylactically administered to the patients of Hunter syndrome not showing mental development delay.

In the present invention, the term "human I2S" or "hI2S" refers to hI2S particularly having the same amino acid sequence as wild type hI2S. The wild type hI2S has an amino acid sequence consisting of 525 amino acids set forth as SEQ ID NO: 1. However, not limited to this, a hI2S containing a mutation such as substitution, deletion, addition and so on added to the amino acid sequence of the wild type hI2S is also included in hI2S, insofar as it has I2S activity. When one or more amino acids of the amino acid sequence of hI2S are substituted with other amino acids, the number of amino acids to be substituted is preferably 1 to 10, more preferably 1 to 5, still more preferably 1 to 3, and even still more preferably 1 to 2. When one or more amino acids in the amino acid sequence of hI2S are deleted, the number of amino acids to be deleted is preferably 1 to 10, more preferably 1 to 5, still more preferably 1 to 3, and even still more preferably 1 to 2. A combined mutation of these substitution and deletion of amino acids can also be carried out. When adding one or more amino acids to the hI2S, they may be added inside, or on the N-terminal side or C-terminal side thereof, and the number of amino acids added is preferably 1 to 10, more preferably 1 to 5, still more preferably 1 to 3, and even more preferably 1 or 2. A combined mutation of these addition, substitution, and deletion of amino acids can also be carried out. The amino acid sequence of such a mutated hI2S has a homology of preferably not lower than 80%, more preferably not lower than 90%, still more preferably not lower than 95%, and even still more preferably not lower than 98% to the amino acid sequence of the original hI2S.

In the present invention, the statement that hI2S has the I2S activity means that the hI2S fused to an antibody to form a fusion protein has an activity not lower than 3% of the activity that the natural-type hI2S intrinsically has. However, the activity is preferably not lower than 10%, more preferably not lower than 20%, still more preferably not lower than 50%, even more preferably not lower than 80% of the activity that the natural-type hI2S intrinsically has. The same also applies when the I2S has one or more of mutations. The antibody is, for example, an anti-hTfR antibody.

In the present invention, the term "fusion protein" refers to a substance obtained by binding an antibody and a human lysosomal enzyme directly, or via a non-peptide linker or a peptide linker. Methods for conjugating antibodies and human lysosomal enzymes are described in detail below.

For binding an antibody to a lysosomal enzyme, a method is available to bind them together via a non-peptide linker or a peptide linker. As non-peptide linkers, there can be used, biotin-streptavidin, polyethylene glycol, polypropylene glycol, copolymer of ethylene glycol and propylene glycol, polyoxyethylated polyol, polyvinyl alcohol, polysaccharides, dextran, polyvinyl ether, biodegradable polymer, polymerized lipid, chitins, and hyaluronic acid, or derivatives thereof, or combinations thereof. A peptide linker is a peptide chain consisting of 1 to 50 amino acids linked by peptide bonds or a derivative thereof, whose N-terminus and C-terminus are to be covalently linked either to the antibody or the lysosomal enzyme, respectively, to bind the antibody to the human lysosomal enzyme.

When biotin-streptavidin is used as the non-peptide linker, the antibody and the human lysosomal enzyme may be linked to each other via binding between biotin and streptavidin, where the antibody is bound to the biotin, and the human lysosomal enzyme is bound to the streptavidin. Conversely, the antibody and the human lysosomal enzyme may be bound to each other via binding between biotin and streptavidin, where the antibody is bound to the streptavidin, and the human lysosomal enzyme is bound to the biotin. Biotin and streptavidin can be bound to proteins by well-known methods.

In particular, a conjugate which is formed by binding the antibody of the present invention to human lysosomal enzyme via PEG as a non-peptide linker, is designated "antibody-PEG-human lysosomal enzyme". The antibody-PEG-human lysosomal enzyme can be prepared by first binding the antibody to PEG to form antibody-PEG, and then binding the antibody-PEG to the human lysosomal enzyme. Alternatively, an antibody-PEG-human lysosomal enzyme can be prepared by first binding the human lysosomal enzyme to PEG to form "human lysosomal enzyme-PEG", and then binding the "human lysosomal enzyme-PEG" to the antibody. In order to bind PEG to the antibody and the human lysosomal enzyme, a PEG is employed which is modified with such functional groups as carbonate, carbonylimidazole, active ester of carboxylic acid, azlactone, cyclic imide thione, isocyanate, isothiocyanate, imidate, aldehyde or the like. Such functional groups introduced to PEG react mainly with amino groups in the antibody and the human lysosomal enzyme to covalently bind PEG to the antibody and the human lysosomal enzyme. Though there is no particular limitation as to the molecular weight and the configuration of PEG employed here, its mean molecular weight (MW) is as follows: preferably MW=300 to 60000, more preferably MW=500 to 20000. For example, such PEG whose mean molecular weight is about 300, about 500, about 1000, about 2000, about 4000, about 10000, about 20000, and the like is preferably used as a non-peptide linker.

For example, "antibody-PEG" can be prepared by mixing the antibody with a polyethylene glycol having aldehyde groups as functional groups (ALD-PEG-ALD) so that the molar ratio of ALD-PEG-ALD to the antibody is 11, 12.5, 15, 110, 120 and the like, and then adding to the mixture a reducing agent such as $NaCNBH_3$ to let a reaction take place. Then, by reacting "antibody-PEG" with a human lysosomal enzyme in the presence of a reducing agent such as $NaCNBH_3$, "antibody-PEG-human lysosomal enzyme" is obtained. On the contrary, it is also possible to obtain "antibody-PEG-human lysosomal enzyme" by first binding a human lysosomal enzyme to ALD-PEG-ALD to prepare "human lysosomal enzyme-PEG", and then binding the "human lysosomal enzyme-PEG" to the antibody.

The antibody and a human lysosomal enzyme can also be bound together through peptide bonds by linking the antibody heavy chain or light chain, on the C-terminal side or the N-terminal side thereof, either via a linker sequence or directly, to the N-terminus or the C-terminus of the human lysosomal enzyme, respectively. Thus the fusion protein comprising the antibody and a human lysosomal enzyme can be obtained by incorporating into an expression vector for eukaryotes such as mammalian cells and yeast a DNA fragment in which a cDNA encoding the human lysosomal enzyme is placed in-frame directly, or via a DNA fragment encoding a linker sequence, on the 3'-end or 5'-end side of a cDNA encoding the heavy chain or light chain of the antibody, and culturing mammalian cells into which the above expression vector has been introduced. Where the DNA fragment encoding a human lysosomal enzyme is linked to the heavy chain, a mammalian expression vector in which a cDNA fragment encoding the antibody light chain is also introduced into the same host cells, whereas if DNA fragment encoding a human lysosomal enzyme is linked to the light chain, a mammalian expression vector in which a cDNA fragment encoding the antibody heavy chain is also incorporated into the same host cells. In the case where the antibody is a single-chain antibody, the fusion protein comprising the antibody and a human lysosomal enzyme combined can be obtained by incorporating into an expression vector for eukaryotic cells such as mammalian cells and yeast, a DNA fragment which is formed by linking the cDNA encoding a human lysosomal enzyme, on the 5'-end side or on the 3'-end side thereof, directly or via a DNA fragment encoding a linker sequence, to the cDNA encoding the single-chain antibody, and allowing the fusion protein be expressed in those cells into which the expression vector has been introduced.

In a fusion protein of the type in which a human lysosomal enzyme is linked to the antibody light chain on the C-terminal side thereof, the antibody comprises an amino acid sequence including the whole or part of the light chain variable region and an amino acid sequence including the whole or part of the heavy chain variable region, and the human lysosomal enzyme is linked to the light chain of this antibody on the C-terminal side thereof. Here, the antibody light chain and a human lysosomal enzyme may be linked together, directly or via a linker.

In a fusion protein of the type in which a human lysosomal enzyme is linked to the antibody heavy chain on the C-terminal side thereof, the antibody comprises an amino acid sequence including the whole or part of the light chain variable region and an amino acid sequence including the whole or part of the heavy chain variable region, and the human lysosomal enzyme is linked to the heavy chain of this antibody on the C-terminal side thereof. Here, the antibody heavy chain and a human lysosomal enzyme may be linked together, directly or via a linker.

In a fusion protein of the type in which a human lysosomal enzyme is linked to the antibody light chain on the N-terminal side thereof, the antibody comprises an amino acid sequence including the whole or part of the light chain variable region and an amino acid sequence including the whole or part of the heavy chain variable region, and the human lysosomal enzyme is linked to the light chain of this antibody on the N-terminal side thereof. Here, the antibody light chain and a human lysosomal enzyme may be linked together, directly or via a linker.

In a fusion protein of the type in which a human lysosomal enzyme is linked to the antibody heavy chain on the N-terminal side thereof, the antibody comprises an amino acid sequence including the whole or part of the light chain variable region and an amino acid sequence including the whole or part of the heavy chain variable region, and the human lysosomal enzyme is linked to the heavy chain of this antibody on the N-terminal side thereof. Here, the antibody heavy chain and a human lysosomal enzyme may be linked together, directly or via a linker.

In the above, when the linker sequence is placed between the antibody and a human lysosomal enzyme, the linker sequence may consist of preferably of 1 to 50, more preferably of 1 to 17, still more preferably of 1 to 10, even more preferably of 1 to 5 amino acids, and in accordance with the human lysosomal enzyme to be linked to the antibody, the number of amino acids of the linker sequence may be adjusted to 1, 2, 3, 1 to 17, 1 to 10, 10 to 40, 20 to 34, 23 to 31, 25 to 29, etc., as desired. Though there is no particular limitation as to amino acid sequence of the linker sequence insofar as the antibody linked by it retains the affinity to hTfR and a human lysosomal enzyme linked by the linker sequence also exhibits the protein's own physiological activity under a physiological condition, the linker may preferably be composed of glycine and serine. Examples of such linkers include one consisting of a single amino acid either glycine or serine, the amino acid sequence Gly-Ser, the amino acid sequence Gly-Gly-Ser, the amino acid sequence Gly-Gly-Gly-Gly-Ser (SEQ ID NO:19), the amino acid sequence Gly-Gly-Gly-Gly-Gly-Ser (SEQ ID NO:20), the amino acid sequence Ser-Gly-Gly-Gly-Gly (SEQ ID NO:21), or a sequence which includes 1 to 10 or 2 to 5 of any of those amino acid sequences consecutively linked to consist of 1 to 50, 2 to 17, 2 to 10, 10 to 40, 20 to 34, 23 to 31, or 25 to 29 amino acids. For example, those comprising the amino acid sequence Gly-Ser may preferably be used as linker sequences. Same can be applied when the antibody is a single chain antibody.

Besides, in the present invention, when a peptide chain includes a plurality of linker sequences, each of those linker sequences is designated, from the N-terminal side, the first linker sequence, the second linker sequence, and so on, for convenience.

Preferred embodiments of the antibody, that antibody is a humanized antibody and an anti-human transferrin receptor antibody, include the following (x) to (z) below, (X) the light chain comprises the amino acid sequence set forth as SEQ ID NO: 2, and the heavy chain comprises the amino acid sequence set forth as SEQ ID NO: 8;

(Y) the light chain comprises the amino acid sequence set forth as SEQ ID NO: 4, and the heavy chain comprises the amino acid sequence set forth as SEQ ID NO: 9;

(Z) the light chain comprises the amino acid sequence set forth as SEQ ID NO: 6, and the heavy chain comprises the amino acid sequence set forth as SEQ ID NO: 10.

Here, (x), (y) and (z) correspond to a humanized anti-hTfR antibody No. 1, a humanized anti-hTfR antibody No. 2, and a humanized anti-hTfR antibody No. 3, respectively, that antibodies are described in the examples.

However, preferred embodiments of the antibody are not limited to the (x) to (z) above, when the antibody is a humanized antibody and an anti-human transferrin receptor antibody. For example, the antibody can be used in the present invention, whose amino acid sequence of the light chain has a homology not lower than 80% to the amino acid sequence of each one of light chain in the above (x) to (z), and whose amino acid sequence of the heavy chain has a homology not lower than 80% to the amino acid sequence of each one of heavy chain in the above (x) to (z) insofar as that antibody has affinity for hTfR. Further, the antibody can be used in the present invention, whose amino acid sequence of the light chain has a homology not lower than 90% to the amino acid sequence of each one of light chain in the above (x) to (z), and whose amino acid sequence of the heavy chain has a homology not lower than 90% to the amino acid sequence of each one of heavy chain in the above (x) to (z) insofar as that antibody has affinity for hTfR. Further, the antibody can be used in the present invention, whose amino acid sequence of the light chain has a homology not lower than 95% to the amino acid sequence of each one of light chain in the above (x) to (z), and whose amino acid sequence of the heavy chain has a homology not lower than 95% to the amino acid sequence of each one of heavy chain in the above (x) to (z) insofar as that antibody has affinity for hTfR.

Further, the antibody can be used in the present invention, which has in the light chain the amino acid sequence corresponding to the amino acid sequence introduced 1 to 10 of amino acid substitution, deletion, or addition in each one of the amino acid sequence of the light chain set forth in (x) to (z) above, and/or has in the heavy chain the amino acid sequence corresponding to the amino acid sequence introduced 1 to 10 of amino acid substitution, deletion, or addition in each one of the amino acid sequence of the heavy chain set forth in (x) to (z) above, insofar as it has an affinity for hTfR. Further, the antibody can be used in the present invention, which has in the light chain the amino acid sequence corresponding to the amino acid sequence introduced 1 to 5 of amino acid substitution, deletion, or addition in each one of the amino acid sequence of the light chain set forth in (x) to (z) above, and has in the heavy chain the amino acid sequence corresponding to the amino acid sequence introduced 1 to 5 of amino acid substitution, deletion, or addition in each one of the amino acid sequence of the heavy chain set forth in (x) to (z) above, insofar as it has an affinity for hTfR. Further, the antibody can be used in the present invention, which has in the light chain the amino acid sequence corresponding to the amino acid sequence introduced 1 to 3 of amino acid substitution, deletion, or addition in each one of the amino acid sequence of the light chain set forth in (x) to (z) above, and has in the heavy chain the amino acid sequence corresponding to the amino acid sequence introduced 1 to 3 of amino acid substitution, deletion, or addition in each one of the amino acid sequence of the heavy chain set forth in (x) to (z) above, insofar as it has an affinity for hTfR.

In the above preferred embodiment (x) of the antibody, the amino acid sequence set forth as SEQ ID NO: 23 corresponds to a variable region in the amino acid sequence of the light chain set forth as SEQ ID NO: 2, and the amino acid sequence set forth as SEQ ID NO: 24 corresponds to a variable region in the amino acid sequence of the heavy chain set forth as SEQ ID NO: 8. In the above preferred embodiment (y) of the antibody, the amino acid sequence set forth as SEQ ID NO: 25 corresponds to a variable region in the amino acid sequence of the light chain set forth as SEQ ID NO: 4, and the amino acid sequence set forth as SEQ ID NO: 26 corresponds to a variable region in the amino acid sequence of the heavy chain set forth as SEQ ID NO: 9. In the above preferred embodiment (z) of the antibody, the amino acid sequence set forth as SEQ ID NO: 27 corresponds to a variable region in the amino acid sequence of the light chain set forth as SEQ ID NO: 6, and the amino acid sequence set forth as SEQ ID NO: 28 corresponds to a variable region in the amino acid sequence of the heavy chain set forth as SEQ ID NO: 10. In the preferred embodiments (x) to (z) of these antibodies, the substitution, deletion or addition into the amino acid sequence constituting the amino acid sequence of the heavy chain or/and the light chain is particularly introduced into these variable regions.

Preferable embodiments of the fusion proteins comprising the antibody and a human lysosomal enzyme in the present invention include a fusion protein comprising a humanized anti-human transferrin receptor antibody (humanized anti-hTfR antibody) and human iduronate-2-sulfatase (hI2S). In this fusion protein, hI2S may be fused to either the heavy or light chain that constitutes the humanized anti-hTfR antibody insofar as it can retain both its affinity for the human transferrin receptor and the enzymatic activity of the human lysosomal enzyme. When hI2S is attached to a heavy chain, hI2S may be fused to either C-terminal side or the N-terminal side of the heavy chain, and when hI2S is attached to a light chain, hI2S may be fused to either C-terminal side or the N-terminal side of the light chain.

As preferable embodiments of the fusion proteins comprising the humanized anti-hTfR antibody and hI2S include a fusion protein in which the humanized anti-hTfR antibody is linked to the C-terminal side of the heavy chain of the humanized anti-hTfR antibody. Examples of preferable fusion proteins include those shown in (1) to (3) below;

(1) a fusion protein comprising a light chain of the humanized anti-hTfR antibody having the amino acid sequence set forth as SEQ ID NO: 2, and a heavy chain of humanized anti-hTfR antibody having the amino acid sequence set forth as SEQ ID NO: 8 and linked, on the C-terminus thereof via a linker sequence, to human iduronate-2-sulfatase, (2) a fusion protein comprising a light chain of the humanized anti-hTfR antibody having the amino acid sequence set forth as SEQ ID NO:4, and a heavy chain of humanized anti-hTfR antibody having the amino acid sequence set forth as SEQ ID NO: 9 and linked, on the C-terminus thereof via a linker sequence, to human iduronate-2-sulfatase, (3) a fusion protein comprising a light chain of the humanized anti-hTfR antibody having the amino acid sequence set forth as SEQ ID NO: 6, and a heavy chain of humanized anti-hTfR antibody having the amino acid sequence set forth as SEQ ID NO: 10 and linked, on the C-terminus thereof via a linker sequence, to human iduronate-2-sulfatase.

In these fusion proteins (1) to (3) above, the human iduronate-2-sulfatase preferably has the amino acid represented by SEQ ID NO:1, and the linker sequence preferably has the amino acid sequence Gly-Ser. These fusion proteins usually comprise two light chains, and two heavy chains bound to human iduronate-2-sulfatase.

Further, as preferable embodiments of the fusion proteins comprising the humanized anti-hTfR antibody and hI2S include;

(1) a fusion protein comprising a light chain of the humanized anti-hTfR antibody having the amino acid sequence set forth as SEQ ID NO: 2, and a heavy chain of the humanized anti-hTfR antibody linked, on the C-terminal side thereof and via a linker sequence Gly-Ser, to the human iduronate-2-sulfatase, and having the amino acid sequence set forth as SEQ ID NO:13 as the whole, (2) a fusion protein comprising a light chain of the humanized anti-hTfR antibody having the amino acid sequence set forth as SEQ ID NO: 4, and a heavy chain of the humanized anti-hTfR antibody linked, on the C-terminal side thereof and via a linker sequence Gly-Ser, to the human iduronate-2-sulfatase, and having the amino acid sequence set forth as SEQ ID NO:15 as the whole, (3) a fusion protein comprising a light chain of the humanized anti-hTfR antibody having the amino acid sequence set forth as SEQ ID NO: 6, and a heavy chain of the humanized anti-hTfR antibody linked, on the C-terminal side thereof and via a linker sequence Gly-Ser, to the human iduronate-2-sulfatase, and having the amino acid sequence set forth as SEQ ID NO:17 as the whole.

These fusion proteins usually comprise two light chains, and two heavy chains linked to the human iduronate-2-sulfatase.

The lyophilized formulation in the present invention contains, as an active ingredient, a fusion protein comprising an antibody and a human lysosomal enzyme, and further contains a neutral salt, a disaccharide, a nonionic surfactant, and a buffer.

As for the neutral salt to be contained in the lyophilized formulation, there is no particular limitation insofar as they are pharmaceutically acceptable, but sodium chloride and magnesium chloride are preferable as such neutral salts, and sodium chloride is particularly preferable.

The amount of the neutral salt in the lyophilized formulation is preferably 0.015 to 2.5 (w/w), more preferably 0.05 to 0.5 (w/w), even more preferably 0.1 to 0.25 (w/w), relative to the amount of fusion protein, for example 0.16 (w/w).

The disaccharide contained in the lyophilized formulation is not particularly limited insofar as it is pharmaceutically acceptable, but trehalose, sucrose, maltose, lactose and a combination thereof are preferable, and sucrose is particularly preferable.

The amount of disaccharide in the lyophilized formulation is preferably 2.5 to 200 (w/w), more preferably 5 to 50 (w/w), still more preferably 10 to 25 (w/w), relative to the amount of fusion protein, for example 15 (w/w).

The nonionic surfactant contained in the lyophilized formulation is not particularly limited insofar as it is pharmaceutically acceptable, but polysorbate and poloxamer are preferable as such a nonionic surfactant. For example, polysorbate 20, polysorbate 80, and polyoxyethylene(160) polyoxypropylene(30)glycol are preferable as nonionic surfactants. In particular, polyoxyethylene(160)polyoxypropylene(30)glycol is preferred. Polyoxyethylene(160) polyoxypropylene(30)glycol is synonymous with poloxamer 188.

The amount of nonionic surfactant in the lyophilized formulation is preferably 0.05 to 6 (w/w), more preferably 0.02 to 0.2 (w/w), still more preferably 0.04 to 0.1 (w/w), relative to the amount of fusion protein, for example 0.065 (w/w).

The buffer in the lyophilized formulation is not particularly limited insofar as they can be used as a excipient for a pharmaceutical product, but it is preferably a phosphate buffer. The phosphate buffer is added to the lyophilized formulation such that when the lyophilized formulation is dissolved in pure water, the pH is preferably 5.5 to 7.5, and more preferably the pH is 6.0 to 7.0, for example pH 6.5.

Examples of preferable compositions of the lyophilized formulations of the present invention include;

(A) The amount of the fusion protein comprising an antibody and a human lysosomal enzyme is 0.5 to 20 mg, and the amounts of a neutral salt, a disaccharide, and a nonionic surfactant relative to the amount of the fusion protein are 0.015 to 2.5 (w/w), 2.5 to 200 (w/w), and 0.005 to 6 (w/w), respectively.

(B) The amount of the fusion protein comprising an antibody and a human lysosomal enzyme is 0.5 to 20 mg, and the amounts of a neutral salt, a disaccharide, and a nonionic surfactant relative to the amount of the fusion protein are 0.05 to 0.5 (w/w), 5 to 50 (w/w), and 0.02 to 0.2 (w/w), respectively.

(C) The amount of the fusion protein comprising an antibody and a human lysosomal enzyme is 0.5 to 20 mg, and the amounts of a neutral salt, a disaccharide, and a nonionic surfactant for the amount of the fusion protein are 0.1 to 0.25 (w/w), 10 to 25 (w/w), and 0.04 to 0.1 (w/w), respectively.

In (A) to (C) above, a phosphate buffer is added to the lyophilized formulation such that when the lyophilized formulation is dissolved in pure water, the pH is 5.5 to 7.5 or 6.0 to 7.0, for example, to 6.5.

Examples of more preferable compositions of the lyophilized formulations of the present invention include;

(D) The amount of the fusion protein comprising an antibody and a human lysosomal enzyme is 0.5 to 20 mg, and the amounts of sodium chloride, sucrose, and polyoxyethylene(160)polyoxypropylene(30)glycol relative to the amount of the fusion protein are 0.015 to 2.5 (w/w), 2.5 to 200 (w/w), and 0.005 to 6 (w/w), respectively.

(E) The amount of the fusion protein comprising an antibody and a human lysosomal enzyme is 0.5 to 20 mg, and the amounts of sodium chloride, sucrose, and polyoxyethylene(160)polyoxypropylene(30)glycol relative to the amount of the fusion protein are 0.05 to 0.5 (w/w), 5 to 50 (w/w), and 0.02 to 0.2 (w/w), respectively.

(F) The amount of the fusion protein comprising an antibody and a human lysosomal enzyme is 0.5 to 20 mg, and the amounts of sodium chloride, sucrose, and polyoxyethylene(160)polyoxypropylene(30)glycol relative to the amount of the fusion protein are 0.1 to 0.25 (w/w), 10 to 25 (w/w), and 0.04 to 0.1 (w/w), respectively.

In (D) to (F) above, a phosphate buffer is added such that when the lyophilized formulation is dissolved in pure water, the pH is 5.5 to 7.5 or 6.0 to 7.0, especially 6.5.

As an example of a more specific composition of the lyophilized formulation of the present invention, (G) The amount of the fusion protein comprising an antibody and a human lysosomal enzyme is 10 mg, and the amounts of sodium chloride, sucrose, and polyoxyethylene (160)polyoxypropylene(30)glycol relative to the amount of the fusion protein are 0.16 (w/w), 15 (w/w), and 0.65 (w/w), respectively, with a phosphate buffer added so that the pH becomes 6.0 to 7.0 when dissolved with pure water.

In the lyophilized formulation indicated by (A) to (G) above, the fusion protein of an antibody and a human lysosomal enzyme is, for example, a fusion protein comprising the humanized anti-hTfR antibody and hI2S. As preferred embodiments of the fusion protein comprising a humanized anti-hTfR antibody and hI2S includes;

(1) a fusion protein, wherein the light chain of the humanized anti-hTfR antibody has an amino acid sequence set forth as SEQ ID NO:2, the heavy chain of the humanized anti-hTfR antibody has an amino acid sequence set forth as SEQ ID NO:8, and the C-terminal side of the heavy chain is linked to human iduronate-2-sulfatase via a linker sequence, (2) a fusion protein, wherein the light chain of the humanized anti-hTfR antibody has an amino acid sequence set forth as SEQ ID NO:4, the heavy chain of the humanized anti-hTfR antibody has an amino acid sequence set forth as SEQ ID NO:9, and the C-terminal side of the heavy chain is linked to human iduronate-2-sulfatase via a linker sequence, (3) a fusion protein, wherein the light chain of the humanized anti-hTfR antibody has an amino acid sequence set forth as SEQ ID NO:6, the heavy chain of the humanized anti-hTfR antibody has an amino acid sequence set forth as SEQ ID NO:10, and the C-terminal side of the heavy chain is linked to human iduronate-2-sulfatase via a linker sequence.

In the fusion proteins of (1) to (3) above, human iduronate-2-sulfatase preferably has the amino acid set forth as SEQ ID NO:1, and the linker sequence preferably has the amino acid sequence set forth as (Gly-Ser). And these fusion proteins are usually composed of two heavy chains bound to human iduronate-2-sulfatase and two light chains.

As further preferred embodiments of the fusion proteins comprising a humanized anti-hTfR antibody and hI2S in the lyophilized formulation shown in (A) to (G) above include;

(4) a fusion protein wherein, the light chain of the humanized anti-hTfR antibody has an amino acid sequence set forth as SEQ ID NO:2, and
the heavy chain of the humanized anti-hTfR antibody is linked to human iduronate-2-sulfatase at its C-terminal side via a linker having the amino acid sequence set forth as (Gly-Ser), and has the amino acid sequence set forth as SEQ ID NO:13, (5) a fusion protein wherein, the light chain of the humanized anti-hTfR antibody has an amino acid sequence set forth as SEQ ID NO:4, and
the heavy chain of the humanized anti-hTfR antibody is linked to human iduronate-2-sulfatase at its C-terminal side via a linker having the amino acid sequence set forth as (Gly-Ser), and has the amino acid sequence set forth as SEQ ID NO:15, (6) a fusion protein wherein, the light chain of the humanized anti-hTfR antibody has an amino acid sequence set forth as SEQ ID NO:6, and
the heavy chain of the humanized anti-hTfR antibody is linked to human iduronate-2-sulfatase at its C-terminal side via a linker having the amino acid sequence set forth as (Gly-Ser) and has the amino acid sequence set forth SEQ ID NO:17.

In the lyophilized formulation shown in (A) or (F) above, when the fusion proteins of an antibody and a human lysosomal enzyme are shown in (1) to (6) above, the amount of the fusion protein is preferably 0.5 to 20 mg, for example, 2.0 to 10 mg, 2.0 to 6.0 mg, and so on. The amount is adjusted to 2.5 mg, 5.0 mg, and a like as needed. Examples of the compositions of preferable lyophilized formulations of the fusion proteins include;

(H) a lyophilized formulation, wherein the amount of fusion protein is 0.5 to 20 mg, and the amounts of sodium chloride, sucrose, and polyoxyethylene(160)polyoxypropylene(30)glycol relative to the amount of fusion protein are 0.015 to 2.5 (w/w), 2.5 to 200 (w/w), and 0.005 to 6 (w/w), respectively, (I) a lyophilized formulation, wherein the amount of fusion protein is 0.5 to 20 mg, and the amounts of sodium chloride, sucrose, and polyoxyethylene(160)polyoxypropylene(30)glycol relative to the amount of fusion protein are 0.05 to 0.5 (w/w), 5 to 50 (w/w), and 0.02 to 0.2 (w/w), respectively, (J) a lyophilized formulation, wherein the amount of fusion protein is 0.5 to 20 mg, and the amounts of sodium chloride, sucrose, and polyoxyethylene(160)polyoxypropylene(30)glycol relative to the amount of fusion protein are 0.1 to 0.25 (w/w), 10 to 25 (w/w), and 0.04 to 0.1 (w/w), respectively.

A more specific example is, (K) a lyophilized formulation, wherein the amount of fusion protein is 10 mg, and the amounts of sodium chloride, sucrose, and polyoxyethylene(160)polyoxypropylene(30)glycol relative to the amount of fusion protein are 0.16 (w/w), 15 (w/w), and 0.65 (w/w), respectively, with a phosphate buffer added so that the pH becomes 6.0 to 7.0 when dissolved with pure water.

The lyophilized formulation of the present invention containing, as an active ingredient, the fusion protein comprising an antibody and a human lysosomal enzyme can be supplied, for example, in a sealed or filled form in a container such as a double-chamber syringe or vial. The lyophilized formulation of the present invention may also be supplied as a kit with a solution dedicated to dissolving the lyophilized formulation. The lyophilized formulations, for example, are dissolved in a dedicated solution, pure water, Ringer's solution, and so on, before use, and then diluted with physiological saline to make an infusion. This infusion is infused intravenously. Alternatively, lyophilized formulations may be administered intramuscularly, intraperitoneally, subcutaneously, and so on to patients. The material of the container such as a syringe and a vial for sealing or filling the lyophilized formulation is not particularly limited, but borosilicate glass is preferable, and also hydrophobic resin such as a cycloolefin copolymer which is a copolymer of a cyclic olefin and an olefin, a ring-opened polymer of cycloolefins, or a hydrogenated ring-opened polymer of cycloolefins is preferable.

EXAMPLES

While the present invention will be described in further detail below referring to examples, it is not intended that the present invention be limited to the examples.

[Example 1] Construction of Expression Vector for hI2S-Humanized Anti-hTfR Antibody Fusion Protein An expression vector for hI2S-humanized anti-hTfR antibody fusion protein was constructed using genes encoding three types of humanized anti-hTfR antibodies (Nos. 1 to 3). The antibody No. 1 comprises a light chain having the amino acid sequence set forth as SEQ ID NO:2 and a heavy chain having the amino acid sequence set forth as SEQ ID NO:8, the antibody No. 2 comprises a light chain having the amino acid sequence set forth as SEQ ID NO:4 and a heavy chain having the amino acid sequence set forth as SEQ ID NO:9, the antibody No. 3 comprises a light chain having the amino acid sequence set forth as SEQ ID NO:6 and a heavy chain having the amino acid sequence set forth as SEQ ID NO:10, respectively.

A pEF/myc/nuc vector (Invitrogen Inc.) was digested with KpnI and NcoI to cut out the region containing the EF-1α promoter and its first intron, and the region was blunt-ended with T4 DNA polymerase. A pCI-neo (Invitrogen Inc.) was digested with BglII and EcoRI to cut out the region containing the enhancer/promoter and intron of CMV, and then the region was blunt-ended with T4 DNA polymerase. The above region containing the EF-1α promoter and its first intron was inserted into this to construct a pE-neo vector. The pE-neo vector was digested with SfiI and BstXI and a region of approximately 1 kbp containing the neomycin resistance gene was cut out. Amplification of hygromycin gene was carried out by PCR reaction using primers Hyg-Sfi5' (SEQ ID NO:11) and Hyg-BstX3' (SEQ ID NO:12) and using pcDNA 3.1/Hygro(+)(Invitrogen Inc.) as a template. The amplified hygromycin gene was digested with SfiI and BstXI and inserted into the pE-neo vector from which the above neomycin resistance gene has been cut out to construct a pE-hygr vector.

A DNA fragment (SEQ ID NO:3) containing the gene encoding the full length of the light chain of the humanized anti-hTfR antibody No. 1 having the amino acid sequence set forth as SEQ ID NO:2 was synthesized. A MluI sequence was introduced on the 5' side of this DNA fragment and a NotI sequence on the 3' side thereof. This DNA fragment was digested with MluI and NotI and incorporated between MluI and Not of the pE-neo vector. The obtained vector was designated pE-hygr(LC1) which is a vector for expressing the light chain of humanized anti-hTfR antibody No. 1.

A DNA fragment (SEQ ID NO:5) containing a gene encoding the full length of the light chain of humanized anti-hTfR antibody No. 2 having the amino acid sequence set forth as SEQ ID NO:4 was synthesized. The MluI sequence was introduced on the 5' side of this DNA fragment and the NotI sequence on the 3' side thereof. This DNA fragment was digested with MluI and NotI and incorporated between MluI and NotI of the pE-neo vector. The resulting vector was designated pE-hygr(LC2) which is a vector for expressing the light chain of humanized anti-hTfR antibody No. 2.

A DNA fragment (SEQ ID NO:7) containing a gene encoding the full length of the light chain of humanized anti-hTfR antibody No. 3 having the amino acid sequence set forth as SEQ ID NO:6 was synthesized. The MluI sequence was introduced on the 5' side of this DNA fragment and the NotI sequence on the 3' side thereof. This DNA fragment was digested with MluI and NotI and incorporated between MluI and NotI of the pE-neo vector. The obtained vector was defined as pE-hygr(LC3) which is a vector for expressing the light chain of humanized anti-hTfR antibody No. 3.

A DNA fragment was artificially synthesized, having a nucleotide sequence set forth as SEQ ID NO:14 containing a gene encoding a protein in which hI2S having an amino acid sequence set forth as SEQ ID NO:1 is linked to the C-terminal side of the heavy chain of the humanized anti-hTfR antibody No. 1 having an amino acid sequence set forth as SEQ ID NO:8 via a linker having an amino acid sequence set forth as (Gly-Ser). This DNA fragment encodes a protein having the amino acid sequence set forth as SEQ ID NO:13, in which a heavy chain of humanized anti-hTfR antibody No. 1 binds to hI2S. This DNA fragment was digested with MluI and NotI and inserted between MluI and Not of the pE-neo vector to construct pE-neo (HC-I2S-1).

A DNA fragment was artificially synthesized, having a nucleotide sequence set forth as SEQ ID NO:16 containing a gene encoding a protein in which hI2S having an amino acid sequence set forth as SEQ ID NO:1 is linked to the C-terminal side of the heavy chain of the humanized anti-hTfR antibody No. 2 having an amino acid sequence set forth as SEQ ID NO:9 via a linker having an amino acid sequence set forth as (Gly-Ser). This DNA fragment encodes a protein having the amino acid sequence set forth as SEQ ID NO:15, in which a heavy chain of humanized anti-hTfR antibody No. 2 binds to hI2S. This DNA fragment was digested with MluI and NotI and inserted between MluI and NotI of the pE-neo vector to construct pE-neo (HC-I2S-2).

A DNA fragment was artificially synthesized, having a nucleotide sequence set forth as SEQ ID NO:18 containing a gene encoding a protein in which hI2S having an amino acid sequence set forth as SEQ ID NO:1 is linked to the C-terminal side of the heavy chain of the humanized anti-hTfR antibody No. 3 having an amino acid sequence set forth as SEQ ID NO:10 via a linker having an amino acid sequence set forth as (Gly-Ser). This DNA fragment encodes a protein having the amino acid sequence set forth as SEQ ID NO:17, in which a heavy chain of humanized anti-hTfR antibody No. 3 binds to hI2S. This DNA fragment was digested with MluI and NotI and inserted between MluI and NotI of the pE-neo vector to construct pE-neo (HC-I2S-3).

[Example 2] Preparation of a High Expression Cell Lines of hI2S-Humanized Anti-hTtR Antibody Fusion Proteins CHO cells (CHO-K1 obtained from American Type Culture Collection) were transformed with combinations of pE-hygr (LC1) and pE-neo (HC-I2S-1) constructed in Example 1, pE-hygr (LC2) and pE-neo (HC-I2S-2) constructed in Example 1 and pE-hygr (LC3) and pE-neo (HC-I2S-3) constructed in Example 1, respectively, using the GenePulser (Bio-Rad Inc.). Transformation of cells was in brief carried out by the following method.

$5 \times 10^5$ CHO-K1 cells were seeded in a 3.5 cm culture dish to which CD OptiCHO™ medium (Thermo Fisher Scientific Inc.) was added and cultured overnight at 37° C. under 5% $CO_2$. After the culture, the cells were suspended in Opti-MEM™ I medium (Thermo Fisher Scientific Inc.) to a density of $5 \times 10^6$ cells/mL. 100 μL of the cell suspension was collected, and thereto 5 μL each of the pE-hygr (LC1) and pE-neo (HC-I2S-1) plasmid DNA solutions both having been diluted to 100 j±g/mL with CD OptiCHO™ medium was added. Electroporation was performed using GenePulser (Bio-Rad Inc.) to introduce the plasmids into the cells. After overnight culture under the condition of 37° C., 5% $CO_2$, the cells were selectively cultured in CD OptiCHO™ medium supplemented with 0.5 mg/mL of hygromycin and 0.8 mg/mL of G418. For the combination of pE-hygr (LC2) and pE-neo (HC-I2S-2) and the combination of pE-hygr (LC3) and pE-neo (HC-I2S-3), the transformations of the cells were conducted by the same method.

Then, the cells selected above through the selection culture were seeded on 96-well plates so that not more than one cell might be seeded per well by limiting dilution. The cells then were cultured for about 10 days so that monoclonal colonies formed. Respective culture supernatants of the wells in which monoclonal colony formed were collected, the amount of the humanized antibody contained in culture supernatants was determined by ELISA, and the hI2S-humanized anti-hTfR antibody fusion protein high-expressing cell lines were selected.

The ELISA above was conducted as follows in general. To each well of 96-well microtiter plates (Nunc Inc.) was added 100 μL of a goat anti-human IgG polyclonal antibody solution diluted with 0.05 M sodium bicarbonate buffer (pH 9.6) to 4 μg/mL, and the plate was left to stand for at least one hour at room temperature so as to allow the antibody to be adsorbed by the plates. Then, after each well was washed three times with a phosphate-buffered saline (pH 7.4) supplemented with 0.05% Tween20 (PBS-T), 200 μL of Starting Block (PBS) Blocking Buffer (Thermo Fisher Scientific Inc.) was added to each well, and the plates were left to stand for 30 minutes at room temperature. After each well was washed with PBS-T three times, the culture supernatant or the human IgG reference standard product which had been diluted with a phosphate buffer saline (pH 7.4) supplemented with 0.5% BSA and 0.05% Tween20 (PBS-BT) to appropriate concentrations, was added to each well, in the amount of 100 μL, and the plates were left to stand for at least one hour at room temperature. After the plates were washed three times with PBS-T, 100 μL of HRP-labeled anti-human IgG polyclonal antibody solution which had been diluted with PBS-BT, was added to each well, and the plates were left to stand for at least one hour at room temperature. After the wells were washed three times with PBS-T, citrate-phosphate buffer (pH 5.0) containing 0.4 mg/mL o-phenylenediamine was added to each well, in the amount of 100 μL, and the wells were left to stand for 8 to 20 minutes at room temperature. Then, 1 mol/L sulfuric acid was added to each well in the amount of 100 μL to terminate the reaction, and the absorbance for each well was measured at 490 nm using a 96-well plate reader. The cells corresponding to the wells which exhibited the higher measurements were regarded as a high-expressing cell line for hI2S-humanized anti-hTfR antibody fusion protein.

A high-expressing cell line of a hI2S-humanized anti-hTfR antibody fusion protein obtained by transformation with combination of pE-hygr(LC1) and pE-neo(HC-I2S-1) was designated as a hI2S-anti-hTfR antibody expressing strain 1. The fusion protein of hI2S and humanized anti-hTfR antibody expressed by this cell line was designated as I2S-anti-hTfR antibody 1.

A high-expressing cell line of a hI2S-humanized anti-hTfR antibody fusion protein obtained by transformation with combination of pE-hygr(LC2) and pE-neo(HC-I2S-2) was designated as a hI2S-anti-hTfR antibody expressing strain 2. The fusion protein of hI2S and humanized anti-hTfR antibody expressed by this cell line was designated as I2S-anti-hTfR antibody 2.

A high-expressing cell line of a hI2S-humanized anti-hTfR antibody fusion protein obtained by transformation with combination of pE-hygr(LC3) and pE-neo(HC-I2S-3) was designated as a hI2S-anti-hTfR antibody expressing strain 3. The fusion protein of hI2S and humanized anti-hTfR antibody expressed by this cell line was designated as I2S-anti-hTfR antibody 3.

The sequence numbers of amino acid sequences of the light and heavy chains of humanized antibodies, the amino acid sequences of the variable regions contained in those light and heavy chains, and the amino acid sequences of CDR 1 to 3 contained in those variable regions, which are contained in I2S-anti-hTfR antibody 1, I2S-anti-hTfR antibody 2, or I2S-anti-hTfR antibody 3, are summarized in Table 1.

about 200 L of serum-free medium (EX-CELL Advanced CHO Fed-batch Medium, Sigma Aldrich Inc.) containing 4 mM L-alanyl-L-glutamine, 100 μmol/L hypoxanthine and 16 μmol/L thymidine to the density of about $2 \times 10^5$ cells/mL. 140 L of this cell suspension was transferred to a culture tank. The cells were cultured for about 11 days at a temperature range of 34 to 37° C., while the medium was stirred with an impeller at a rate of 89 rpm, and the dissolved oxygen saturation of the medium was kept at about 40%. During the culture period, cell number, cell viability, and glucose and lactate concentrations of the medium were monitored. When the glucose concentration of the medium became less than 15 mmol/L, the glucose solution was immediately added to the medium so that the glucose concentration became 37.89 mmol/L. After completion of the culture, the medium was collected. The recovered medium was filtered with Millistak+HC Pod Filter grade D0HC (Merck Inc.) and further filtered with Millistak+ HCgrade X0HC (Merck Inc.) to obtain a culture supernatant containing I2S-anti-hTfR antibody 3. The culture supernatant was subjected to ultrafiltration using a Pellicon™ 3 Cassette w/Ultracel PLCTK Membrane (pore size: 30 kDa, membrane area: 1.14 m², Merck Inc.) and concentrated until the liquid volume was about 1/17. The concentrate was then filtered using OpticapXL600 (0.22 μm, Merck Inc.). The obtained solution was used as a concentrated culture supernatant.

[Example 4] Inactivation of the Virus

To the concentrated culture supernatant obtained in Example 3, tri-n-butyl phosphate (TNBP) and polysorbate 80 were added so that the final concentrations were 0.3% (v/v) and 1% (w/v), respectively, and gently stirred at room temperature for 4 hours. This process is conducted for inactivating the virus contaminating the culture supernatant. However, insofar as the culture is carried out using a serum-free medium not containing biological components, there is little possibility that viruses harmful to the human body are contaminated in the culture supernatant.

[Example 5] Purification of hI2S-Anti-hTfR Antibodies

The concentrated culture supernatant after the virus inactivation was filtrated by a Millipak-200 Filter Unit (pore size: 0.22 μm, Merck Inc.) after adding thereto 20 mM Tris-HCl buffer (pH 7.0) containing 0.5 volume of 140 mM NaCl. The solution after filtration was loaded onto a Mab-

TABLE 1

SEQ ID NOS of the light chain and heavy chain amino acid sequences contained in the fusion protein

| Name of fusion protein | Light chain | | | | | Heavy chain | | | | |
| --- | --- | --- | --- | --- | --- | --- | --- | --- | --- | --- |
| | Full length | Variable region | CDR1 | CDR2 | CDR3 | Full length | Variable region | CDR1 | CDR2 | CDR3 |
| I2S-anti-hTfR antibody 1 | 2 | 23 | 29, 30 | 31, 32 | 33 | 8 | 24 | 34, 35 | 36, 37 | 38, 39 |
| I2S-anti-hTfR antibody 2 | 4 | 25 | 40, 41 | 42, 43 | 44 | 9 | 26 | 45, 46 | 47, 48 | 49, 50 |
| I2S-anti-hTfR antibody 3 | 6 | 27 | 51, 52 | 53, 54 | 55 | 10 | 28 | 56, 57 | 58, 59 | 60, 61 |

[Example 3] Culture of hI2S-Anti-hTfR Antibody Expressing Strain

The hI2S-anti-hTfR antibodies were produced by the method described below. The hI2S-anti-hTfR antibody expressing strain 3 obtained in Example 2 was suspended in Select SuRe LX column (column volume: about 3.2 L, bed height: about 20 cm, GE Healthcare Inc.), which was a protein A affinity column, and equilibrated with 4 column volumes of 20 mM Tris-HCl buffer (pH 7.0) containing 140 mM NaCl, at a constant flow rate of 200 cm/hr to adsorb I2S-anti-hTfR antibody 3 to protein A.

Subsequently, the column was washed with 5 column volumes of 10 mM Tris-HCl buffer (pH 7.0) containing 500 mM NaCl and 450 mM arginine at the same flow rate. Then the column was further washed with 2.5 column volumes of 20 mM Tris-HCl buffer (pH 7.0) containing 140 mM NaCl at the same flow rate. Then the I2S-anti-hTfR antibody 3 adsorbed to Protein A was eluted with 5 column volumes of 100 mM glycine buffer (pH 3.5) containing 140 mM NaCl. The eluate was immediately neutralized by receiving it in a container containing 1 M Tris-HCl buffer (pH 7.5) in advance.

To the above eluate from the Protein A affinity column, 200 mM phosphate buffer (pH 7.0), 10 mM MES buffer (pH 7.3) containing 4 M NaCl and 2 mM phosphate buffer, and 1 M Tris-HCl buffer solution (pH 8.0) were added in the order, and the concentrations of sodium phosphate and NaCl contained in the eluate were adjusted to 2 mM and 215 mM, respectively, and the pH of the eluate was adjusted to 7.3. The eluate was then filtered through Opticap XL 600 (pore size: 0.22 µm, Merck Inc.). The solution after filtration was applied to a CHT Type II 40 µm column, a hydroxyapatite column (Column volume: about 3.2 L, bed height: about 20 cm, Bio-Rad Inc.), equilibrated with 4 column volumes of 10 mM MES buffer solution (pH 7.3) containing 215 mM NaCl and 2 mM sodium phosphate at a constant flow rate of 200 cm/hr to adsorb I2S-anti-hTfR antibody 3 to hydroxyapatite.

Subsequently, the column was washed with 5 column volumes of the same buffer at the same flow rate. Then I2S-anti-hTfR antibody 3 adsorbed on hydroxyapatite was eluted with 5 column volumes of 35 mM phosphate buffer (pH 7.3) containing 215 mM NaCl. Purification by the hydroxyapatite column was carried out twice using half volume of the eluate from the protein A affinity column.

To the above eluate from the hydroxyapatite column, dilute hydrochloric acid was added to adjust the pH to 6.5. Then, ultrafiltration was carried out using Pellicon™ 3 Cassette w/Ultracel PLCTK Membrane (pore size: 30 kDa, membrane area: 1.14 m², Merck Inc.) to concentrate I2S-antihTfR antibody 3 in the solution at the concentration of about 2 mg/mL. The concentrate was then filtered using Opticap XL 600 (0.22 µm, Merck Inc.).

The above concentrated solution was applied to a Superdex 200 column, size exclusion column (column volume: about 12.6 L, bed height: 40 cm, GE Healthcare Inc.) equilibrated with 5 column volumes of 20 mM phosphate buffer (pH 6.5) containing 0.8 mg/mL NaCl and 75 mg/mL sucrose at a constant flow rate of 19 cm/hr, and the same buffer was supplied at the same flow rate. At this time, an absorbance photometer for continuously measuring the absorbance of the eluate was placed in the flow path of the eluate from the size exclusion column, and the absorbance at 280 nm was monitored. The fractions which corresponded to an absorption peak at 280 nm were collected as a fractions containing I2S-anti-hTfR antibody 3, which was designated as a purified product of I2S-anti-hTfR antibody. Purification on the size exclusion column was carried out twice using half volume of the eluate from the hydroxyapatite column.

[Example 6] Manufacture of Lyophilized Products Containing I2S-Anti-hTfR Antibodies An aqueous solution, whose composition is shown in Table 2, was prepared using the purified I2S-anti-hTfR antibody obtained in Example 5. The aqueous solution was filtered using Vacuum Filter/Storage Bottle System, 0.22 µm (Corning Inc.). The solution after filtration was used as the test solution. Sodium hydroxide solution or dilute hydrochloric acid was added as needed to adjust the pH of the test solution to about 6.5.

TABLE 2

Composition of the test solution

| Component | Concentration (mg/mL) |
|---|---|
| I2S-anti-hTfR antibody | 5 |
| NaCl | 0.8 |
| $NaH_2PO_4$—$2H_2O$ | 2.136 |
| $Na_2HPO_4$ $12H_2O$ | 2.256 |
| sucrose | 75 |
| poloxamer 188 | 0.325 |

2.5 mL of each of the test solution was filled in a vial made of borosilicate glass, with a rubber stopper (made of chlorinated butyl) half-capped, and lyophilized. In the lyophilization process, the gas phase in the vials was replaced with nitrogen, and then the whole rubber stopper was capped to seal the vials. The lyophilized products formed a white mass in vials.

[Example 7] Evaluation of Stability of Lyophilized Formulation Containing I2S-Anti-hTfR Antibody The lyophilized products prepared in Example 6 were allowed to stand in a dark environment at 5° C. or 25° C. for 6 months. The lyophilized products in the vials at the start of standing, after 1 month, after 3 months, and after 6 months, were dissolved in 2.5 mL of pure water and the solutions were used as sample solutions. The pH of each sample solution was measured and the presence or absence of foreign matter was visually examined at a brightness of 2000 to 3750 1x under a white light source. The number of fine particles, whose particle sizes were 1 to 100 µm, was measured by the method shown in Example 8. The ratio of I2S-anti-hTfR antibody polymers in each sample solution was determined by the method shown in Example 9. In addition, the affinity of the I2S-anti-hTfR antibody contained in each sample solution with human TfR was determined by the method shown in Example 10. Furthermore, the enzymatic activity of the I2S-anti-hTfR antibody contained in each sample solution was determined by the method shown in Example 11.

Table 3 shows the results of the stability measurements of lyophilized formulations containing I2S-anti-hTfR antibody after left for 6 months in the dark at 5° C. As shown in Table 3, the pH of the sample solutions was kept at approximately pH 6.5 during the 6 month standing period of the lyophilized product. There was no foreign insoluble matter in the sample solutions during the same time period, which could be clearly observed optically. The ratio of polymers to whole I2S-anti-hTfR antibody in the sample solutions during the same time period was almost constant. Further, the number of fine particles, whose particle sizes were 1 to 100 µm, did not increase significantly during the same time period. An increase in the number of particles was observed in the sample solution left for 6 months standing, but it was within an acceptable range when the storage period of the lyophilized formulation was set at 2 years in a cold place. The enzyme activity of I2S-anti-hTfR antibody in the sample solutions remained almost constant during the same time period. Further, the affinity of I2S-anti-hTfR antibody contained in the sample solutions for human TfR did not decrease significantly during the same time period (Data not shown).

TABLE 3

Results of stability evaluation of lyophilized formulation stored in the dark at 5° C.

| Test item | At the start | 1 month | 2 Months | 3 Months | 6 Months |
|---|---|---|---|---|---|
| pH | 6.5 | 6.5 | 6.5 | 6.5 | 6.5 |
| Foreign insoluble matter (visual observation) | none | none | none | none | none |
| Ratio of polymers (%) | 1.13 | 1.09 | 1.08 | 1.02 | 1.19 |
| Number of fine particles (/vial) | 1110 | 1500 | 1550 | 730 | 3240 |
| Enzyme activity (mU/mg) | 419 | 436 | 425 | 422 | 515 |
| Affinity for hTfR ($K_D$) | — | — | — | — | — |

Table 4 shows the results of stability measurements of lyophilized formulations containing I2S-anti-hTfR antibodies after 6 months of standing in the dark at 25° C. As shown in Table 4, the pH of the sample solution was kept at approximately pH 6.5 during the 6 month standing period of the lyophilized product. Any foreign insoluble matter was not observed in the sample solutions during the same period, which could be clearly observed optically. The ratio of polymer was almost constant during the same period. The number of fine particles, whose particle sizes were 1 to 100 μm, did not increase significantly during the same time period. An increase in the number of fine particles was observed after 6 months, which was within an acceptable range when the storage period of the lyophilized formulation was set at 2 years in a cold place. The enzyme activity of I2S-anti-hTfR antibody in the sample solutions remained almost constant during the same period. Further, the affinity of I2S-anti-hTfR antibody contained in the sample solutions for human TfR did not decrease significantly during the same period (Data not shown).

TABLE 4

Results of stability evaluation for lyophilized formulation stored in the dark at 25° C.

| Test item | At the start | 1 month | 2 Months | 3 Months | 6 Months |
|---|---|---|---|---|---|
| pH | 6.5 | 6.5 | 6.5 | 6.5 | 6.5 |
| Foreign insoluble matter (visual observation) | none | none | none | none | none |
| Ratio of polymers (%) | 1.13 | 1.09 | 1.09 | 1.02 | 1.19 |
| Number of fine particles (/vial) | 1110 | 2140 | 3130 | 1060 | 2620 |
| Enzyme activity (mU/mg) | 419 | 445 | 430 | 430 | 506 |
| Affinity for hTfR ($K_D$) | — | — | — | — | — |

These results above indicate that a drug containing I2S-anti-hTfR antibody as an active ingredient can be provided to the market in a pharmacologically stable state by using the lyophilized formulation with the composition shown in Table 2, provided that the drug is placed in a cold place in the distribution process and in the storage.

[Example 8] Measurement of the Number of Particles Contained in the Sample Solution (Particle Size: 1 to 100 μm)

The measurement of the number of particles contained in the sample solutions was conducted by using a flow imaging particle analyzer FlowCAM™ (Fluid Imaging Technologies Inc.). The flow imaging particle analyzer enables to measure the number of particles contained in the sample solution by drawing the sample solution into a flow cell disposed perpendicularly to the optical system by a syringe pump, and to photograph the particles passing through the flow cell in real time. The measurement was carried out by setting the particle size to be detected to 1 to 100 μm.

[Example 9] Measurement of the Amount of Polymers of I2S-Anti-hTfR Antibodies Contained in a Sample Solution TSKgel UltraSW Aggregate 3 μm column, a size exclusion column chromatography, (7.8 mm in diameter×30 cm in length, TOSOH Inc.) was set on Shimazu HPLC system LC-20A (Shimadzu Corporation). A spectrophotometer was installed downstream of the column to measure the absorbance (Measurement wavelength: 215 nm) of the effluent from the column continuously. After equilibrating the column by loading 0.2 M aqueous sodium phosphate buffer solution at a flow rate of 0.5 mL/min, a sample solution containing 3 to 20 μg of I2S-anti-hTfR antibody was loaded onto the column, and a further 0.2 M aqueous sodium phosphate buffer solution was loading at the same flow rate. During this time, the elution profile was obtained by measuring the absorbance (Measurement wavelength: 215 nm) of the effluent from the column. From the obtained elution profiles, the peak area of the monomer of the I2S-anti-hTfR antibody (monomer peak area) and the peak area of the polymer of the I2S-anti-hTfR antibody appearing before the monomer peak (polymer peak area) were determined. The amount (%) of the polymer was determined by the following equation.

Amount of polymer (%)={Polymer peak area/(monomer peak area+polymer peak area)}×100

[Example 10] Measurement of Affinity of I2S-Anti-hTfR Antibody in Sample Solution to Human TfR The affinity of the I2S-anti-hTfR antibody to human TfR was determined by using OctetRED 96 (ForteBio Inc., a division of Pall Corporation), to which bio-layer interferometry (BLI) is applied. The basic principles of bio-layer interferometry are briefly explained below. When a layer of a biomolecule immobilized on the surface of a sensor tip is irradiated with light of a certain wavelength, the light is reflected from two of the surfaces, the one of the biomolecule and the other of inner, reference layer, producing interfering light waves. A molecule in the sample being measured binds to the biomolecule on the surface of the sensor tip and thus increases the thickness of the layers on the sensor tip, which results in a shift between the interfering waves. By measuring the variations of this shift between the interfering waves, determination of the number of the molecules bound to the layer of the biomolecules immobilized to the sensor tip surface and kinetic analysis of it can be performed in real time. The measurement was performed according generally to the operating manual attached to Octet RED96. As a human TfR, a recombinant human TfR (rhTfR: Sino Biological Inc.) was used, which had the amino acid sequence of the hTfR extracellular region, i.e., the cysteine residue at the position 89th from the N-terminal side to the phenylalanine at the C-terminus, of the amino acid sequence set forth as SEQ ID NO: 1, with a histidine tag attached to the N-terminus.

The Sample solutions prepared in Example 6 were subjected to 2-fold dilution steps with HBS-P+(10 mM HEPES containing 150 mM NaCl, 50 µM EDTA, and 0.05% surfactant P20) to prepare 7 step diluted solutions, whose concentrations were 0.78125 to 50 nM (0.117 to 7.5 µg/mL). The rhTfR-ECD(Histag) solution was prepared by diluting hTtR with HBS-P+ to adjust the concentration to 25 µg/mL.

Each of the sample solutions prepared above by 2-fold dilution steps was added, 200 µL/well, to a 96-well plate, black (Greiner Bio-One Inc.). Each of the rhuman TfR-ECD (Histag) solution prepared above was added, 200 µL/well, to predetermined wells. To respective wells for baseline, dissociation and washing were added HBS-P+, 200 µL/well. To wells for regeneration were added 10 mM Glycine-HCl, pH 1.7, 200 µL/well. To wells for activation was added 0.5 mM NiCl$_2$ solution, 200 µL/well. The plate and biosensor (Biosensor/Ni-NTA: ForteBio Inc., a division of Pall Corporation) were set in the prescribed positions of Octet RED96.

Octet RED96 was run under the conditions shown in Table 5 below to collect data, on which then, using the analyzing software attached to Octet RED96, and fitting the binding reaction curve to 1:1 binding model or 2:1 binding model, the association rate constant ($k_{on}$) and dissociation rate constant ($k_{off}$) of anti-hTfR antibody to r human TfR were measured and the dissociation constant ($K_D$) was calculated. The measurement was performed at 25 to 30° C.

TABLE 5

Operating conditions of OctetRED 96

| Step | | Contact time (sec) | Speed (rpm) | Threshold |
|---|---|---|---|---|
| 1 | Baseline 1 | 60 | 1000 | — |
| 2 | Load | 600 | 1000 | 1.5~2.0 |
| 3 | Baseline 2 | 60 | 1000 | — |
| 4 | Associate | 180 | 1000 | — |
| 5 | Dissociate | 540 | 1000 | — |
| 6 | Regenerate | 5 | 1000 | — |
| 7 | Wash | 5 | 1000 | — |
| | Steps 6~7 repeated 6~7 times. | | | |
| 8 | activate | 60 | 1000 | — |
| | Steps 1~8 repeated until all the samples measured. | | | |

[Example 11] Measurement of Enzymatic Activity of I2S-Anti-hTfR Antibodies in Sample Solution The sample solutions were desalted by membrane filtration using a vertical polyethersulfone membrane (VIVAS-PIN2 5,000 MWCO PES, Saltrius Inc.) as an ultrafiltration membrane, and then desalted samples were diluted to approximately 100 ng/mL with Reaction Buffer (5 mM sodium acetate, 0.5 mg/L BSA, 0.1% Triton X-100, pH 4.45). To each well of a 96-well microtiter plate (Fluoro-Nunc Plate, Nunc Inc.), 10 µL of each rhI2S sample was added and pre-incubated for 15 minutes at 37° C. Substrate solutions were prepared by dissolving 4 methylumbelliferyl sulfate (SIGMA) in substrate buffer (5 mM sodium acetate, pH 4.45, containing 0.5 mg/mL BSA) to a final concentration of 1.5 mg/mL. 100 µL of Substrate solutions was added to each well containing rhI2S sample solution, and the plates were allowed to stand in the dark at 37° C. for 1 hour. After the incubation, 190 µL of stop buffer (0.33 M glycine, 0.21 M sodium carbonate buffer solution, pH 10.7) was added to each well containing the sample. 150 µL of 0.4 µmol/L 4-methylumbelliferone (4-MUF, Sigma) solution and 150 µL of the stop buffer were added to a well as the standard, then the plate was read on a 96-well plate reader with excitation light at the wavelength of 330 nm and fluorescent light at the wavelength of 440 nm.

A standard curve was produced by measuring fluorescence intensity at various concentrations of 4-MUF in solution. The fluorescence intensity of each sample was extrapolated to the standard curve. Results were calculated as activity in Units/mL where one Unit of activity was equal to 1 µmol of 4-MUF produced per minute at 37° C. A published US patent application (publication No. 2004-0229250) was referred to for conducting this measurement.

INDUSTRIAL APPLICABILITY

According to the present invention, a lyophilized formulation containing a protein in which an antibody and a lysosomal enzyme are combined as an active ingredient can be provided to the market in a pharmacologically stable state.

SEQUENCE LISTING FREE TEXT

SEQ ID NO:2: Amino acid sequence of the light chain of humanized anti-hTfR

SEQ ID NO:3: Nucleotide sequence encoding amino acid sequence of the light-chain of humanized anti-hTfR antibody No. 1, synthetic sequence SEQ ID NO:4: Amino acid sequence of the light-chain of humanized anti-hTfR antibody No. 2

SEQ ID NO:5: Nucleotide sequence encoding amino acid sequence of the light chain of humanized anti-hTfR antibody No. 2, synthetic sequence SEQ ID NO:6: amino acid sequence of the light chain of humanized anti-hTfR antibody No. 3

SEQ ID NO:7: Nucleotide sequence encoding amino acid sequence of the light chain of humanized anti-hTfR antibody No. 3, synthetic sequence SEQ ID NO:8: Amino acid sequence of the heavy chain of humanized anti-hTfR antibody No. 1

SEQ ID NO:9: Amino acid sequence of the heavy chain of humanized anti-hTfR antibody No. 2

SEQ ID NO:10: Amino acid sequence of the heavy chain of humanized anti-hTtR antibody No. 3

SEQ ID NO: 11: Primer Hyg-Sfi5', synthetic sequence
SEQ ID NO: 12: Primer Hyg-BstX3', synthetic sequence
SEQ ID NO:13: Amino acid sequence of fused protein of the heavy chain of humanized anti-hTfR antibody No. 1 and hI2S
SEQ ID NO:14: Nucleotide sequence encoding amino acid sequence of fused protein of the heavy chain of humanized anti-hTtR antibody No. 1 and hI2S, synthetic sequence
SEQ ID NO: 15: Amino acid sequence of fused protein of the heavy chain of humanized anti-hTfR antibody No. 2 and hI2S
SEQ ID NO:16: Nucleotide sequence encoding amino acid sequence of fused protein of the heavy chain of humanized anti-hTfR antibody No. 2 and hI2S, synthetic sequence
SEQ ID NO:17: Amino acid sequence of fused protein of the heavy chain of humanized anti-hTfR antibody No. 3 and hI2S
SEQ ID NO:18: Nucleotide sequence encoding amino acid sequence of fused protein of the heavy chain of humanized anti-hTfR antibody No. 3 and hI2S, synthetic sequence
SEQ ID NO:19: Amino acid sequence of an exemplified linker 1
SEQ ID NO:20: Amino acid sequence of an exemplified linker 2
SEQ ID NO:21: Amino acid sequence of an exemplified linker 3
SEQ ID NO:23: Amino acid sequence of the light chain variable region of humanized anti-hTfR antibody No. 1
SEQ ID NO:24: Amino acid sequence of the heavy chain variable region of humanized anti-hTfR antibody No. 1
SEQ ID NO:25: Amino acid sequence of the light chain variable region of humanized anti-hTfR antibody No. 2
SEQ ID NO:26: Amino acid sequence of the heavy chain variable region of humanized anti-hTfR antibody No. 2
SEQ ID NO:27: Amino acid sequence of the light chain variable region of humanized anti-hTfR antibody No. 3
SEQ ID NO:28: Amino acid sequence of the heavy chain variable region of humanized anti-hTfR antibody No. 3
SEQ ID NO:29: Amino acid sequence 1 of CDR1 in the light chain of anti-hTfR antibody No. 1
SEQ ID NO:30: Amino acid sequence 2 of CDR1 in the light chain of anti-hTfR antibody No. 1
SEQ ID NO:31: Amino acid sequence 1 of CDR2 in the light chain of anti-hTfR antibody No. 1
SEQ ID NO:32: Amino acid sequence 2 of CDR2 in the light chain of anti-hTfR antibody No. 1
SEQ ID NO:33: Amino acid sequence of CDR3 in the light chain of anti-hTfR antibody No. 1
SEQ ID NO:34: Amino acid sequence 1 of CDR1 in the heavy chain of anti-hTfR antibody No. 1
SEQ ID NO:35: Amino acid sequence 2 of CDR1 in the heavy chain of anti-hTfR antibody No. 1
SEQ ID NO:36: Amino acid sequence 1 of CDR2 in the heavy chain of anti-hTfR antibody No. 1
SEQ ID NO:37: Amino acid sequence 2 of CDR2 in the heavy chain of anti-hTfR antibody No. 1
SEQ ID NO:38: Amino acid sequence 1 of CDR3 in the heavy chain of anti-hTfR antibody No. 1
SEQ ID NO:39: Amino acid sequence 2 of CDR3 in the heavy chain of anti-hTfR antibody No. 1
SEQ ID NO:40: Amino acid sequence 1 of CDR1 in the light chain of anti-hTfR antibody No. 2
SEQ ID NO:41: Amino acid sequence 2 of CDR1 in the light chain of anti-hTfR antibody No. 2
SEQ ID NO:42: Amino acid sequence 1 of CDR2 in the light chain of anti-hTfR antibody No. 2
SEQ ID NO:43: Amino acid sequence 2 of CDR2 in the light chain of anti-hTfR antibody No. 2
SEQ ID NO:44: Amino acid sequence of CDR3 in the light chain of anti-hTfR antibody No. 2
SEQ ID NO:45: Amino acid sequence 1 of CDR1 in the heavy chain of anti-hTfR antibody No. 2
SEQ ID NO:46: Amino acid sequence 2 of CDR1 in the heavy chain of anti-hTfR antibody No. 2
SEQ ID NO:47: Amino acid sequence 1 of CDR2 in the heavy chain of anti-hTfR antibody No. 2
SEQ ID NO:48: Amino acid sequence 2 of CDR2 in the heavy chain of anti-hTfR antibody No. 2
SEQ ID NO:49: Amino acid sequence 1 of CDR3 in the heavy chain of anti-hTfR antibody No. 2
SEQ ID NO:50: Amino acid sequence 2 of CDR3 in the heavy chain of anti-hTfR antibody No. 2
SEQ ID NO:51: Amino acid sequence 1 of CDR1 in the light chain of anti-hTfR antibody No. 3
SEQ ID NO:52: Amino acid sequence 2 of CDR1 in the light chain of anti-hTfR antibody No. 3
SEQ ID NO:53: Amino acid sequence 1 of CDR2 in the light chain of anti-hTfR antibody No. 3
SEQ ID NO:54: Amino acid sequence 2 of CDR2 in the light chain of anti-hTfR antibody No. 3
SEQ ID NO:55: Amino acid sequence of CDR3 in the light chain of anti-hTfR antibody No. 3
SEQ ID NO:56: Amino acid sequence 1 of CDR1 in the heavy chain of anti-hTfR antibody No. 3
SEQ ID NO:57: Amino acid sequence 2 of CDR1 in the heavy chain of anti-hTfR antibody No. 3
SEQ ID NO:58: Amino acid sequence 1 of CDR2 in the heavy chain of anti-hTfR antibody No. 3
SEQ ID NO:59: Amino acid sequence 2 of CDR2 in the heavy chain of anti-hTfR antibody No. 3
SEQ ID NO:60: Amino acid sequence 1 of CDR3 in the heavy chain of anti-hTfR antibody No. 3
SEQ ID NO:61: Amino acid sequence 2 of CDR3 in the heavy chain of anti-hTfR antibody No. 3

The invention claimed is:

1. A lyophilized formulation comprising;
a fusion protein including an antibody and a lysosomal enzyme, as an active ingredient, and further
a neutral salt, a disaccharide, a nonionic surfactant, and a buffer.

2. The lyophilized formulation according to claim 1, wherein the neutral salt is sodium chloride.

3. The lyophilized formulation according to claim 1, wherein the disaccharide is selected from the group consisting of trehalose, sucrose, maltose, and lactose.

4. The lyophilized formulation according to claim 1, wherein the nonionic surfactant is polysorbate or poloxamer.

5. The lyophilized formulation according to claim 1, wherein the nonionic surfactant is selected from the group consisting of polysorbate 20, polysorbate 80, and polyoxyethylene(160)polyoxypropylene(30)glycol.

6. The lyophilized formulation according to claim 1, wherein the buffer is a phosphate buffer.

7. The lyophilized formulation according to claim 1, wherein the disaccharide is sucrose, the nonionic surfactant is polyoxyethylene(160)polyoxypropylene(30)glycol, and the buffer is a phosphate buffer.

8. The lyophilized formulation according to claim 1, wherein the amounts of the neutral salt, the disaccharide, and the nonionic surfactant are 0.015 to 2.5 (w/w), 2.5 to 200 (w/w), and 0.005 to 6 (w/w), respectively, relative to the amount of the fusion protein.

9. The lyophilized formulation according to claim 1, wherein the amounts of the neutral salt, the disaccharide, and the nonionic surfactant are 0.05 to 0.5 (w/w), 5 to 50 (w/w), and 0.02 to 0.2 (w/w), respectively, relative to the amount of the fusion protein.

10. The lyophilized formulation according to claim 1, wherein the amounts of the neutral salt, the disaccharide, and the nonionic surfactant is 0.1 to 0.25 (w/w), 10 to 25 (w/w), and 0.04 to 0.1 (w/w), respectively, relative to the amount of the fusion protein.

11. The lyophilized formulation according to claim 1, wherein the pH is 5.5 to 7.5 when dissolved in pure water.

12. The lyophilized formulation according to claim 1, wherein the fusion protein is a fusion protein in which the lysosomal enzyme is linked to the light chain or the heavy chain of the antibody on the C-terminal side or the N-terminal side thereof by a peptide bond.

13. The lyophilized formulation according to claim 1, wherein the fusion protein is a fusion protein in which the lysosomal enzyme is linked to the heavy chain of the antibody on the C-terminal side thereof by a peptide bond.

14. The lyophilized formulation according to claim 1, wherein the fusion protein is a fusion protein in which the lysosomal enzyme is linked to the light chain or the heavy chain of the antibody on the C-terminal side or the N-terminal side thereof via a linker including one or more of amino acids.

15. The lyophilized formulation according to claim 1, wherein the fusion protein is a fusion protein in which the lysosomal enzyme is linked to the heavy chain of the antibody on the C-terminal side thereof via a linker including one or more of amino acids.

16. The lyophilized formulation according to claim 14, wherein the linker includes the amino acid sequence of Gly-Ser.

17. The lyophilized formulation according to claim 1, wherein the lysosomal enzyme is a human lysosomal enzyme.

18. The lyophilized formulation according to claim 17, wherein the human lysosomal enzyme is human iduronate-2-sulfatase.

19. The lyophilized formulation according to claim 1, wherein the lysosomal enzyme is selected from the group consisting of α-L-iduronidase, iduronate-2-sulfatase, glucocerebrosidase, β-galactosidase, GM2 activator protein, β-hexosaminidase A, β-hexosaminidase B, N-acetylglucosamine-1-phosphotransferase, α-mannosidase, β-mannosidase, galactosylceramidase, saposin C, arylsulfatase A, α-L-fucosidase, aspartyl glucosaminidase, α-N-acetylgalactosaminidase, acid sphingomyelinase, α-galactosidase, β-glucuronidase, heparan N-sulfatase, α-N-acetylglucosaminidase, acetyl-CoA:α-glucosaminide N-acetyltransferase, N-acetylglucosamine-6-sulfatase, acid ceramidase, amylo-1,6-glucosidase, sialidase, aspartylglucosaminidase, palmitoyl-protein thioesterase 1, tripeptidyl-peptidase 1, hyaluronidase 1, CLN1, and CLN2.

20. The lyophilized formulation according to claim 1, wherein the antibody is a human antibody or a humanized antibody.

21. The lyophilized formulation according to claim 20, wherein the antibody is a humanized anti-human transferrin receptor (hTfR) antibody.

22. The lyophilized formulation according to claim 17, wherein the antibody is a humanized anti-hTfR antibody, wherein the human lysosomal enzyme is human iduronate-2-sulfatase, wherein the fusion protein includes the humanized anti-hTfR antibody and the human iduronate-2-sulfatase, and wherein the fusion protein is selected from the group consisting of (a) to (c) below;
  (a) the fusion protein, wherein the light chain of the humanized anti-hTfR antibody has the amino acid sequence set forth as SEQ ID NO: 2, and wherein the heavy chain of the humanized anti-hTfR antibody having the amino acid sequence set forth as SEQ ID NO: 8 is linked, on the C-terminal side thereof, to the human iduronate-2-sulfatase via a linker sequence,
  (b) the fusion protein, wherein the light chain of the humanized anti-hTfR antibody has the amino acid sequence set forth as SEQ ID NO: 4, and wherein the heavy chain of the humanized anti-hTfR antibody having the amino acid sequence set forth as SEQ ID NO: 9 is linked, on the C-terminal side thereof, to the human iduronate-2-sulfatase via a linker sequence,
  (c) the fusion protein, wherein the light chain of the humanized anti-hTfR antibody has the amino acid sequence set forth as SEQ ID NO: 6, and wherein the heavy chain of the humanized anti-hTfR antibody having the amino acid sequence set forth as SEQ ID NO: 10 is linked, on the C-terminal side thereof, to the human iduronate-2-sulfatase via a linker sequence.

23. The lyophilized formulation according to claim 1, wherein the antibody recognizes a molecule present on the surface of a vascular endothelial cell as an antigen.

24. The lyophilized formulation according to claim 23, wherein the vascular endothelial cells are human vascular endothelial cells.

25. The lyophilized formulation according to claim 23, wherein the vascular endothelial cells are cerebral vascular endothelial cells.

26. The lyophilized formulation according to claim 25, wherein the molecule present on the surface of the cerebral vascular endothelial cell is selected from the group consisting of transferrin receptor (TfR), insulin receptor, leptin receptor, lipoprotein receptor, IGF receptor, OATP-F, organic anion transporter, MCT-8 and monocarboxylate transporter.

27. The lyophilized formulation according to claim 17, wherein the antibody is a humanized anti-hTfR antibody, wherein the human lysosomal enzyme is human iduronate-2-sulfatase, wherein the fusion protein includes the humanized anti-hTfR antibody and the human iduronate-2-sulfatase, and wherein the fusion protein is selected from the group consisting of (a) to (c) below;
  (a) the fusion protein, wherein the light chain of the humanized anti-hTfR antibody has the amino acid sequence set forth as SEQ ID NO: 2, and wherein the heavy chain of the humanized anti-hTfR antibody is linked, on the C-terminal side thereof and via a linker sequence of Gly-Ser, to the human iduronate-2-sulfatase, and the whole linked heavy chain has the amino acid sequence set forth as SEQ ID NO: 13,
  (b) the fusion protein, wherein the light chain of the humanized anti-hTfR antibody has the amino acid sequence set forth as SEQ ID NO: 4, and wherein the heavy chain of the humanized anti-hTfR antibody is linked, on the C-terminal side thereof and via a linker sequence of Gly-Ser, to the human iduronate-2-sulfatase, and the whole linked heavy chain has the amino acid sequence set forth as SEQ ID NO: 15, and
  (c) the fusion protein, wherein the light chain of the humanized anti-hTfR antibody has the amino acid sequence set forth as SEQ ID NO: 6, and wherein the heavy chain of the humanized anti-hTfR antibody is linked, on the C-terminal side thereof and via a linker sequence of Gly-Ser, to the human iduronate-2-sulfatase, and the whole linked heavy chain has the amino acid sequence set forth as SEQ ID NO: 17.

28. The lyophilized formulation according to claim 1, sealed in a container formed of a borosilicate glass or a hydrophobic resin.

29. The lyophilized formulation according to claim 28, wherein the container is formed by a cycloolefin copolymer, a ring-opened polymer of cycloolefin, or a hydrogenated ring-opened polymer of cycloolefin.

\* \* \* \* \*